(12) United States Patent
Taveras et al.

(10) Patent No.: US 7,960,433 B2
(45) Date of Patent: Jun. 14, 2011

(54) TREATMENT OF CHEMOKINE MEDIATED DISEASES

(75) Inventors: Arthur G. Taveras, Southborough, MA (US); Motasim Billah, Edison, NJ (US); Daniel Lundell, Flemington, NJ (US); William Kreutner, West Paterson, NJ (US); James Jakway, Bridgewater, NJ (US); Jay S. Fine, Bloomfield, NJ (US); Loretta A. Bober, Linden, NJ (US); Jianhua Chao, Pompton Lakes, NJ (US); Purakkattle J. Biju, Piscaraway, NJ (US); Younong Yu, East Brunswick, NJ (US)

(73) Assignee: Schering Corporation, Kenilworth, NJ (US)

(*) Notice: Subject to any disclaimer, the term of this patent is extended or adjusted under 35 U.S.C. 154(b) by 524 days.

(21) Appl. No.: 11/705,929

(22) Filed: Feb. 14, 2007

(65) Prior Publication Data

US 2007/0155756 A1    Jul. 5, 2007

Related U.S. Application Data

(62) Division of application No. 10/390,078, filed on Mar. 17, 2003, now abandoned.

(60) Provisional application No. 60/365,314, filed on Mar. 18, 2002.

(51) Int. Cl.
*A01N 43/08* (2006.01)
*A01N 43/02* (2006.01)
*A61K 31/34* (2006.01)
*A61K 31/335* (2006.01)

(52) U.S. Cl. .......................... 514/468; 514/449; 514/461

(58) Field of Classification Search ................. 514/471, 514/449, 461, 468
See application file for complete search history.

(56) References Cited

U.S. PATENT DOCUMENTS

| | | | |
|---|---|---|---|
| 4,170,588 A | 10/1979 | Hegenberg et al. | |
| 4,639,523 A | 1/1987 | Nohara et al. | |
| 5,206,252 A | 4/1993 | Butera et al. | |
| 5,354,763 A | 10/1994 | Butera et al. | |
| 5,397,790 A | 3/1995 | Butera et al. | |
| 5,401,753 A | 3/1995 | Butera et al. | |
| 5,403,853 A | 4/1995 | Butera et al. | |
| 5,466,712 A | 11/1995 | Butera et al. | |
| 5,506,252 A | 4/1996 | Butera et al. | |
| 5,532,245 A | 7/1996 | Butera et al. | |
| 5,840,764 A | 11/1998 | Quaqliato et al. | |
| 6,297,265 B2 | 10/2001 | Widdowson et al. | |
| 6,300,325 B1 | 10/2001 | Widdowson et al. | |
| 6,376,555 B1 | 4/2002 | Butera et al. | |
| 6,420,396 B1 | 7/2002 | Albers et al. | |
| 6,878,709 B2 | 4/2005 | Taveras et al. | |
| 6,903,131 B2 | 6/2005 | Taveas et al. | |
| 7,132,445 B2 | 11/2006 | Taveas et al. | |
| 2002/0028238 A1* | 3/2002 | Karim et al. | 424/461 |
| 2003/0204085 A1 | 10/2003 | Taveras et al. | |
| 2004/0186142 A1 | 9/2004 | Taveras et al. | |

FOREIGN PATENT DOCUMENTS

| | | |
|---|---|---|
| DE | 26 38 855 A | 3/1978 |
| DE | 33 09 655 A1 | 9/1984 |
| EP | 0 275 997 A | 7/1988 |
| EP | 0 376 079 A | 7/1990 |
| EP | 0 796 243 B1 | 1/1999 |
| FR | 1 531 943 A | 7/1968 |
| GB | 1186096 | 4/1970 |
| WO | WO 94/29277 | 12/1994 |
| WO | WO 95/14005 | 5/1995 |
| WO | WO 96/14300 | 5/1996 |
| WO | WO 96/15103 | 5/1996 |
| WO | WO 98/33763 | 8/1998 |
| WO | WO 00/20378 | 4/2000 |
| WO | WO 00/21927 A | 4/2000 |
| WO | WO 00/35855 | 6/2000 |
| WO | WO 00/35864 | 6/2000 |
| WO | WO 00/73260 A1 | 12/2000 |
| WO | WO 01/29000 A2 | 4/2001 |
| WO | WO 01/64208 A1 | 9/2001 |
| WO | WO 01/64691 A1 | 9/2001 |
| WO | WO 01/68569 A2 | 9/2001 |
| WO | WO 01/92202 A1 | 12/2001 |
| WO | WO 02/057230 A1 | 7/2002 |
| WO | WO 02/067919 A1 | 9/2002 |
| WO | WO 02/076926 A1 | 10/2002 |

(Continued)

OTHER PUBLICATIONS

Chemical Abstract 66:18527 for Maahs, Guenther, et al., "Syntheses and derivatives of squaric acid," *Angewandte Chemie* 78(20):927-31 (1966) (which is attached to said abstract).

(Continued)

*Primary Examiner* — Yong S Chong
(74) *Attorney, Agent, or Firm* — Eric A. Meade; Henry C. Jeannette; Mark Russell

(57) ABSTRACT

Methods of treating chemokine-mediated diseases are disclosed. The methods comprise the administration of CXC-Chemokine receptor antagonists of the formula

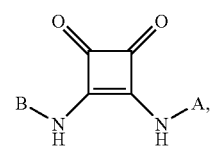

(I)

or pharmaceutically acceptable salts or solvates thereof, in combination with other classes of pharmaceutical compounds. The chemokine-mediated diseases include acute and chronic inflammatory disorders, psoriasis, cystic fibrosis, asthma and cancer. Also disclosed are novel compounds of formula (I).

11 Claims, No Drawings

FOREIGN PATENT DOCUMENTS

| | | |
|---|---|---|
| WO | WO 02/083624 A1 | 10/2002 |
| WO | WO 03/080063 A | 10/2003 |

OTHER PUBLICATIONS

Chemical Abstract 87:134383 for Augustin, Manfred, et al., "Disubstitution in 2,3-dichloromaleimides" *Zeitschrift Fuer Chemie* 17(6):215-216 (1977) (which is attached to said abstract).

Chemical Abstract No. 87:151727 for Ehrhardt, Heinz, et al., "Amides and thioamides of squaric acid: syntheses and reactions," *Chemische Berichte* 110(7):2506-23 (1977) (which is attached to said abstract).

Chemical Abstract 104:129517 for Gruenefeld, Johann, et al., "Reactions of squaric acid with carbodiimides," *Archlv der Pharmazie* 318(12):1062-70 (1985) (which is attached to said abstract).

Chemical Abstract No. 122:160745 for Tillack, Annegret, et al., "Assymmetric catalysis. IV. Hydrosilylation of acetophenone with pyrroline-2,5-dione modified [Rh(COD)C1]2 catalyst," *Journal of Organometallic Chemistry* 482:85-91 (1994) (which is attached to said abstract).

Chemical Abstract No. 125:300482 for Chen, Yizhao, et al., "Reaction of dibutyl oxosquarate with aromatic primary amines," *Sichuan Daxue Xuebao, Ziran Kexueban* 33(2):182-186 (1996) (which is attached to said abstract).

Chemical Abstract No. 130:222994 for Chen, Yi-Zhao, et al., "Synthesis of asymmetric aryl-substituted amides of squaric acid and asymmetric isosquarylium amides," *Hechen Huaxue* 6(4):383-392 (1998) (which is attached to said abstract).

Butera, John A., et al., "Design and SAR of Novel Potassium Channel Openers Targeted for Urge Urinary Incontinence. 1. *N*-Cyanoguanidine Bioisosteres Possessing in Vivo Bladder Selectivity," *J. Med. Chem.* 43:1187-1202 (2000).

Davis, Peter D., et al., "Inhibitors of protein kinase C 1. 2,3-Bisarylmaleimides," *J. Med. Chem.* 35:177-184 (1992).

Hanaineh-Abdelnour, Leila, et al., "Some synthetic applications of 2,3-Dichloro-*N*-phenylmaleimide: A Novel Synthesis of 2-Phenylpyrrolo[3,4-*b*]quinoxaline-1,3-diones. I," *Tetrahedron* 55:11859-11870 (1999).

Neuse, Eberhard W., et al., "Poly(squaryl amides)" *Polymer* 15:339-45 (1974).

Patent Abstracts of Japan, vol. 018, No. 361 (c-1222), Jul. 7, 1994 and JP 06 092915A, Apr. 5, 1994 abstract.

Zhou, Hai-Bing, et al., "Design, synthesis and structure of new chiral squaric acid monoaminoalcohols and diaminoalcohols and their use as catalysts in asymmetric reduction of ketones and diketones," *Tetrahedron* 57:9325-9333 (2001).

Glynn, P.C., Hall, H.I.P. Pulmonary Pharmacology & Therapeutics 2002, 15, 103-110.

Hay, D.W.P.; Sarau, H.M., Curr. Opin. Pharmacology 2001,1, 242-247.

Miller, D.D., In "Structure-Activity Relationship and Drug Design" Remington: The Science and Practice or Pharmacv, Nineteenth Edition vol. 1 (1995) Easton, PA: Mack Publishing Co. p. 425.

PCT International Search Report dated Jun. 24, 2003 for corresponding PCT Application No. PCT/US03/08287.

* cited by examiner

TREATMENT OF CHEMOKINE MEDIATED DISEASES

REFERENCE TO RELATED APPLICATION

This application claims the benefit of U.S. Provisional Application No. 60/365314 filed Mar. 18, 2002, the disclosure of which is incorporated herein by reference thereto.

This invention described herein was made by one of the parties which is subject to a joint research agreement between Schering Corporation and Pharmacopeia Drug Discovery, Inc.

FIELD OF THE INVENTION

This invention relates to the treatment of chemokine mediated diseases using CXC chemokine receptor antagonists in combination (or association) with other pharmaceutical compounds.

BACKGROUND OF THE INVENTION

Chemokines are chemotactic cytokines that are released by a wide variety of cells to attract macrophages, T-cells, eosinophils, basophils, neutrophils and endothelial cells to sites of inflammation and tumor growth. There are two main classes of chemokines, the CXC-chemokines and the CC-chemokines. The class depends on whether the first two cysteines are separated by a single amino acid (CXC-chemokines) or are adjacent (CC-chemokines). The CXC-chemokines include interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. CC chemokines include RANTES, MIP-1α, MIP-2β, monocyte chemotactic protein-1 (MCP-1), MCP-2, MCP-3 and eotaxin. Individual members of the chemokine families are known to be bound by at least one chemokine receptor, with CXC-chemokines generally bound by members of the CXCR class of receptors, and CC-chemokines by members of the CCR class of receptors. For example, IL-8 is bound by the CXCR-1 and CXCR-2 receptors.

Since CXC-chemokines promote the accumulation and activation of neutrophils, these chemokines have been implicated in a wide range of acute and chronic inflammatory disorders including psoriasis and rheumatoid arthritis. Baggiolini et al., FEBS Lett. 307, 97 (1992); Miller et al., Crit. Rev. Immunol. 12, 17 (1992); Oppenheim et al., Annu. Fev. Immunol. 9, 617 (1991); Seitz et al., J. Clin. Invest. 87, 463 (1991); Miller et al., Am. Rev. Respir. Dis. 146, 427 (1992); Donnely et al., Lancet 341, 643 (1993).

Hence, the CXC-chemokine receptors represent promising targets for the development of novel anti-inflammatory agents.

There remains a need for an improved method of treating CXC-chemokine mediated diseases. For example, conditions associated with an increase in IL-8 production (which is responsible for chemotaxis of neutrophil and T-cell subsets into the inflammatory site) would benefit by an improved method that inhibits IL-8 receptor binding. Such an improved method is provided by this invention.

SUMMARY OF THE INVENTION

This invention provides a method of treating a CXC chemokine mediated disease comprising administering to a patient (i.e., a mammal, e.g. human) in need of such treatment, a therapeutically effective amount of:

(a) One or more (e.g., one) compounds of the formula (I):

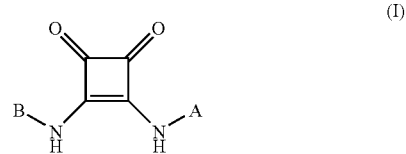

or a pharmaceutically acceptable salt or solvate thereof; and (b) One or more drugs, agents or therapeutics useful for the treatment of chemokine mediated diseases.

In one embodiment, the invention provides a method of treating a chemokine mediated disease comprising administering to a patient (e.g., a human) in need of such treatment, an effective amount of one or more (e.g., one) compounds of formula (I) in combination (or association) with an effective amount of one or more disease modifying antirheumatic drugs (DMARDs) such as, for example, methotrexate, azathioptrine, luflunomide, penicillamine, gold salts, mycophenolate, mofetil, cyclophosphamide and the like.

In another embodiment, the invention provides a method of treating a chemokine mediated disease comprising administering to a patient (e.g., a human) in need of such treatment, an effective amount of one or more (e.g., one) compounds of formula (I) in combination (or association) with an effective amount of one or more nonsteroidal anti-inflammatory drugs (NSAIDs) such as, for example, piroxicam, ketoprofen, naproxen, indomethacin, ibuprofen and the like.

In another embodiment the invention provides a method of treating a chemokine mediated disease comprising administering to a patient (e.g., a human) in need of such treatment, an effective amount of one or more (e.g., one) compounds of formula (I) in combination (or association) with an effective amount of one or more compounds selected from the group consisting of:

(a) a disease modifying antirheumatic drug (such as, for example, methotrexate, azathioptrine, luflunomide, penicillamine, gold salts, mycophenolate, mofetil, cyclophosphamide and the like);

(b) a nonsteroidal antiinflammatory drug (such as, for example, piroxicam, ketoprofen, naproxen, indomethacin, ibuprofen and the like);

(c) COX-2 selective inhibitors such as, for example, rofecoxib and celecoxib;

(d) COX-1 inhibitors such as, for example, piroxicam;

(e) immunosuppressives such as, for example, methotrexate, cyclosporin, leflunimide, tacrolimus, rapamycin or sulfasalazine; and (f) steroids such as, for example, betamethasone, cortisone, prednisone or dexamethasone.

In another embodiment the invention provides a method of treating a chemokine mediated disease comprising administering to a patient (e.g., a human) in need of such treatment, an effective amount of one or more (e.g., one) compounds of formula (I) in combination (or association) with an effective amount of one or more compounds selected from the group consisting of:

(a) a disease modifying antirheumatic drug (such as, for example, methotrexate, azathioptrine, luflunomide, penicillamine, gold salts, mycophenolate, mofetil, cyclophosphamide and the like);

(b) a nonsteroidal antiinflammatory drug (such as, for example, piroxicam, ketoprofen, naproxen, indomethacin, ibuprofen and the like);

(c) COX-2 selective inhibitors such as, for example, rofecoxib and celecoxib;

(d) COX-1 inhibitors such as, for example, piroxicam;

(e) immunosuppressives such as, for example, methotrexate, cyclosporin, leflunimide, tacrolimus, rapamycin or sulfasalazine;

(f) steroids such as, for example, betamethasone, cortisone, prednisone or dexamethasone;

(g) a biological response modifier and (h) other anti-inflammatory agents or therapeutics useful for the treatment of chemokine mediated diseases.

In another embodiment, the invention provides a method of treating a chemokine mediated disease comprising administering to a patient (e.g., a human) in need of such treatment, an effective amount of one or more (e.g., one) compounds of formula (I), in combination (or association) with an effective amount of one or more biological response modifiers (BRMs) such as, for example, anti-TNF antagonists including antibodies and/or receptors/receptor fragments, IL-1 antagonists, anti-CD40, anti-CD28, IL-10, anti-adhesion molecules and the like.

In another embodiment, the invention provides a method of treating a chemokine mediated disease comprising administering to a patient (e.g., a human) in need of such treatment, an effective amount of one or more (e.g., one) compounds of formula (I) in combination (or association) with an effective amount of one or more compounds selected from the group consisting of:

a) anti-inflammatory agents such as, for example, p38 kinase inhibitors, PDE4 inhibitors, and TACE inhibitors;

b) chemokine receptor antagonists such as, for example, thalidomide;

c) leukotriene inhibitors; and d) other small molecule inhibitors of pro-inflammatory cytokine production.

In another embodiment, the invention provides a method of treating a chemokine mediated disease, said disease being a pulmonary disease (e.g., COPD, asthma, or cystic fibrosis) comprising administering to a patient (e.g., a human) in need of such treatment, an effective amount of one or more (e.g., one) compounds of formula (I) in combination (or association) with an effective amount of one or more compounds selected from the group consisting of: glucocorticoids, 5-lipoxygenase inhibitors, β-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-b agonists, nociceptin agonists, expectorants, mucolytic agents, decongestants, antioxidants, anti-IL-8 anti-bodies, anti-IL-5 antibodies, anti-IgE antibodies, anti-TNF antibodies, IL-10, adhesion molecule inhibitors, and growth hormones. Agents that belong to these classes include, but are not limited to, beclomethasone, mometasone, ciclesonide, budesonide, fluticasone, albuterol, salmeterol, formoterol, loratadine, desloratadine, tiotropium bromide, MSI-ipratropium bromide, montelukast, theophilline, cilomilast, roflumilast, cromolyn, ZD-4407, talnetant, LTB-019, revatropate, pumafentrine, CP-955, AR-C-89855, BAY-19-8004, GW-328267, QAB-149, DNK-333, YM-40461 and TH-9506 (or pharmaceutically acceptable formulations thereof).

In another embodiment, the invention provides a method of treating a chemokine mediated disease, said disease being multiple sclerosis comprising administering to a patient in need of such treatment a therapeutically effective amount of one or more (e.g., one) compounds of formula (I) in combination (or association) with an effective amount of one or more compounds selected from the group consisting of methotrexate, cyclosporin, leflunimide, sulfasalazine, β-methasone, β-interferon, glatiramer acetate, prednisone, etonercept, infliximab, and formulations thereof.

In another embodiment, the invention provides a method of treating a chemokine mediated disease, said disease being rheumatoid arthritis comprising administering to a patient in need of such treatment an effective amount of one or more (e.g., one) compounds of formula (I) in combination (or association) with an effective amount of one or more compounds selected from the group consisting of a COX-2 inhibitor, a COX inhibitor, an immunosuppressive, a steroid, a PDE IV inhibitor, an anti-TNF-α compound, MMP inhibitors, glucocorticoids, chemokine inhibitors, CB2-selective inhibitors, other classes of compounds indicated for the treatment of rheumatoid arthritis, and formulations thereof.

In another embodiment, the invention provides a method of treating a chemokine mediated disease, said disease being rheumatoid arthritis comprising administering to a patient in need of such treatment an effective amount of one or more (e.g., one) compounds of formula (I) in combination (or association) with an effective amount of one or more compounds selected from the group consisting of a COX-2 inhibitor, a COX inhibitor, an immunosuppressive, a steroid, a PDE IV inhibitor, an anti-TNF-α compound, MMP inhibitors, glucocorticoids, chemokine inhibitors, and CB2-selective inhibitors.

In another embodiment, the invention provides a method of treating a chemokine mediated disease, said disease being stroke and cardiac reperfusion injury comprising administering to a patient in need of such treatment an effective amount of one or more (e.g., one) compounds of formula (I) in combination (or association) with an effective amount of one or more compounds selected from the group consisting of thrombolitics, antiplatelet agents, gpIIb/IIIa antagonist, anticoagulants, other compounds indicated for the treatment of rheumatoid arthritis and formulations thereof.

In another embodiment, the invention provides a method of treating a chemokine mediated disease, said disease being stroke and cardiac reperfusion injury comprising administering to a patient in need of such treatment an effective amount of one or more (e.g., one) compounds of formula (I) in combination (or association) with an effective amount of one or more compounds selected from the group consisting of thrombolitics, antiplatelet agents, gpIIb/IIIa antagonist, and anticoagulants.

In another embodiment, the invention provides a method of treating a chemokine mediated disease, said disease being stroke and cardiac reperfusion injury comprising administering to a patient in need of such treatment an effective amount of one or more (e.g., one) compounds of formula (I) in combination (or association) with an effective amount of one or more compounds selected from the group consisting of an effective amount of one or more compounds selected from the group consisting of tenecteplase, TPA, alteplase, abciximab, eftiifbatide, heparin and formulations thereof.

This invention also provides novel compounds of formula (I), wherein said novel compounds are selected from the group consisting of:

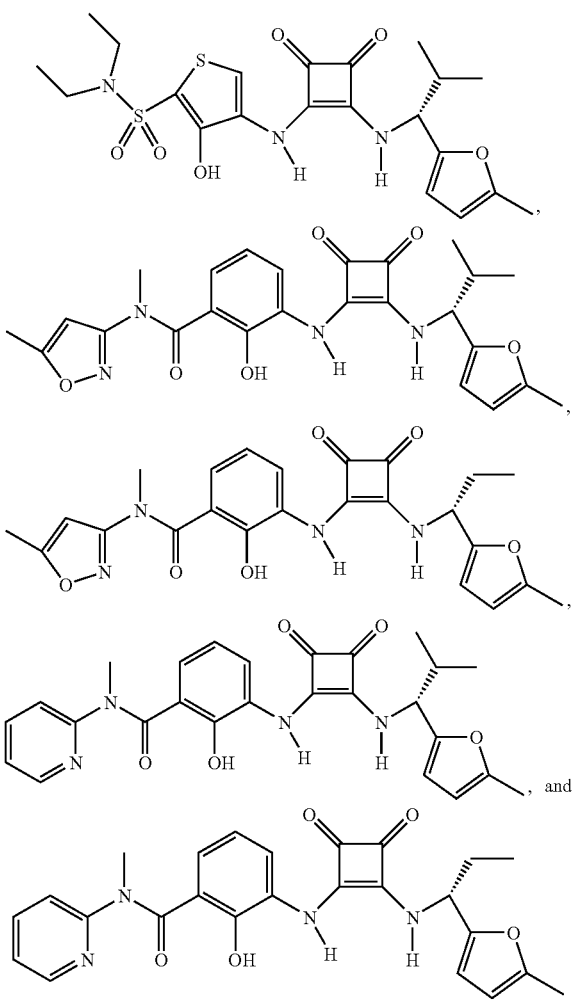

or the pharmaceutically acceptable salts or solvates thereof.

DETAILED DESCRIPTION OF THE INVENTION

Unless indicated otherwise, the following definitions apply throughout the present specification and claims. These definitions apply regardless of whether a term is used by itself or in combination with other terms. Hence the definition of "alkyl" applies to "alkyl" as well as to the "alkyl" portions of "alkoxy", etc.

When any variable (e.g., aryl, $R^2$) occurs more than one time in any constituent, its definition on each occurrence is independent of its definition at every other occurrence. Also, combinations of substituents and/or variables are permissible only if such combinations result in stable compounds.

"An effective amount" means a therapeutically effective amount, e.g., an amount that provides a clinical response to the disease being treated.

Examples of "one or more" include (a) 1, 2 or 3, (b) 1 or 2, or (c) 1.

Examples of "at least one" include (a) 1, 2 or 3, (b) 1 or 2, or (c) 1.

"Bn" represents benzyl.

"Alkyl" means a straight or branched saturated hydrocarbon chain having the designated number of carbon atoms. Where the number of carbon atoms is not specified, 1 to 20 carbons are intended. Preferred alkyl groups contain 1 to 12 carbon atoms in the chain. More preferred alkyl groups contain 1 to 6 carbon atoms in the chain.

"Alkoxy" means an alkyl-O group in which alkyl is as previously defined. Non-limiting examples of alkoxy groups include methoxy, ethoxy, n-propoxy, iso-propoxy and n-butoxy. The bond to the parent moiety is through the ether oxygen.

"Alkenyl" means an aliphatic hydrocarbon group containing at least one carbon-carbon double bond and which may be straight or branched. Where the number of carbon atoms is not specified, 2 to 20 carbons are intended. Preferred alkenyl groups have 2 to 12 carbon atoms in the chain; and more preferably 2 to 6 carbon atoms in the chain. Non-limiting examples of suitable alkenyl groups include ethenyl, propenyl, n-butenyl, 3-methylbut-2-enyl, n-pentenyl, octenyl and decenyl. Alkenylalkyl means that the alkenyl group is attached to the parent moiety through an alkyl group.

"Alkynyl" means an aliphatic hydrocarbon group containing at least one carbon-carbon triple bond and which may be straight or branched. Where the number of carbon atoms is not specified, 2 to 15 carbons are intended. Preferred alkynyl groups have 2 to 12 carbon atoms in the chain; and more preferably 2 to 4 carbon atoms in the chain. Non-limiting examples of suitable alkynyl groups include ethynyl, propynyl, 2-butynyl, 3-methylbutynyl, n-pentynyl, and decynyl. Alkynylalkyl means that the alkynyl group is attached to the parent moiety through an alkyl group.

"Aryl" means an aromatic monocyclic or multicyclic ring system comprising about 6 to about 14 carbon atoms, preferably about 6 to about 10 carbon atoms. Non-limiting examples of suitable aryl groups include phenyl, naphthyl, indenyl, tetrahydronaphthyl, indanyl, anthracenyl, fluorenyl and the like.

"Arylalkyl" means an aryl-alkyl group in which the aryl and alkyl groups are as defined. Non-limiting examples of suitable alkylaryl groups include o-tolyl, p-tolyl and xylyl. The bond to the parent moiety is through the alkyl group.

"Cycloalkyl" means a non-aromatic ring system having 3 to 10 carbon atoms and one to three rings, preferably 5 to 10 carbon atoms. Preferred cycloalkyl rings contain 5 to 7 ring atoms. Non-limiting examples of cycloalkyl groups include cyclopropyl, cyclopentyl, cyclohexyl, cycloheptyl, norbornyl, adamantyl and the like.

"Cycloalkylalkyl" means a cycloalkyl group attached to the parent moiety through an alkyl group. Non-limiting examples include cyclopropylmethyl, cyclohexylmethyl and the like.

"Cycloalkenyl" means a non-aromatic mono or multicyclic ring system comprising 3 to 10 carbon atoms, preferably 5 to 10 carbon atoms which contains at least one carbon-carbon double bond. Preferred cycloalkenyl rings contain 5 to 7 ring atoms. Non-limiting examples of cycloalkyl groups include cyclopentenyl, cyclohexenyl, cycloheptenyl, norbornenyl and the like.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine or bromine, and more preferred are fluorine and chlorine.

"Haloalkyl" means an alkyl group as defined above wherein one or more hydrogen atoms on the alkyl is replaced by a halo group defined above.

"Heterocyclyl" or "heterocyclic" means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term heterocyclic acidic functional group is intended to include groups such as, pyrrole, imidazole, triazole, tetrazole, and the like.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heteroarylalkyl" means a heteroaryl-alkyl group where the bond to the parent moiety is through an alkyl group.

N-oxides can form on a tertiary nitrogen present in an R substituent, or on =N— in a heteroaryl ring substituent and are included in the compounds of formula I.

As used herein, the term "composition" is intended to encompass a product comprising the specified ingredients in the specified amounts, as well as any product which results, directly or indirectly, from combination of the specified ingredients in the specified amounts.

Compounds of formula (I) are described in WO 02/076926 published Oct. 3, 2002, and WO 02/083624 published Oct. 24, 2002, the disclosures of each being incorporated herein by reference thereto.

Examples of chemokine mediated diseases include: psoriasis, atopic dermatitis, asthma, COPD, adult respiratory disease, arthritis, inflammatory bowel disease, Crohn's disease, ulcerative colitis, septic shock, endotoxic shock, gram negative sepsis, toxic shock syndrome, stroke, cardiac and renal reperfusion injury, glomerulonephritis, thrombosis, Alzheimer's disease, graft vs. host reaction, allograft rejections, malaria, acute respiratory distress syndrome, delayed type hypersensitivity reaction, atherosclerosis, cerebral and cardiac ischemia, osteoarthritis, multiple sclerosis, restinosis, angiogenesis, osteoporosis, gingivitis, respiratory viruses, herpes viruses, hepatitis viruses, HIV (e.g., AIDS), Kaposi's sarcoma associated virus, meningitis, cystic fibrosis, preterm labor, cough, pruritis, multi-organ dysfunction, trauma, strains, sprains, contusions, psoriatic arthritis, herpes, encephalitis, CNS vasculitis, traumatic brain injury, CNS tumors, subarachnoid hemorrhage, post surgical trauma, interstitial pneumonitis, hypersensitivity, crystal induced arthritis, acute and chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred and corneal neovascularization, polymyositis, vasculitis, acne, gastric and duodenal ulcers, celiac disease, esophagitis, glossitis, airflow obstruction, airway hyperresponsiveness, bronchiectasis, bronchiolitis, bronchiolitis obliterans, chronic bronchitis, cor pulmonae, cough, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy, periodontitis, transplant reperfusion injury and early transplantation.

Examples of anti-adhesion molecules include anti-CD11a (efalizumab), CD58-Fc (alefacept), anti-VLA (natalizumab), as well as small molecule antagonists of LFA-1 (such as IC-747), VLA4 (such as GW559090), and LFA-3. Examples of leukotriene inhibitors include LTD4 receptor antagonists (e.g., Singulair), Zileuton, and inhibitors of 5-lipoxygenase. Examples of inhibitors of cytokine production include inhibitors of TNF-α such as thalidomide. Examples of other classes of compounds indicated for the treatment of rheumatoid arthritis include inhibitors of p38 kinase, TNF-α converting enzyme (TACE), nitiric oxide synthase and methotrexate.

For the compounds of formula (I):

A is selected from the group consisting of:

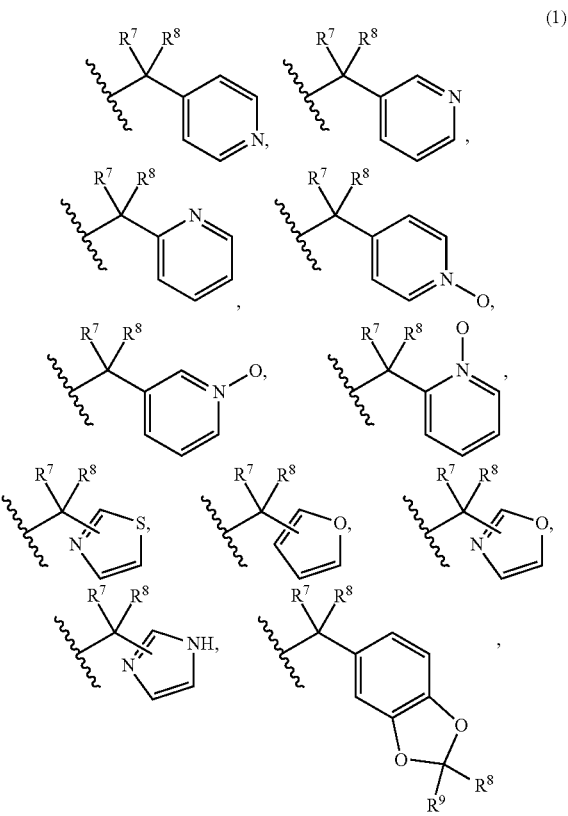

(1)

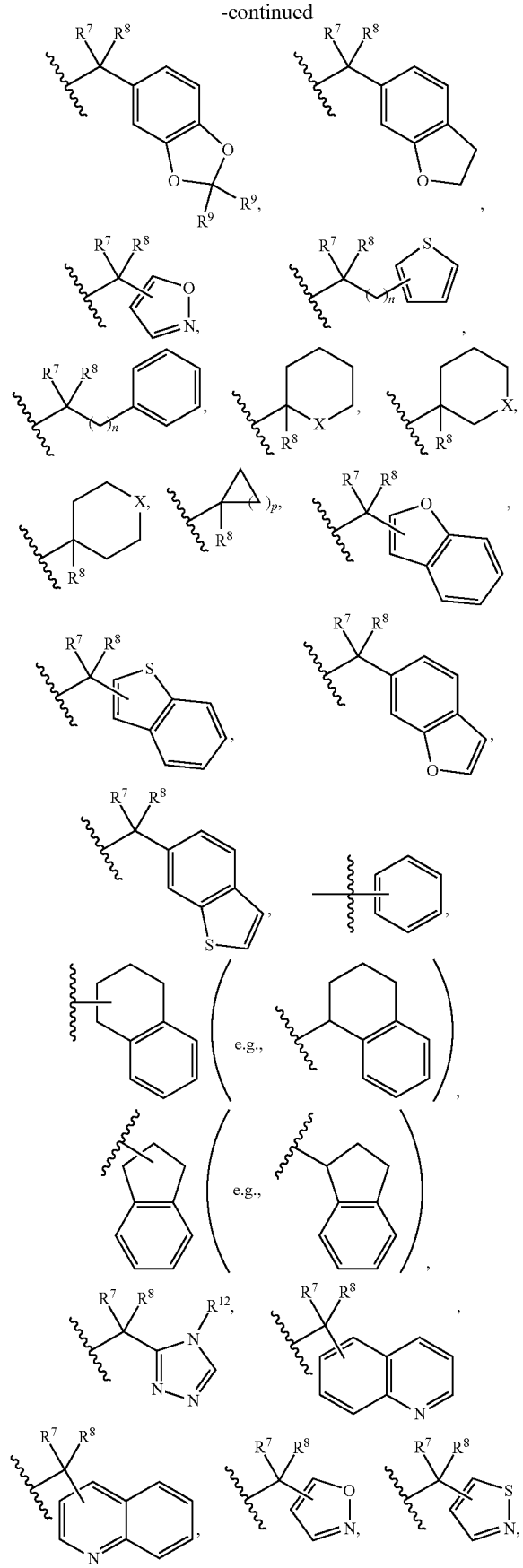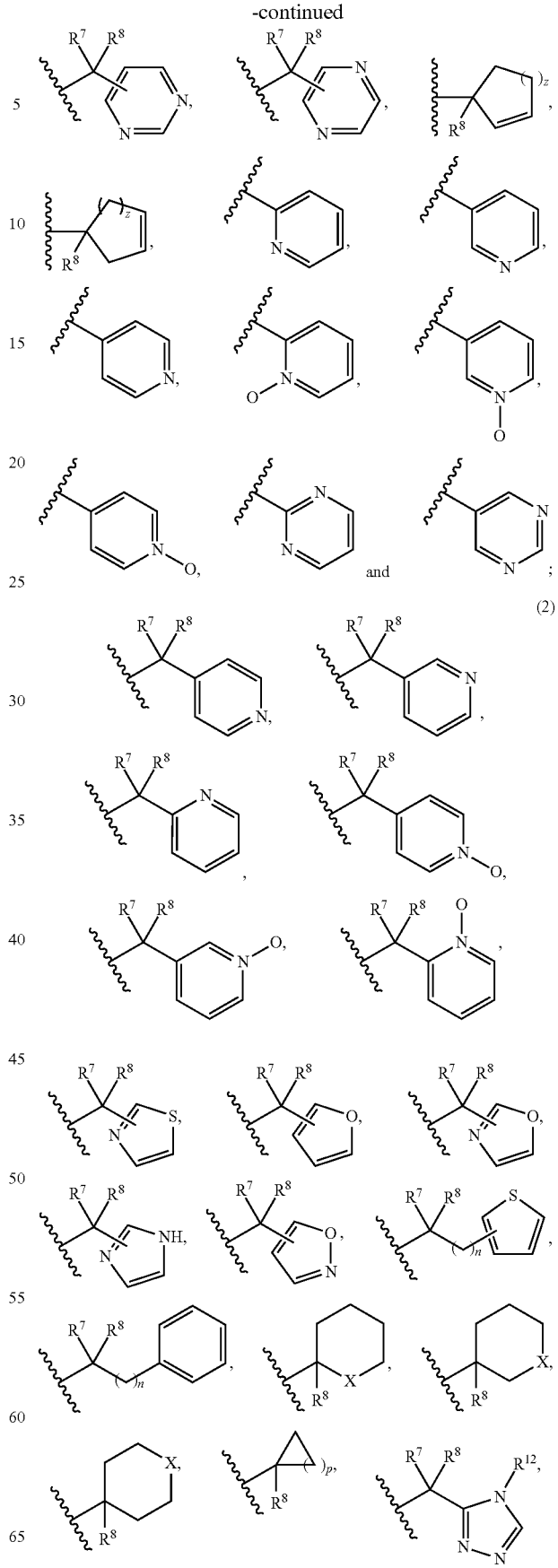

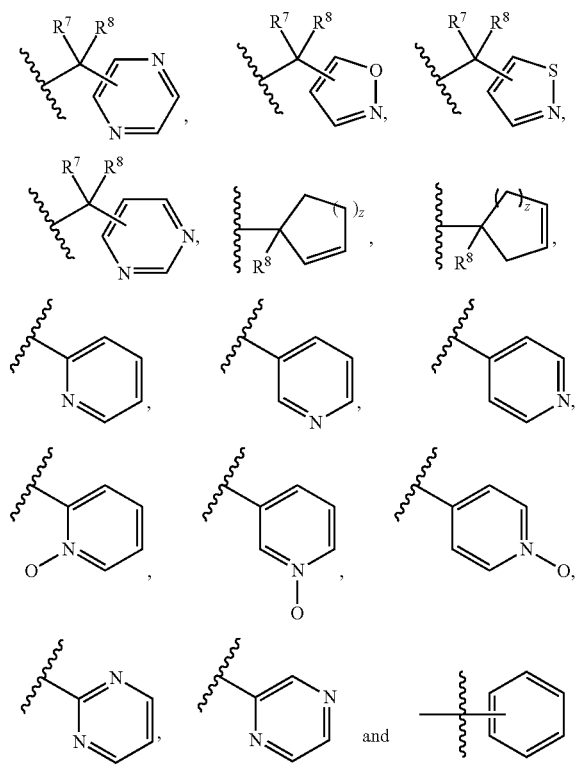

wherein the above rings of said A groups are substituted with 1 to 6 substituents each independently selected from the group consisting of: $R^9$ groups;

(3)

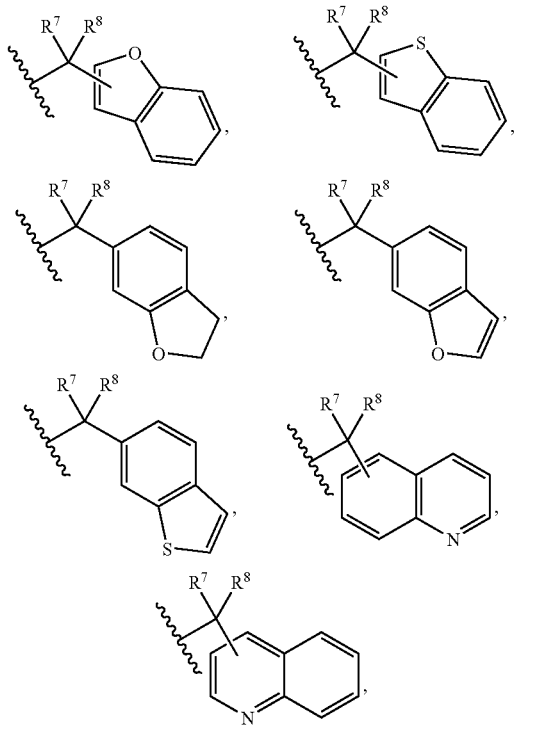

wherein one or both of the above rings of said A groups are substituted with 1 to 6 substituents each independently selected from the group consisting of: $R^9$ groups;

(4)

wherein the above phenyl rings of said A groups are substituted with 1 to 3 substituents each independently selected from the group consisting of: $R^9$ groups; and (5)

B is selected from the group consisting of

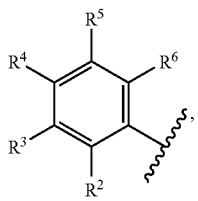 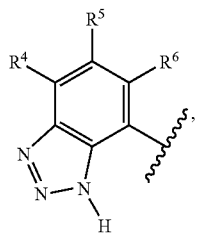

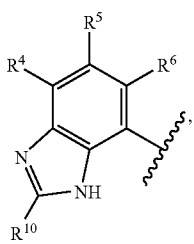 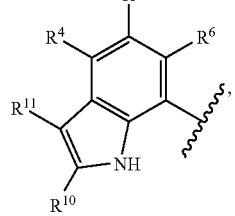

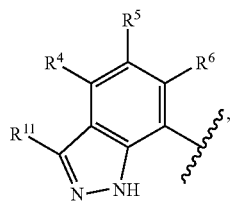 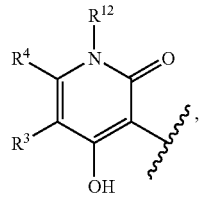

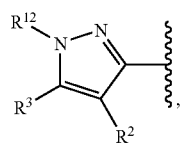 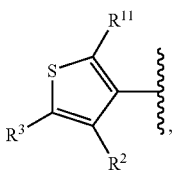

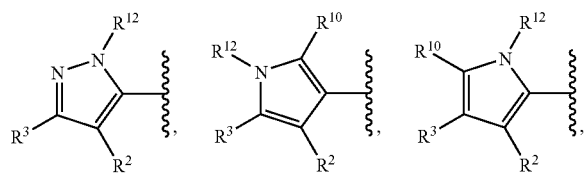

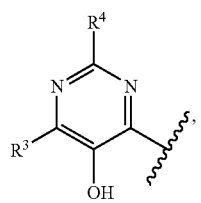

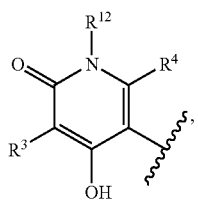

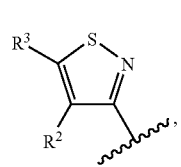 and

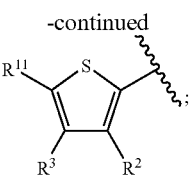

n is 0 to 6;
p is 1 to 5;
X is O, NH, or S;
Z is 1 to 3;
$R^2$ is selected from the group consisting of: hydrogen, OH, —C(O)OH, —SH, —SO$_2$NR$^{13}$R$^{14}$, —NHC(O)R$^{13}$, —NHSO$_2$NR$^{13}$R$^{14}$, —NHSO$_2$R$^{13}$, —NR$^{13}$R$^{14}$, —C(O)NR$^{13}$R$^{14}$, —C(O)NHOR$^{13}$, —C(O)NR$^{13}$OH, —S(O$_2$)OH, —OC(O)R$^{13}$, an unsubstituted heterocyclic acidic functional group, and a substituted heterocyclic acidic functional group; wherein there are 1 to 6 substituents on said substituted heterocyclic acidic functional group each substituent being independently selected from the group consisting of: R$^9$ groups;
each R$^3$ and R$^4$ is independently selected from the group consisting of: hydrogen, cyano, halogen, alkyl, alkoxy, —OH, —CF$_3$, —OCF$_3$, —NO$_2$, —C(O)R$^{13}$, —C(O)OR$^{13}$, —C(O)NHR$^{17}$, —C(O)NR$^{13}$R$^{14}$, —SO$_{(t)}$NR$^{13}$R$^{14}$, —SO$_{(t)}$R$^{13}$, —C(O)NR$^{13}$OR$^{14}$, unsubstituted or substituted aryl, unsubstituted or substituted heteroaryl,

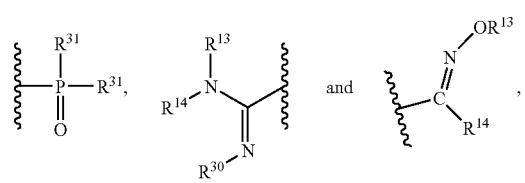

wherein there are 1 to 6 substituents on said substituted aryl group and each substituent is independently selected from the group consisting of: R$^9$ groups; and wherein there are 1 to 6 substituents on said substituted heteroaryl group and each substituent is independently selected from the group consisting of: R$^9$ groups;
each R$^5$ and R$^6$ are the same or different and are independently selected from the group consisting of hydrogen, halogen, alkyl, alkoxy, —CF$_3$, —OCF$_3$, —NO$_2$, —C(O)R$^{13}$, —C(O)OR$^{13}$, —C(O)NR$^{13}$R$^{14}$, —SO$_{(t)}$NR$^{13}$R$^{14}$, —C(O)NR$^{13}$OR$^{14}$, cyano, unsubstituted or substituted aryl, and unsubstituted or substituted heteroaryl group; wherein there are 1 to 6 substituents on said substituted aryl group and each substituent is independently selected from the group consisting of: R$^9$ groups; and wherein there are 1 to 6 substituents on said substituted heteroaryl group and each substituent is independently selected from the group consisting of: R$^9$ groups;
each R$^7$ and R$^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —CO$_2$R$^{13}$, —CONR$^{13}$R$^{14}$, alkynyl, alkenyl, and cycloalkenyl; and wherein there are one or more (e.g., 1 to 6) substituents on said substituted R$^7$ and R$^8$ groups, wherein each substitutent is independently selected from the group consisting of:

a) halogen,
b) —$CF_3$,
c) —$COR^{13}$,
d) —$OR^{13}$,
e) —$NR^{13}R^{14}$,
f) —$NO_2$,
g) —CN,
h) —$SO_2OR^{13}$,
i) —Si(alkyl)$_3$, wherein each alkyl is independently selected,
j) —Si(aryl)$_3$, wherein each alkyl is independently selected,
k) —$(R^{13})_2R^{14}Si$, wherein each $R^{13}$ is independently selected,
l) —$CO_2R^{13}$,
m) —$C(O)NR^{13}R^{14}$,
n) —$SO_2NR^{13}R^{14}$,
o) —$SO_2R^{13}$,
p) —$OC(O)R^{13}$,
q) —$OC(O)NR^{13}R^{14}$,
r) —$NR^{13}C(O)R^{14}$, and
s) —$NR^{13}CO_2R^{14}$;

(fluoroalkyl is one non-limiting example of an alkyl group that is substituted with halogen);

$R^{8a}$ is selected from the group consisting of: hydrogen, alkyl, cycloalkyl and cycloalkylalkyl;

each $R^9$ is independently selected from the group consisting of:
a) —$R^{13}$,
b) halogen,
c) —$CF_3$,
d) —$COR^{13}$,
e) —$OR^{13}$,
f) —$NR^{13}R^{14}$,
g) —$NO_2$,
h) —CN,
i) —$SO_2R^{13}$,
j) —$SO_2NR^{13}R^{14}$,
k) —$NR^{13}COR^{14}$,
l) —$CONR^{13}R^{14}$,
m) —$NR^{13}CO_2R^{14}$,
n) —$CO_2R^{13}$,
o)

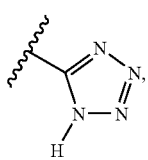

p) alkyl substituted with one or more (e.g., one) —OH groups (e.g., —$(CH_2)_qOH$, wherein q is 1-6, usually 1 to 2, and preferably 1),
q) alkyl substituted with one or more (e.g., one) —$NR^{13}R^{14}$ group (e.g., —$(CH_2)_qNR^{13}R^{14}$, wherein q is 1-6, usually 1 to 2, and preferably 1), and
r) —$N(R^{13})SO_2R^{14}$ (e.g., $R^{13}$ is H and $R^{14}$ is alkyl, such as methyl);

each $R^{10}$ and $R^{11}$ is independently selected from the group consisting of $R^{13}$, (e.g., hydrogen and alkyl (e.g., $C_1$ to $C_6$ alkyl, such as methyl)), halogen, —$CF_3$, —$OCF_3$, —$NR^{13}R^{14}$, —$NR^{13}C(O)NR^{13}R^{14}$, —OH, —$C(O)OR^{13}$, —SH, —$SO_{(t)}NR^{13}R^{14}$, —$SO_2R^{13}$, —$NHC(O)R^{13}$, —$NHSO_2NR^{13}R^{14}$, —$NHSO_2R^{13}$, —$C(O)NR^{13}R^{14}$, —$C(O)NR^{13}OR^{14}$, —$OC(O)R^{13}$ and cyano;

$R^{12}$ is selected from the group consisting of: hydrogen, —$C(O)OR^{13}$, unsubstituted or substituted aryl, unsubstituted or substituted heteroaryl, unsubstituted or substituted arylalkyl, unsubstituted or substituted cycloalkyl, unsubstituted or substituted alkyl, unsubstituted or substituted cycloalkylalkyl, and unsubstituted or substituted heteroarylalkyl group; wherein there are 1 to 6 substituents on the substituted $R^{12}$ groups and each substituent is independently selected from the group consisting of: $R^9$ groups;

each $R^{13}$ and $R^{14}$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, unsubstituted or substituted heterocyclic, unsubstituted or substituted fluoroalkyl, and unsubstituted or substituted heterocycloalkylalkyl (wherein "heterocyloalkyl" means heterocyclic); wherein there are 1 to 6 substituents on said substituted $R^{13}$ and $R^{14}$ groups and each substituent is independently selected from the group consisting of: alkyl, —$CF_3$, —OH, alkoxy, aryl, arylalkyl, fluroalkyl, cycloalkyl, cycloalkylalkyl, heteroaryl, heteroarylalkyl, —$N(R^{40})_2$, —$C(O)OR^{15}$, —$C(O)NR^{15}R^{16}$, —$S(O)_tNR^{15}R^{16}$, —$C(O)R^{15}$, —$SO_2R^{15}$ provided that $R^{15}$ is not H, halogen, and —$NHC(O)NR^{15}R^{16}$; or $R^{13}$ and $R^{14}$ taken together with the nitrogen they are attached to in the groups —$C(O)NR^{13}R^{14}$ and —$SO_2NR^{13}R^{14}$ form an unsubstituted or substituted saturated heterocyclic ring (preferably a 3 to 7 membered heterocyclic ring), said ring optionally containing one additional heteroatom selected from the group consisting of: O, S and $NR^{18}$; wherein there are 1 to 3 substituents on the substituted cyclized $R^{13}$ and $R^{14}$ groups (i.e., there is 1 to 3 substituents on the ring formed when the $R^{13}$ and $R^{14}$ groups are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —$C(O)OR^{15}$, —$C(O)NR^{15}R^{16}$, —$SO_tNR^{15}R^{16}$, —$C(O)R^{15}$, —$SO_2R^{15}$ provided that $R^{15}$ is not H, —$NHC(O)NR^{15}R^{16}$, —$NHC(O)OR^{15}$, halogen, and a heterocycloalkenyl group (i.e., a heterocyclic group that has at least one, and preferably one, double bond in a ring, e.g.,

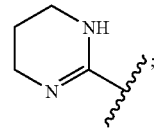

each $R^{15}$ and $R^{16}$ is independently selected from the group consisting of: H, alkyl, aryl, arylalkyl, cycloalkyl and heteroaryl;

$R^{17}$ is selected from the group consisting of: —$SO_2$alkyl, —$SO_2$aryl, —$SO_2$cycloalkyl, and —$SO_2$heteroaryl;

$R^{18}$ is selected from the group consisting of: H, alkyl, aryl, heteroaryl, —$C(O)R^{19}$, —$SO_2R^{19}$ and —$C(O)NR^{19}R^{20}$;

each $R^{19}$ and $R^{20}$ is independently selected from the group consisting of: alkyl, aryl and heteroaryl;

$R^{30}$ is selected from the group consisting of: alkyl, cycloalkyl, —CN, —NO$_2$, or —SO$_2$R$^{15}$ provided that $R^{15}$ is not H;

each $R^{31}$ is independently selected from the group consisting of: unsubstituted alkyl, unsubstituted or substituted aryl, unsubstituted or substituted heteroaryl and unsubstituted or substituted cycloalkyl; wherein there are 1 to 6 substituents on said substituted $R^{31}$ groups and each substituent is independently selected from the group consisting of: alkyl, halogen and —CF$_3$;

each $R^{40}$ is independently selected from the group consisting of: H, alkyl and cycloalkyl;

g is 1 or 2; and t is 0, 1 or 2.

For compounds of formula (I), when $R^3$ is —SO$_{(t)}$NR$^{13}$R$^{14}$ (e.g., —SO$_2$NR$^{13}$R$^{14}$), preferably $R^{13}$ and $R^{14}$ are independently selected from the group consisting of: H and alkyl (e.g., methyl, ethyl, isopropyl and t-butyl). Examples include, but are not limited to (1) —SO$_2$NH$_2$ and (2) —SO$_2$NR$^{13}$R$^{14}$ wherein $R^{13}$ and $R^{14}$ are the same or different alkyl group (e.g., methyl, ethyl, isopropyl and t-butyl), e.g., the same alkyl group, such as, for example —SO$_2$N(CH$_3$)$_2$.

For compounds of formula (I), when $R^3$ is —C(O)NR$^{13}$R$^{14}$, preferably $R^{13}$ and $R^{14}$ are independently selected from the group consisting of: H and alkyl (e.g., methyl, ethyl, isopropyl and t-butyl). Examples include, but are not limited to —C(O)NR$^{13}$R$^{14}$ wherein each $R^{13}$ and $R^{14}$ are the same or different alkyl group, e.g., the same alkyl group, such as, for example —C(O)N(CH$_3$)$_2$.

For the compounds of formula (I) substituent A is preferably selected from the group consisting of:

(1) unsubstituted or substituted:

[structures with R$_7$, R$_8$, R$_9$, R$_{8a}$ substituents]

(2)

[structure with R$_7$, R$_8$, R$_{8a}$]

wherein all substitutents are as defined for formula (I).

Examples of substituent A in formula (I) include, but are not limited to:

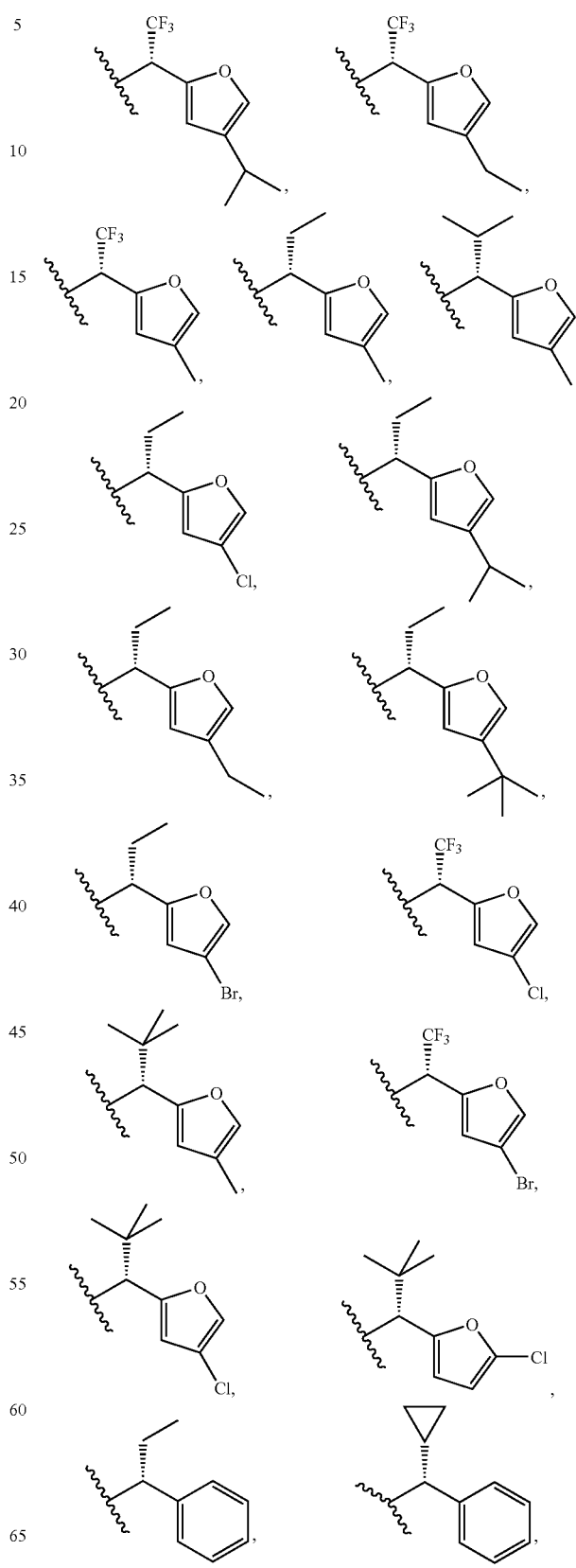

-continued
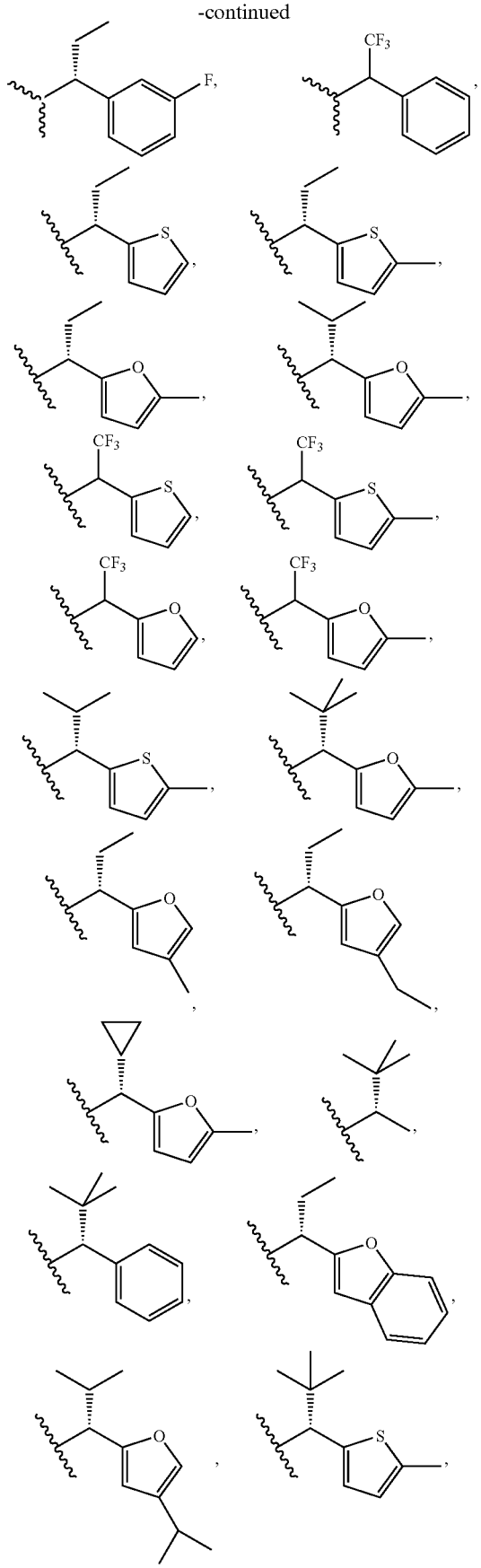
-continued
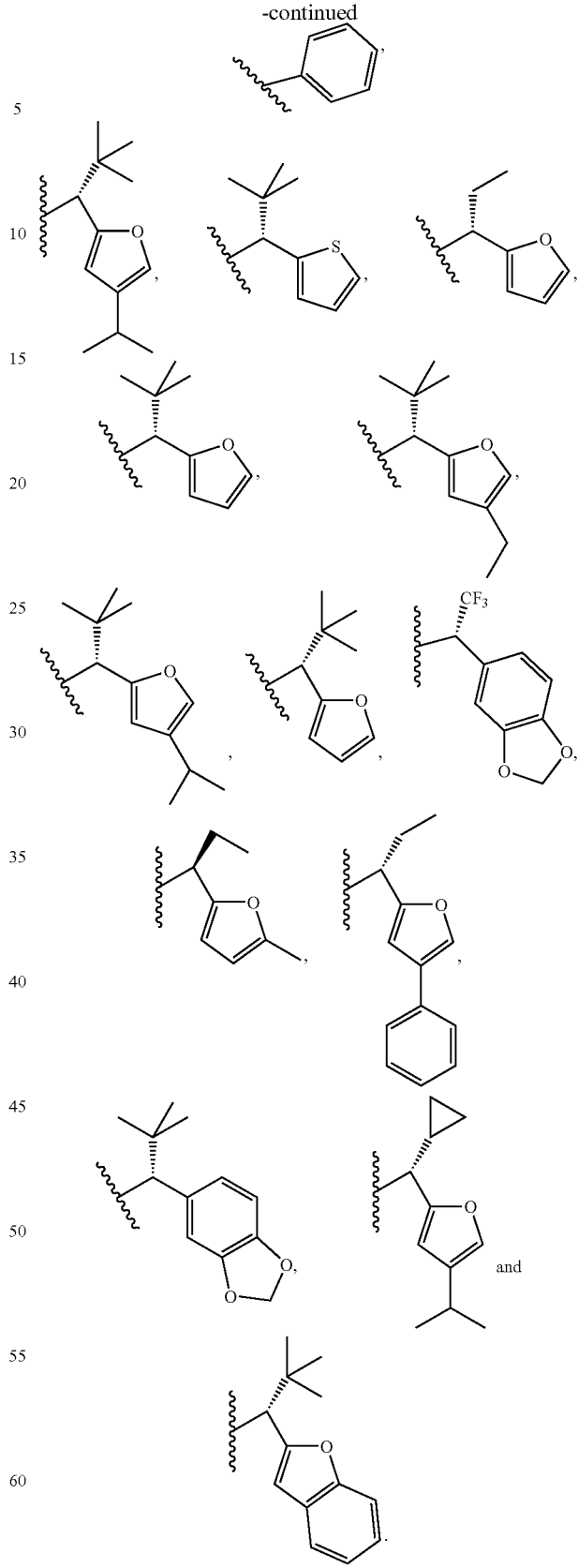
Substituent A in formula (I) is most preferably selected from the group consisting of:

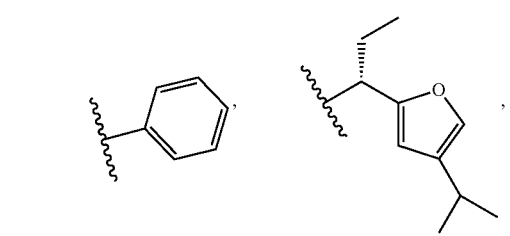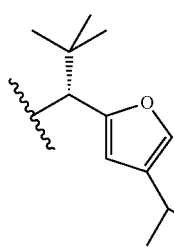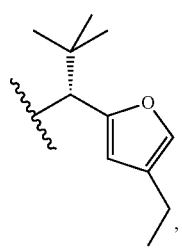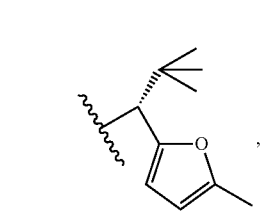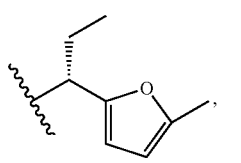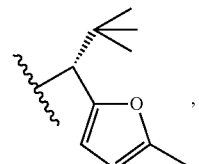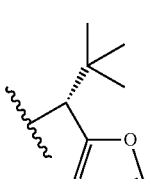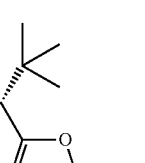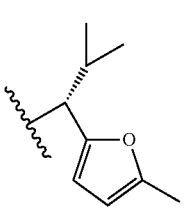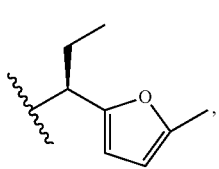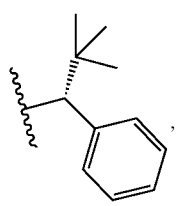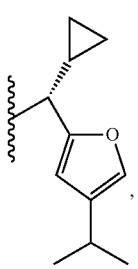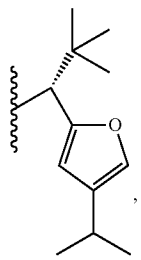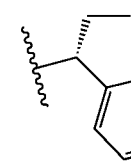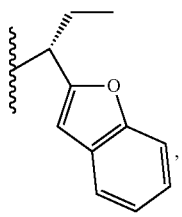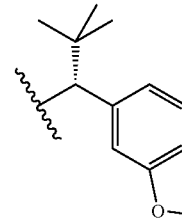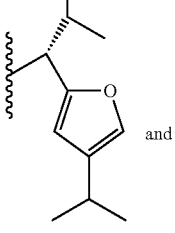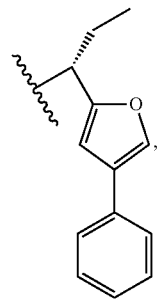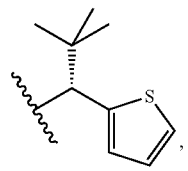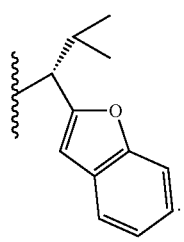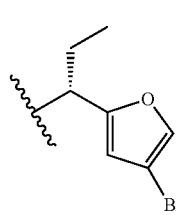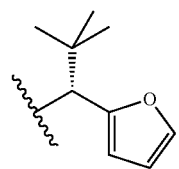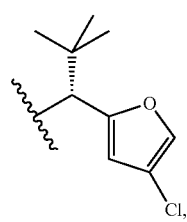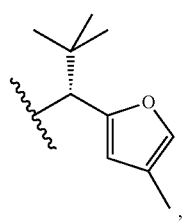
and
Substituent A in formula (I) is more preferably selected from the group consisting of:
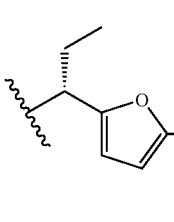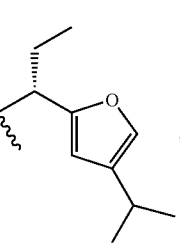

-continued

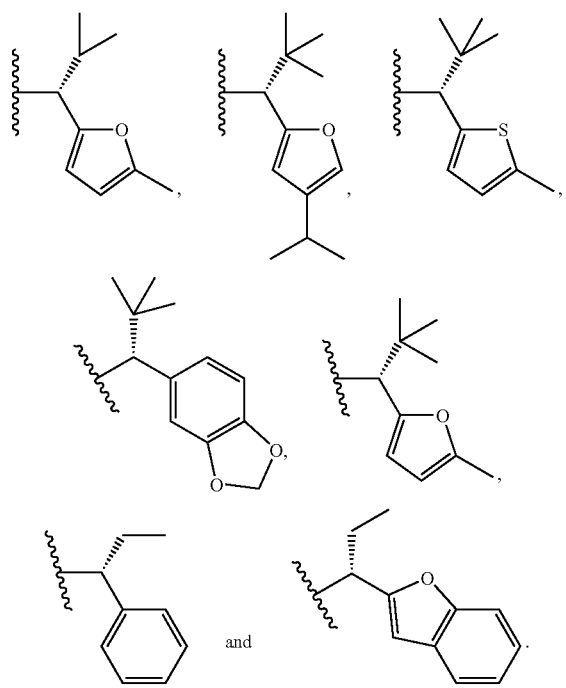

Substituent B in formula (I) is preferably selected from the group consisting of:

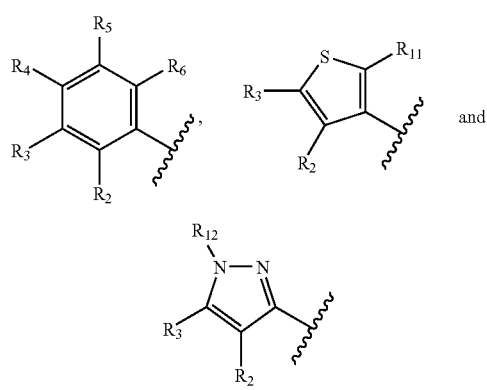

wherein all substituents are as defined for formula (I).

Substituent B in formula (I) is most preferably selected from the group consisting of:

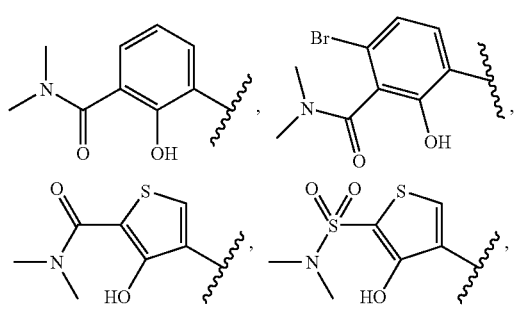

-continued

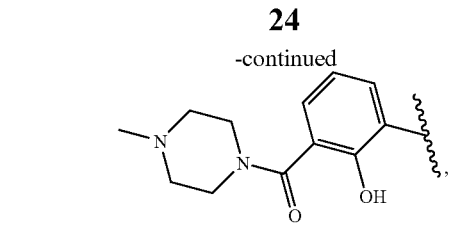

Substituent B in Formula (I) is more preferably selected from the group consisting of:

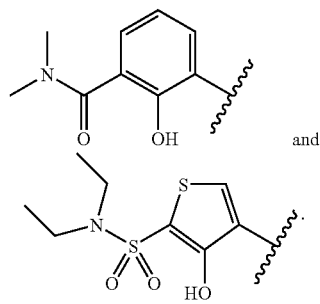

Compounds of formula (I) useful in the methods of this invention are described in the embodiments below. The embodiments have been numbered for purposes of reference thereto.

Embodiment No. 1 is directed to the methods of this invention using compounds of formula (I) wherein B is:

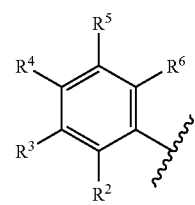

and all other substitutents are as defined for of formula (I).
Embodiment No. 2 is directed to the methods of this invention using compounds of formula (I) wherein B is:

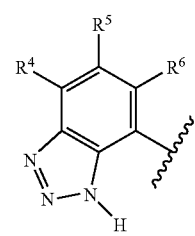

and all other substitutents are as defined for of formula (I).
Embodiment No. 3 is directed to the methods of this invention using compounds of formula (I) wherein B is:

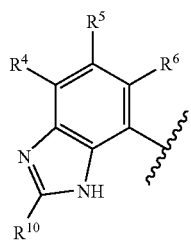

and all other substitutents are as defined for of formula (I).

Embodiment No. 4 is directed to the methods of this invention using compounds of formula (I) wherein B is:

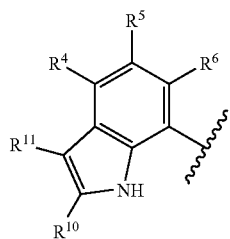

and all other substitutents are as defined for of formula (I).

Embodiment No. 5 is directed to the methods of this invention using compounds of formula (I) wherein B is:

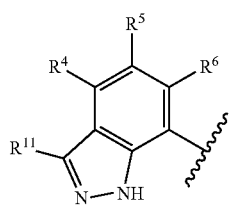

and all other substitutents are as defined for of formula (I).

Embodiment No. 6 is directed to the methods of this invention using compounds of formula (I) wherein B is:

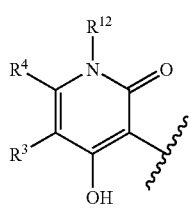

and all other substitutents are as defined for of formula (I).

Embodiment No. 7 is directed to the methods of this invention using compounds of formula (I) wherein B is:

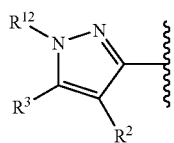

and all other substitutents are as defined for of formula (I).

Embodiment No. 8 is directed to the methods of this invention using compounds of formula (I) wherein B is:

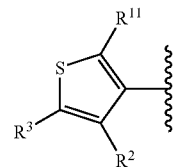

and all other substitutents are as defined for of formula (I).

Embodiment No. 9 is directed to the methods of this invention using compounds of formula (I) wherein B is:

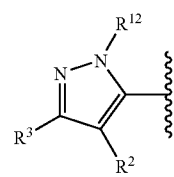

and all other substitutents are as defined for of formula (I).

Embodiment No. 10 is directed to the methods of this invention using compounds of formula (I) wherein B is:

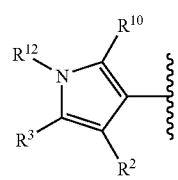

and all other substitutents are as defined for of formula (I).

Embodiment No. 11 is directed to the methods of this invention using compounds of formula (I) wherein B is:

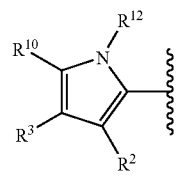

and all other substitutents are as defined for of formula (I).

Embodiment No. 12 is directed to the methods of this invention using compounds of formula (I) wherein B is:

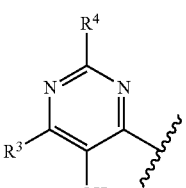

and all other substitutents are as defined for of formula (I).

Embodiment No. 13 is directed to the methods of this invention using compounds of formula (I) wherein B is:

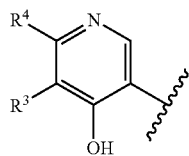

and all other substitutents are as defined for of formula (I).

Embodiment No. 14 is directed to the methods of this invention using compounds of formula (I) wherein B is:

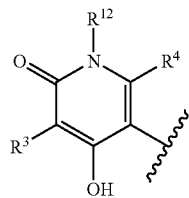

and all other substitutents are as defined for of formula (I).

Embodiment No. 15 is directed to the methods of this invention using compounds of formula (I) wherein B is:

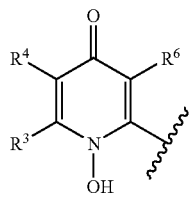

and all other substitutents are as defined for of formula (I).

Embodiment No. 16 is directed to the methods of this invention using compounds of formula (I) wherein B is:

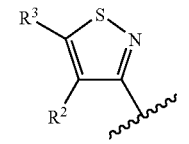

and all other substitutents are as defined for of formula (I).

Embodiment No. 17 is directed to the methods of this invention using compounds of formula (I) wherein B is:

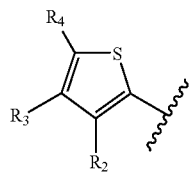

and all other substitutents are as defined for of formula (I).

Embodiment No. 18 is directed to the methods of this invention using compounds of formula (I) wherein B is:

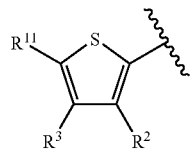

and all other substitutents are as defined for of formula (I).

Embodiment No. 19 is directed to the methods of this invention using compounds of formula (I) wherein B is selected from the group consisting of:

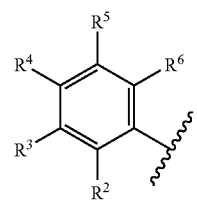

(1)

and $R^3$ for this B group is selected from the group consisting of: —$C(O)NR^{13}R^{14}$,

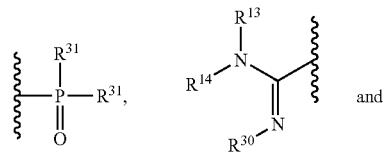
and
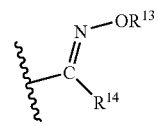

and all other substituents are as defined for formula (I).

Embodiment No. 20 is directed to the methods of this invention using compounds of formula (I) wherein B is:

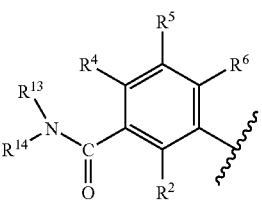

and all other substitutents are as defined in formula (I).

Embodiment No. 21 is directed to the methods of this invention using compounds of formula (I) wherein B is

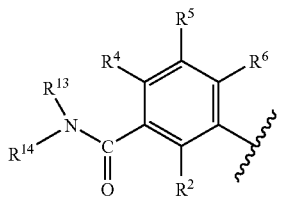

$R^{13}$ and $R^{14}$ are independently selected from the group consisting of H and alkyl (e.g., methyl, ethyl, isopropyl and t-butyl), and all other substituents are as defined in formula (I).

Embodiment No. 22 is directed to the methods of this invention using compounds of formula (I) wherein B is

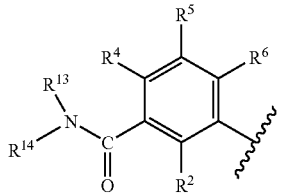

wherein:
(1) $R^2$ is —OH and all other substituents are as defined in formula (I), or
(2) $R^2$ is —OH, and $R^{13}$ and $R^{14}$ are independently selected from the group, consisting of: H and alkyl (e.g., methyl, ethyl, isopropyl and t-butyl), or
(3) $R^2$ is —OH, and $R^{13}$ and $R^{14}$ are the same or different and alkyl group (e.g., methyl, ethyl, isopropyl and t-butyl), for example the same alkyl group, for example methyl, and
(4) and all other substituents are as defined in formula (I).

Embodiment No. 23 is directed to the methods of this invention using compounds of formula (I) wherein B is

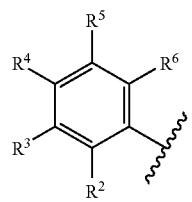

$R^3$ is selected from the group consisting of:

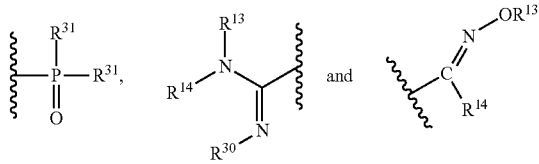

and all other substituents are as defined in formula (I).

Embodiment No. 24 is directed to the methods of this invention using compounds of formula (I) wherein B is

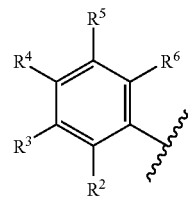

$R^3$ is selected from the group consisting of:

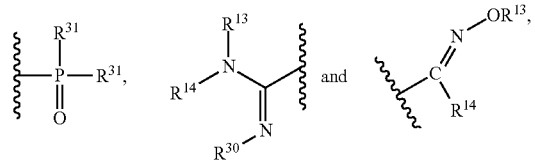

$R^2$ is —OH, and all other substituents are as defined in formula (I).

Embodiment No. 25 is directed to the methods of this invention using compounds of formula (I) wherein B is:

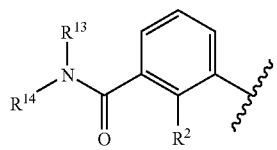

and all other substituents are as defined in formula (I)

Embodiment No. 26 is directed to the methods of this invention using compounds of formula (I) wherein B is:

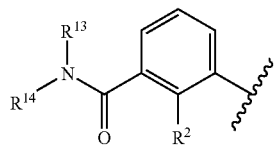

$R^2$ is —OH, and all other substituents are as defined in formula (I).

Embodiment No. 27 is directed to the methods of this invention using compounds of formula (I) wherein B is:

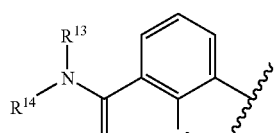

$R^2$ is as defined for compounds of formula (I), $R^{13}$ and $R^{14}$ are independently selected from the group consisting of H and alkyl (e.g., methyl, ethyl, isopropyl and t-butyl), and all other substituents areas defined for compounds of formula (I). For example, $R^{13}$ and $R^{14}$ are the same or different alkyl group. Also, for example, $R^{13}$ and $R^{14}$ are the same alkyl group. Also, for example, $R^{13}$ and $R^{14}$ are methyl.

Embodiment No. 28 is directed to the methods of this invention using compounds of formula (I) wherein B is:

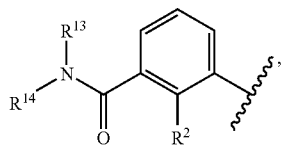

$R^2$ is —OH, $R^{13}$ and $R^{14}$ are independently selected from the group consisting of H and alkyl (e.g., methyl, ethyl, isopropyl and t-butyl), and all other substituents areas defined for compounds of formula (I). For example, $R^{13}$ and $R^{14}$ are the same or different alkyl group. Also, for example, $R^{13}$ and $R^{14}$ are the same alkyl group. Also, for example, $R^{13}$ and $R^{14}$ are methyl.

Embodiment No. 29 is directed to the methods of this invention using compounds of formula (I) wherein B is as described in Embodiment No. 23, $R^4$ is H, $R^5$ is H, $R^6$ is H, and all other substituents are as defined for compounds of formula (I).

Embodiment No. 30 is directed to the methods of this invention using compounds of formula (I) wherein B is as described in Embodiment No. 24, $R^4$ is H, $R^5$ is H, $R^6$ is H, and all other substituents areas defined for compounds of formula (I).

Embodiment No. 31 is directed to the methods of this invention using compounds of formula (I) wherein B is as described in Embodiments Nos. 21, 22, 25 and 26, except that $R^{13}$ and $R^{14}$ are each methyl, and all other substituents are as defined in formula (I).

Embodiment No. 32 is directed to the methods of this invention using compounds of formula (I) wherein B is:

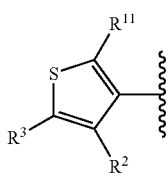

$R^{11}$ is H, and all other substituents are as defined in formula (I).

Embodiment No. 33 is directed to the methods of this invention using compounds of formula (I) wherein B is:

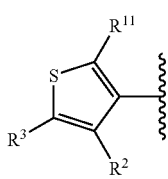

$R^2$ is —OH, and all other substituents are as defined in formula (I).

Embodiment No. 34 is directed to the methods of this invention using compounds of formula (I) wherein B is:

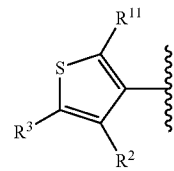

$R^3$ is —C(O)NR$^{13}$R$^{14}$, and all other substituents are as defined in formula (I).

Embodiment No. 35 is directed to the methods of this invention using compounds of formula (I) wherein B is:

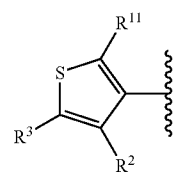

$R^3$ is —S(O)$_t$NR$^{13}$R$^{14}$ (e.g., t is 2), and all other substituents are as defined in formula (I).

Embodiment No. 36 is directed to the methods of this invention using compounds of formula (I) wherein B is:

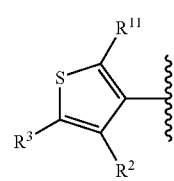

$R^2$ is —OH, $R^3$ is —C(O)NR$^{13}$R$^{14}$, and all other substituents are as defined in formula (I).

Embodiment No. 37 of this invention is directed to the methods of this invention using compounds of formula (I) wherein B is:

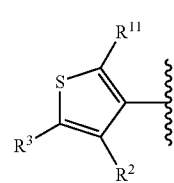

$R^2$ is —OH, and $R^3$ is —S(O)$_t$NR$^{13}$R$^{14}$ (e.g., t is 2), and all other substituents are as defined in formula (I).

Embodiment No. 38 is directed to the methods of this invention using compounds of formula (I) wherein B is:

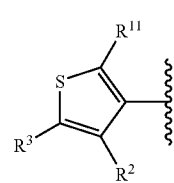

$R^2$ is —OH, $R^3$ is —C(O)NR$^{13}$R$^{14}$, $R^{11}$ is H, and all other substituents are as defined in formula (I).

Embodiment No. 39 is directed to the methods of this invention using compounds of formula (I) wherein B is:

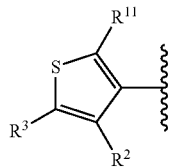

$R^2$ is —OH, $R^3$ is —S(O)$_t$NR$^{13}$R$^{14}$ (e.g., t is 2), $R^{11}$ is H, and all other substituents are as defined in formula (I).

Embodiment No. 40 is directed to the methods of this invention using compounds of formula (I) wherein B is:

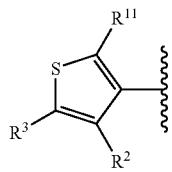

$R^2$ is —OH, $R^3$ is —C(O)NR$^{13}$R$^{14}$, $R^{11}$ is H, and $R^{13}$ and $R^{14}$ are independently selected from the group consisting of: H, alkyl (e.g., methyl, ethyl, isopropyl and t-butyl), unsubstituted heteroaryl and substituted heteroaryl, and all other substituents are as defined in formula (I). For example, one of $R^{13}$ or $R^{14}$ is alkyl (e.g., methyl). An example of a substituted heteroaryl group is

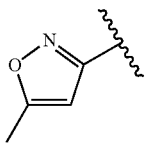

Embodiment No. 41 is directed to the methods of this invention using compounds of formula (I) wherein B is:

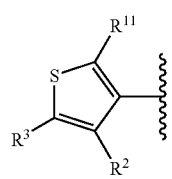

$R^2$ is —OH, $R^3$ is —S(O)$_t$NR$^{13}$R$^{14}$ (e.g., t is 2), $R^{11}$ is H, and $R^{13}$ and $R^{14}$ are independently selected from the group consisting of: H and alkyl (e.g., methyl, ethyl, isopropyl, and t-butyl), and all other substituents are as defined in formula (I). For example $R^3$ is (1) —SO$_2$NH$_2$ and (2) —SO$_2$NR$^{13}$R$^{14}$ wherein $R^{13}$ and $R^{14}$ are the same or different alkyl group (e.g., methyl, ethyl, isopropyl and t-butyl), e.g., the same alkyl group, such as, for example —SO$_2$N(CH$_3$)$_2$.

Embodiment No. 42 is directed to the methods of this invention using compounds of formula (I) wherein B is:

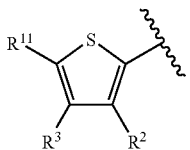

$R^{11}$ is H, and all other substituents are as defined in formula (I).

Embodiment No. 43 is directed to the methods of this invention using compounds of formula (I) wherein B is:

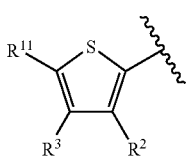

$R^2$ is —OH, and all other substituents are as defined in formula (I).

Embodiment No. 44 is directed to the methods of this invention using compounds of formula (I) wherein B is:

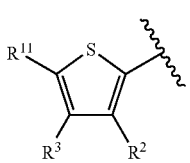

$R^3$ is —C(O)NR$^{13}$R$^{14}$, and all other substituents are as defined in formula (I).

Embodiment No. 45 is directed to the methods of this invention using compounds of formula (I) wherein B is:

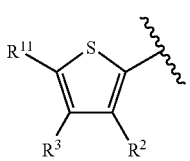

$R^3$ is —S(O)$_t$NR$^{13}$R$^{14}$ (e.g., t is 2), and all other substituents are as defined in formula (I).

Embodiment No. 46 is directed to the methods of this invention using compounds of formula (I) wherein B is:

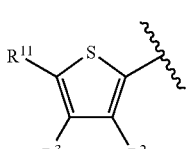

$R^2$ is —OH, $R^3$ is —C(O)NR$^{13}$R$^{14}$, and all other substituents are as defined in formula (I).

Embodiment No. 47 is directed to the methods of this invention using compounds of formula (I) wherein B is:

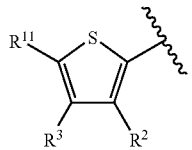

$R^2$ is —OH, and $R^3$ is —S(O)$_t$NR$^{13}$R$^{14}$ (e.g., t is 2), and all other substituents are as defined in formula (I).

Embodiment No. 48 is directed to the methods of this invention using compounds of formula (I) wherein B is:

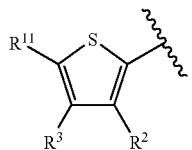

$R^2$ is —OH, $R^3$ is —C(O)NR$^{13}$R$^{14}$, $R^{11}$ is H, and all other substituents are as defined in formula (I).

Embodiment No. 49 is directed to the methods of this invention using compounds of formula (I) wherein B is:

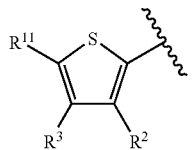

$R^2$ is —OH, $R^3$ is —S(O)$_t$NR$^{13}$R$^{14}$ (e.g., t is 2), $R^{11}$ is H, and all other substituents are as defined in formula (I).

Embodiment No. 50 is directed to the methods of this invention using compounds of formula (I) wherein B is:

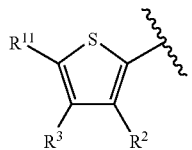

$R^2$ is —OH, $R^3$ is —C(O)NR$^{13}$R$^{14}$, $R^{11}$ is H, and $R^{13}$ and $R^{14}$ are independently selected from the group consisting of: alkyl, unsubstituted heteroaryl and substituted heteroaryl, and all other substituents are as defined in formula (I). For example, one of $R^{13}$ or $R^{14}$ is alkyl (e.g., methyl). An example of a substituted heteroaryl group is

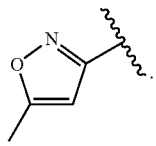

Embodiment No. 51 is directed to the methods of this invention using compounds of formula (I) wherein B is:

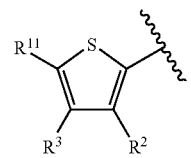

$R^2$ is —OH, $R^3$ is —S(O)$_t$NR$^{13}$R$^{14}$ (e.g., t is 2), $R^{11}$ is H, $R^{13}$ and $R^{14}$ are independently selected from the group consisting of: H and alkyl (e.g., methyl, ethyl, isopropyl, and t-butyl), and all other substituents are as defined in formula (I). For example $R^3$ is (1) —SO$_2$NH$_2$ and (2) —SO$_2$NR$^{13}$R$^{14}$ wherein $R^{13}$ and $R^{14}$ are the same or different alkyl group (e.g., methyl, ethyl, isopropyl and t-butyl), e.g., the same alkyl group, such as, for example —SO$_2$N(CH$_3$)$_2$.

Embodiment No. 52 is directed to the methods of this invention using compounds of formula (I) wherein substituent B is selected from the group consisting of:

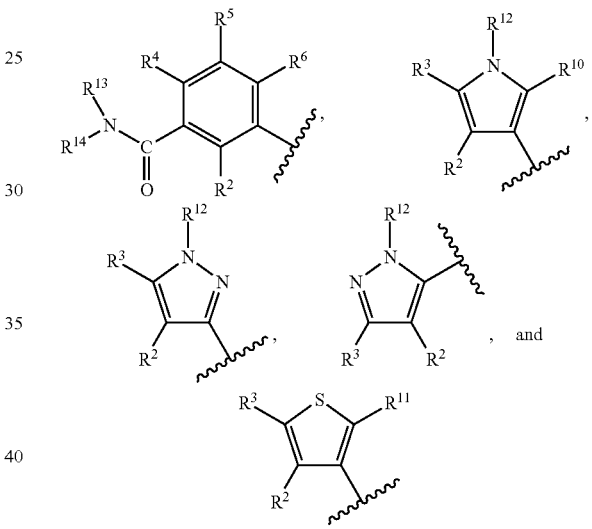

wherein $R^2$ to $R^6$ and $R^{10}$ to $R^{14}$ are as defined above for the compounds of formula (I).

Embodiment No. 53 is directed to the methods of this invention using compounds of formula (I) wherein substituent B is selected from the group consisting of:

-continued

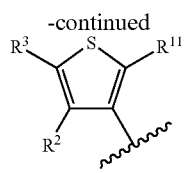

wherein
R² is selected from the group consisting of: H, OH, —NHC(O)R¹³ or and —NHSO₂R¹³;
R³ is selected from the group consisting of: —SO₂NR¹³R¹⁴, —NO₂, cyano, —C(O)NR¹³R¹⁴, —SO₂R¹³; and —C(O)OR¹³;
R⁴ is selected from the group consisting of: H, —NO₂, cyano, —CH₃, halogen, and —CF₃;
R⁵ is selected from the group consisting of: H, —CF₃, —NO₂, halogen and cyano;
R⁶ is selected from the group consisting of: H, alkyl and —CF₃;
each R¹⁰ and R¹¹ is independently selected from the group consisting of: R¹³, hydrogen, halogen, —CF₃, —NR¹³R¹⁴, —NR¹³C(O)NR¹³R¹⁴, —C(O)OR¹³, —SH, —SO₍ₜ₎NR¹³R¹⁴, —SO₂R¹³, —NHC(O)R¹³, —NHSO₂NR¹³R¹⁴, —NHSO₂R¹³, —C(O)NR¹³R¹⁴, —C(O)NR¹³OR¹⁴, —OC(O)R¹³, —COR¹³, —OR¹³, and cyano;
each R¹³ and R¹⁴ is independently selected from the group consisting of: H, methyl, ethyl and isopropyl; or
R¹³ and R¹⁴ when taken together with the nitrogen they are attached to in the groups —NR¹³R¹⁴, —C(O)NR¹³R¹⁴, —SO₂NR¹³R¹⁴, —OC(O)NR¹³R¹⁴, —CONR¹³R¹⁴, —NR¹³C(O)NR¹³R¹⁴, —SO₍ₜ₎NR¹³R¹⁴, —NHSO₂NR¹³R¹⁴ form an unsubstituted or substituted saturated heterocyclic ring (preferably a 3 to 7 membered ring) optionally having one additional heteroatom selected from the group consisting of: O, S or NR¹⁸; wherein R¹⁸ is selected from the group consisting of: H, alkyl, aryl, heteroaryl, —C(O)R¹⁹, —SO₂R¹⁹ and —C(O)NR¹⁹R²⁰; wherein each R¹⁹ and R²⁰ is independently selected from the group consisting of: alkyl, aryl and heteroaryl; wherein there are 1 to 3 substituents on the substituted cyclized R¹³ and R¹⁴ groups (i.e., the substituents on the ring formed when R¹³ and R¹⁴ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR¹⁵, —C(O)NR¹⁵R¹⁶, —SO₍ₜ₎NR¹⁵R¹⁶, —C(O)R¹⁵, —SO₂R¹⁵ provided that R¹⁵ is not H, —NHC(O)NR¹⁵R¹⁶ and halogen; and wherein each R¹⁵ and R¹⁶ is independently selected from the group consisting: of H, alkyl, aryl, arylalkyl, cycloalkyl and heteroaryl.

Embodiment No. 54 is directed to the methods of this invention using compounds of formula (I) wherein substituent B is selected from the group consisting of:

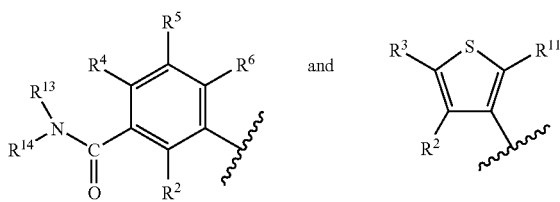

wherein:
R² is selected from the group consisting of: H, OH, —NHC(O)R¹³ and —NHSO₂R¹³;
R³ is selected from the group consisting of: —C(O)NR¹³R¹⁴, —SO₂NR¹³R¹⁴, —NO₂, cyano, —SO₂R¹³; and —C(O)OR¹³;
R⁴ is selected from the group consisting of: H, —NO₂, cyano, —CH₃ or —CF₃;
R⁵ is selected from the group consisting of: H, —CF₃, —NO₂, halogen and cyano; and
R⁶ is selected from the group consisting of: H, alkyl and —CF₃;
R¹¹ is selected from the group consisting of: H, halogen and alkyl; and
each R¹³ and R¹⁴ is independently selected from the group consisting of: H, methyl, ethyl and isopropyl; or
R¹³ and R¹⁴ when taken together with the nitrogen they are attached to in the groups —NR¹³R¹⁴, —C(O)NR¹³R¹⁴, —SO₂NR¹³R¹⁴, —OC(O)NR¹³R¹⁴, —CONR¹³R¹⁴, —NR¹³C(O)NR¹³R¹⁴, —SO₍ₜ₎NR¹³R¹⁴, —NHSO₂NR¹³R¹⁴ form an unsubstituted or substituted saturated heterocyclic ring (preferably a 3 to 7 membered ring) optionally having one additional heteroatom selected from O, S or NR¹⁸ wherein R¹⁸ is selected from H, alkyl, aryl, heteroaryl, —C(O)R¹⁹, —SO₂R¹⁹ and —C(O)NR¹⁹R²⁰, wherein each R¹⁹ and R²⁰ is independently selected from alkyl, aryl and heteroaryl, wherein there are 1 to 3 substituents on the substituted cyclized R¹³ and R¹⁴ groups (i.e., on the ring formed when R¹³ and R¹⁴ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR¹⁵, —C(O)NR¹⁵R¹⁶, —SO₍ₜ₎NR¹⁵R¹⁶, —C(O)R¹⁵, —SO₂R¹⁵ provided that R¹⁵ is not H, —NHC(O)NR¹⁵R¹⁶ and halogen; and wherein each R¹⁵ and R¹⁶ is independently selected from the group consisting of: H, alkyl, aryl, arylalkyl, cycloalkyl and heteroaryl.

Embodiment No. 55 is directed to the methods of this invention using compounds of formula (I) wherein substituent B is selected from the group consisting of:

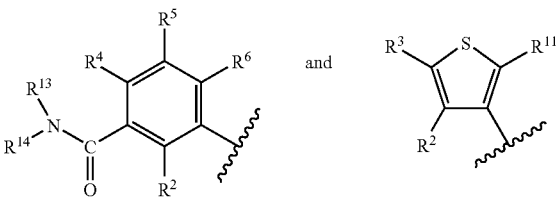

wherein:
R² is selected from the group consisting of: H, OH, —NHC(O)R¹³ and —NHSO₂R¹³;
R³ is selected from the group consisting of: —C(O)NR¹³R¹⁴—SO₂NR¹³R¹⁴, —NO₂, cyano, and —SO₂R¹³;
R⁴ is selected from the group consisting of: H, —NO₂, cyano, —CH₃ or —CF₃;
R⁵ is selected from the group consisting of: H, —CF₃, —NO₂, halogen and cyano; and
R⁶ is selected from the group consisting of: H, alkyl and —CF₃;
R¹¹ is selected from the group consisting of: H, halogen and alkyl; and
each R¹³ and R¹⁴ is independently selected from the group consisting of: H, methyl and ethyl.

Embodiment No. 56 is directed to the methods of this invention using compounds of formula (I) wherein substituent B is selected from the group consisting of:

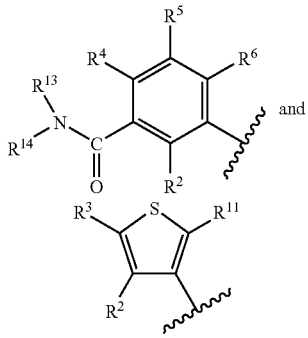

wherein:

R² is —OH;
R³ is selected from the group consisting of: —SO₂NR¹³R¹⁴ and —CONR¹³R¹⁴;
R⁴ is selected form the group consisting of: H, —CH₃ and —CF₃;
R⁵ is selected from the group consisting of: H and cyano;
R⁶ is selected from the group consisting of: H, —CH₃ and —CF₃;
R¹¹ is H; and
R¹³ and R¹⁴ are independently selected from the group consisting of H and methyl (e.g., for —SO₂NR¹³R¹⁴ both R¹³ and R¹⁴ are H, or both R¹³ and R¹⁴ are methyl, also, for example, for —CONR¹³R¹⁴ both R¹³ and R¹⁴ are methyl).

Embodiment No. 57 is directed to the methods of this invention using compounds of formula (I) wherein substituent B is selected from the group consisting of:

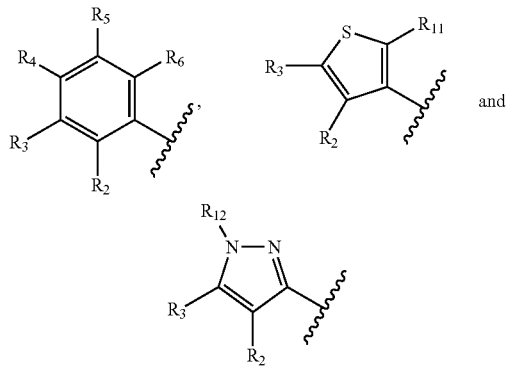

wherein all substituents are as defined for formula (I).

Embodiment No. 58 is directed to the methods of this invention using compounds of formula (I) wherein substituent B is selected from the group consisting of:

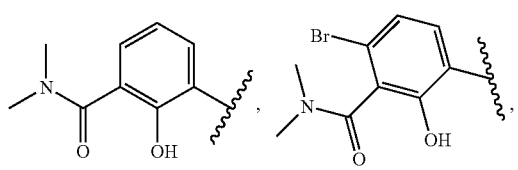

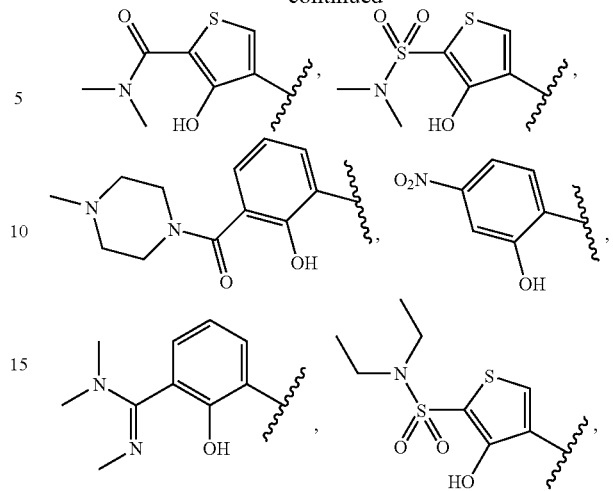

Embodiment No. 59 is directed to the methods of this invention using compounds of formula (I) wherein substituent B is selected from the group consisting of:

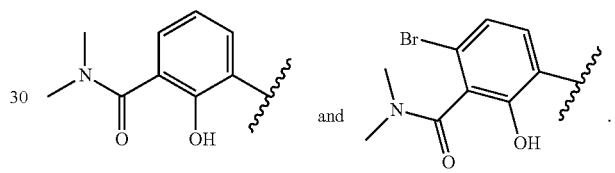

Embodiment No. 60 is directed to the methods of this invention using compounds of formula (I) wherein substituent A is selected from the group consisting of:

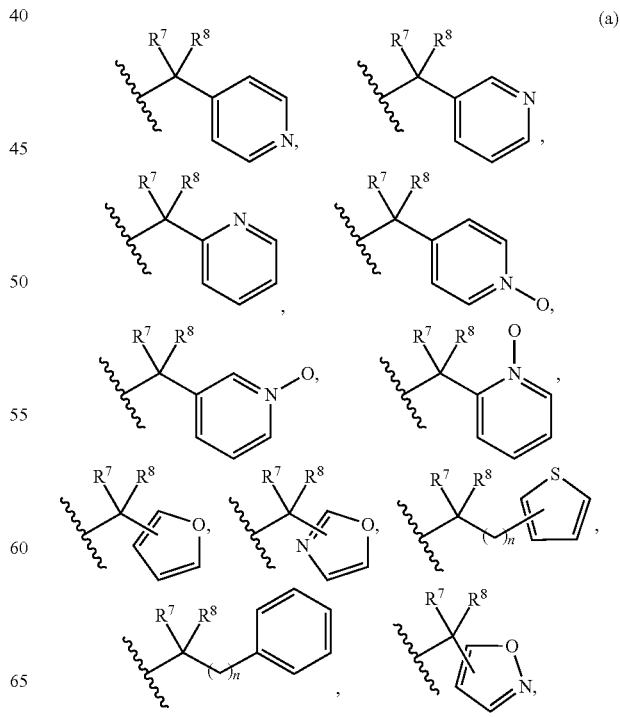

-continued

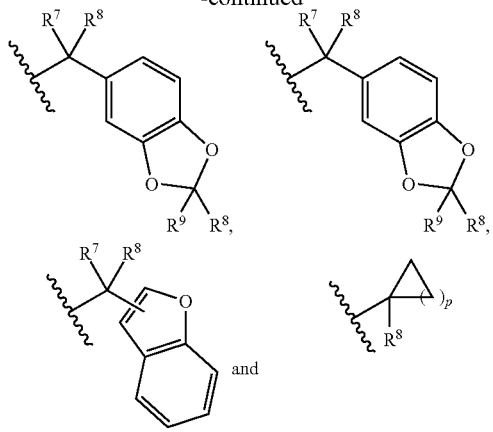

wherein the above rings are unsubstituted or substituted, as described for formula (I); and (b)

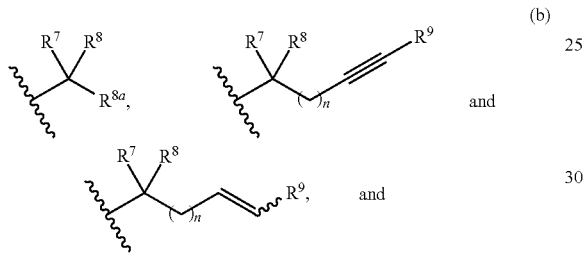

wherein in (a) and (b): each $R^7$ and $R^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, fluoroalkyl, alkynyl, alkenyl, and cycloalkenyl, wherein said substituents on said $R^7$ and $R^8$ substituted groups are selected from the group consisting of: a) cyano, b) —$CO_2R^{13}$, c) —$C(O)NR^{13}R^{14}$, d) —$SO_2NR^{13}R^{14}$, e) —$NO_2$, f) —$CF_3$, g) —$OR^{13}$, h) —$NR^{13}R^{14}$, i) —$OC(O)R^{13}$, j) —$OC(O)NR^{13}R^{14}$, and k) halogen; and $R^{8a}$ and $R^9$ are as defined in formula (I).

Embodiment No. 61 is directed to the methods of this invention using compounds of formula (I) wherein substituent A is selected from the group consisting of:

(a)

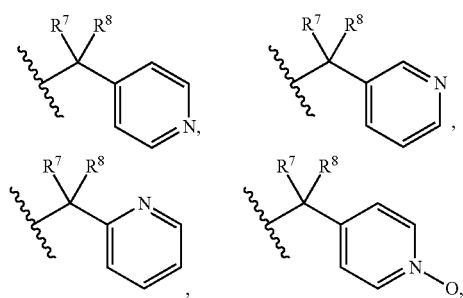

-continued

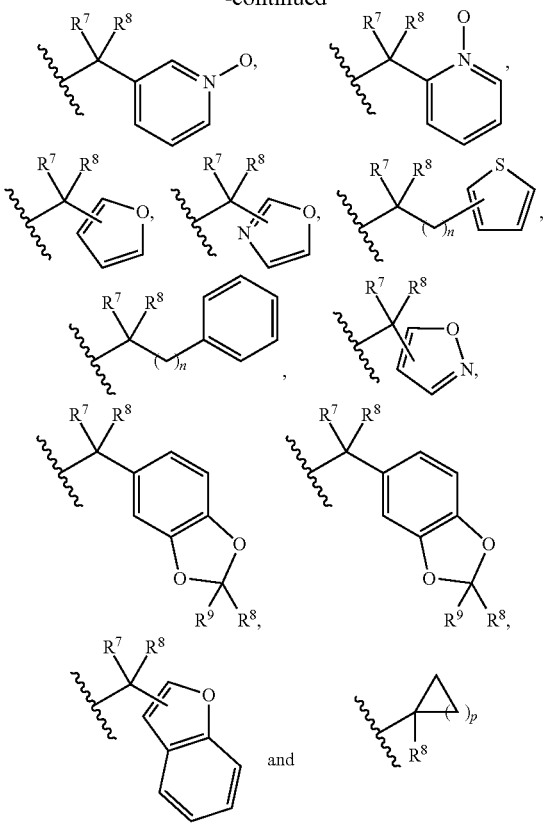

wherein the above rings are unsubstituted, or the above rings are substituted with 1 to 3 substituents independently selected from the group consisting of: halogen, alkyl, cycloalkyl, —$CF_3$, cyano, —$OCH_3$, and —$NO_2$; each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); and $R^9$ is selected from the group consisting of: H, halogen, alkyl, cycloalkyl, —$CF_3$, cyano, —$OCH_3$, and —$NO_2$; and (b)

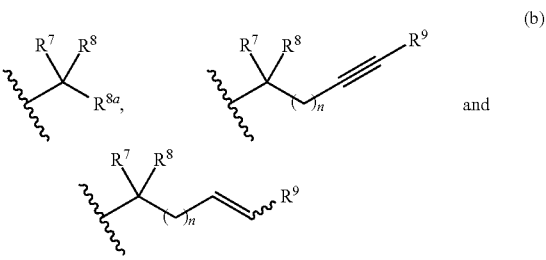

wherein each $R^7$ and $R^8$ is independently selected from the group consisting of: H, alkyl (e.g., methyl, ethyl, t-butyl, and isopropyl), fluoroalkyl (such as, —$CF_3$ and —$CF_2CH_3$), cycloalkyl (e.g., cyclopropyl, and cyclohexyl), and cycloalkylalkyl (e.g., cyclopropylmethyl); wherein $R^{8a}$ is as defined in formula (I), and wherein $R^9$ is selected from the group consisting of: H, halogen, alkyl, cycloalkyl, —$CF_3$, cyano, —$OCH_3$, and —$NO_2$; each $R^7$ and $R^8$ is independently selected from the group consisting of: H, alkyl (e.g., methyl, ethyl, t-butyl, and isopropyl), fluoroalkyl (such as, —$CF_3$ and —CF$_2$CH$_3$), cycloalkyl (e.g., cyclopropyl, and cyclohexyl), and cycloalkylalkyl (e.g., cyclopropylmethyl).

Embodiment No. 62 is directed to the methods of this invention using compounds of formula (I) wherein substituent A is selected from the group consisting of:

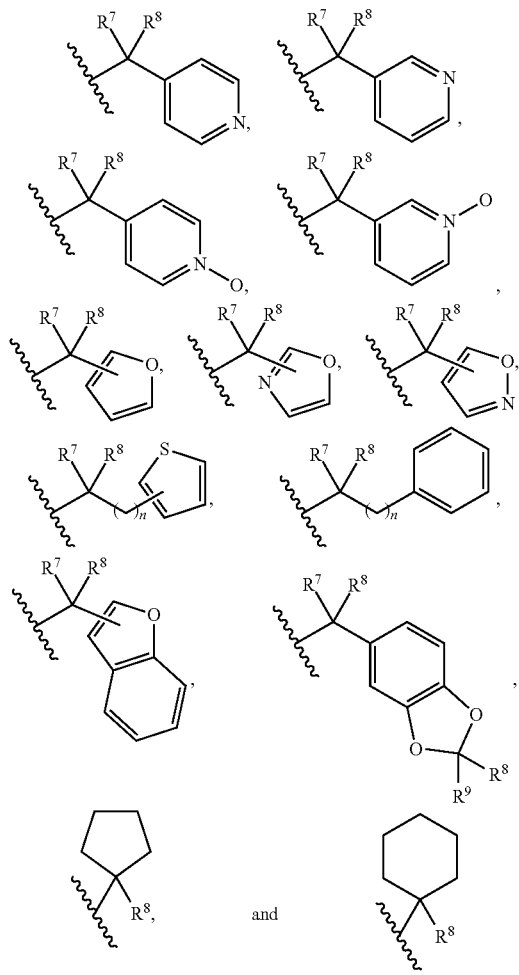

(a)

wherein the above rings are unsubstituted, or the above rings are substituted with 1 to 3 substituents independently selected from the group consisting of: H, F, Cl, Br, alkyl, cycloalkyl, and —CF$_3$; R$^7$ is selected from the group consisting of: H, fluoroalkyl, alkyl and cycloalkyl; R$^8$ is selected form the group consisting of: H, alkyl, —CF$_2$CH$_3$ and —CF$_3$; and R$^9$ is selected from the group consisting of: H, F, Cl, Br, alkyl or —CF$_3$; and

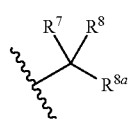

(b)

wherein R$^7$ is selected from the group consisting of: H, fluoroalkyl, alkyl and cycloalkyl; R$^8$ is selected form the group consisting of: H, alkyl, —CF$_2$CH$_3$ and —CF$_3$; and R$^{8a}$ is as defined for formula (I).

Embodiment No. 63 is directed to the methods of this invention using compounds of formula (I) wherein substituent A is selected from the group consisting of:

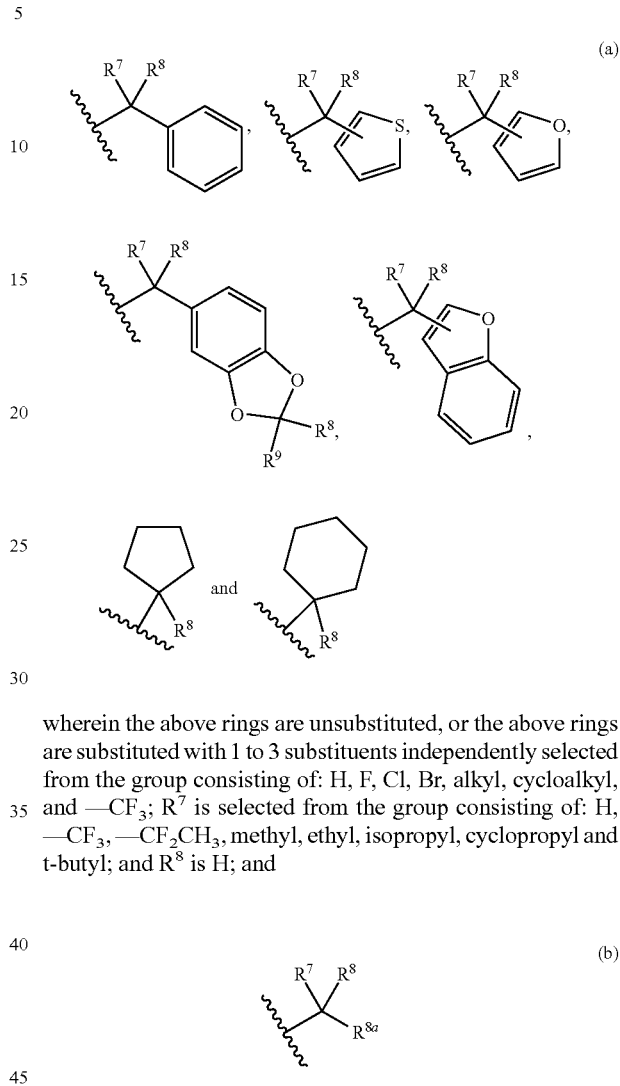

(a)

wherein the above rings are unsubstituted, or the above rings are substituted with 1 to 3 substituents independently selected from the group consisting of: H, F, Cl, Br, alkyl, cycloalkyl, and —CF$_3$; R$^7$ is selected from the group consisting of: H, —CF$_3$, —CF$_2$CH$_3$, methyl, ethyl, isopropyl, cyclopropyl and t-butyl; and R$^8$ is H; and (b)

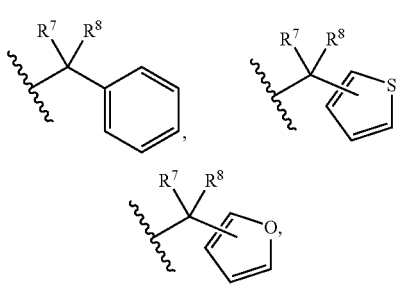

wherein R$^7$ is selected from the group consisting of: H, —CF$_3$, —CF$_2$CH$_3$, methyl, ethyl, isopropyl, cyclopropyl and t-butyl; and R$^8$ is H; and R$^{8a}$ is as defined for formula (I).

Embodiment No. 64 is directed to the methods of this invention using compounds of formula (I) wherein substituent A is selected from the group consisting of:

(a)

-continued

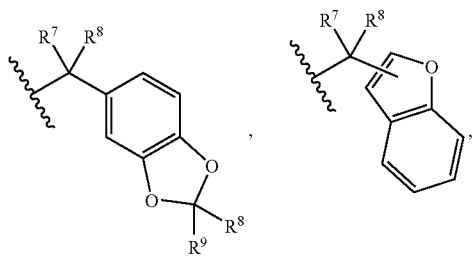

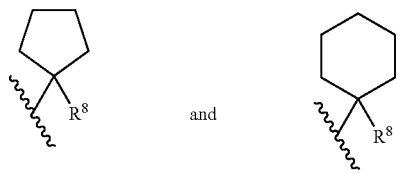

wherein the above rings are unsubstituted, or the above rings are substituted with 1 to 3 substituents independently selected from the group consisting of: F, Cl, Br, alkyl, cycloalkyl, and —CF$_3$; R$^7$ is selected from the group consisting of: H, —CF$_3$, —CF$_2$CH$_3$, methyl, ethyl, isopropyl, cyclopropyl and t-butyl; and R$^8$ is H; and (b)

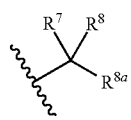

wherein R$^7$ is selected from the group consisting of: H, —CF$_3$, —CF$_2$CH$_3$, methyl, ethyl, isopropyl, cyclopropyl and t-butyl; and R$^8$ is H; and R$^{8a}$ is as defined for formula IA;

Embodiment No. 65 is directed compounds of formula (I) wherein substituent A is selected from the group consisting of:

(1) unsubstituted or substituted:

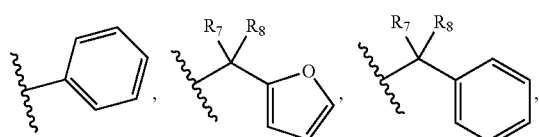

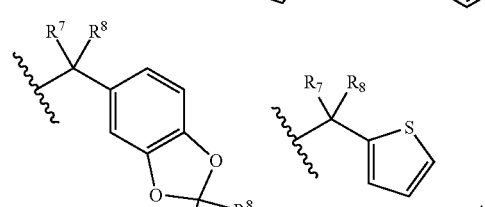

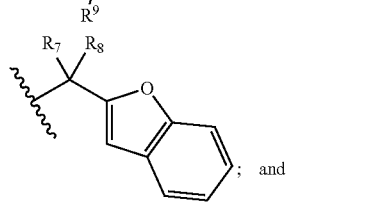

(2)

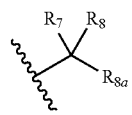

wherein all substitutents are as defined for formula (I).

Embodiment No. 66 is directed to the methods of this invention using compounds of formula (I) wherein substituent A is selected from the group consising of:

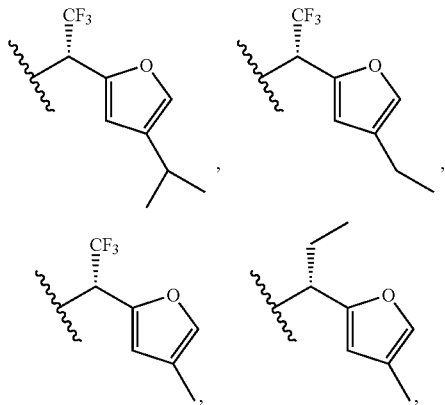

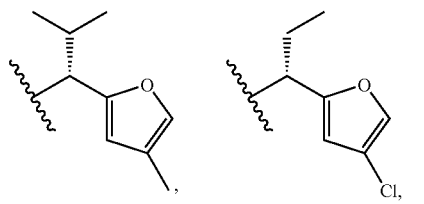

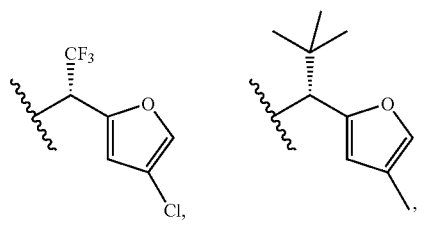

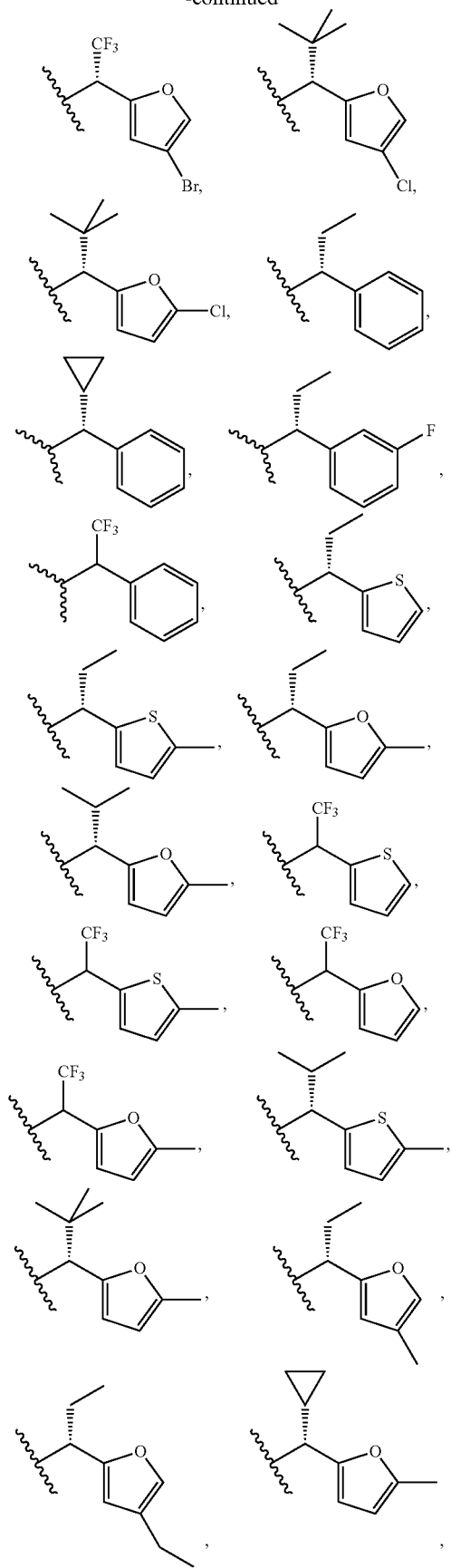
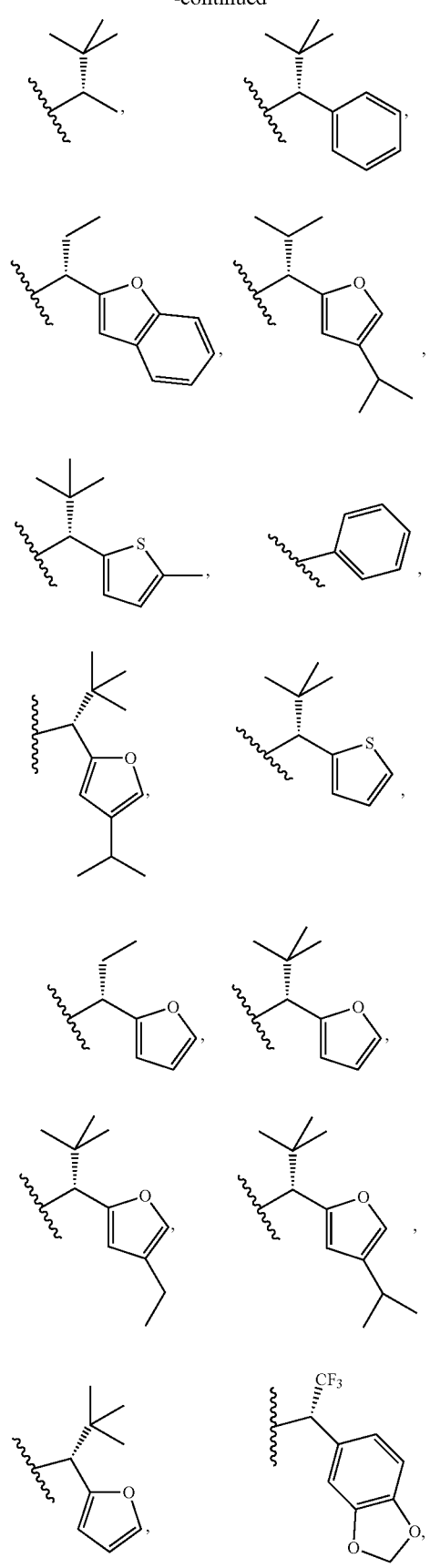

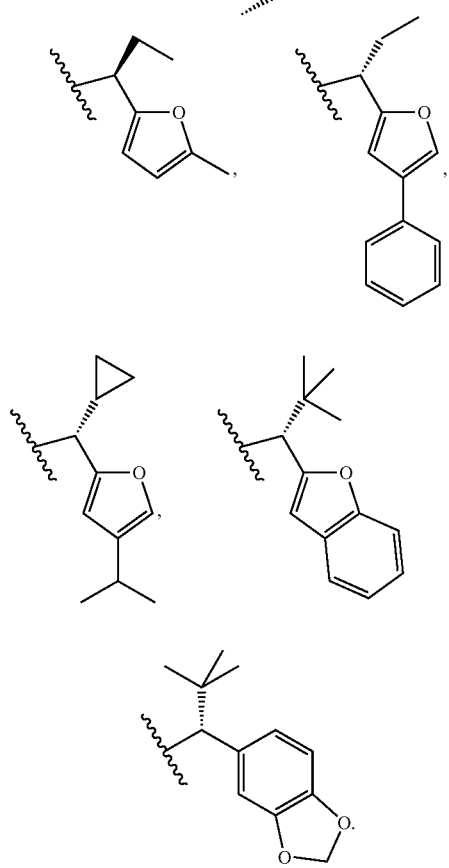
Embodiment No. 67 is directed to the methods of this invention using compounds of formula (I) wherein substituent A is selected from the group consisting of:
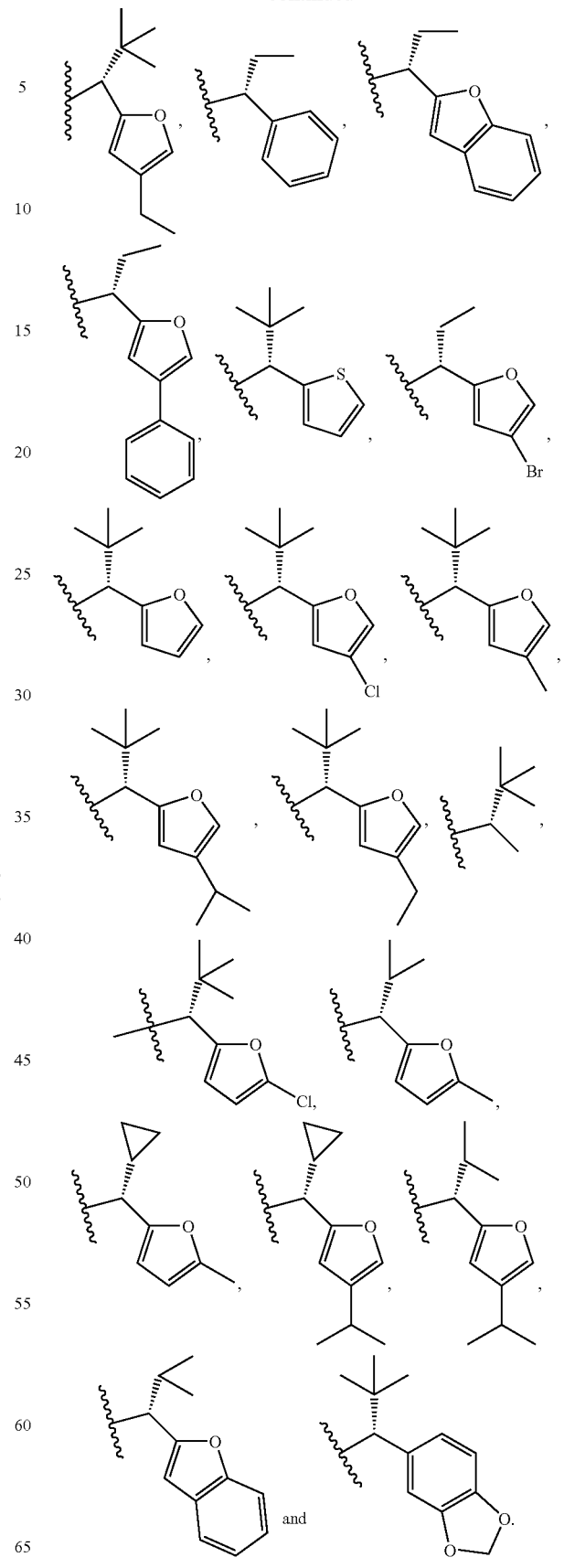

Embodiment No. 68 is directed to the methods of this invention using compounds of formula (I) wherein substituent A is selected from the group consisting of:

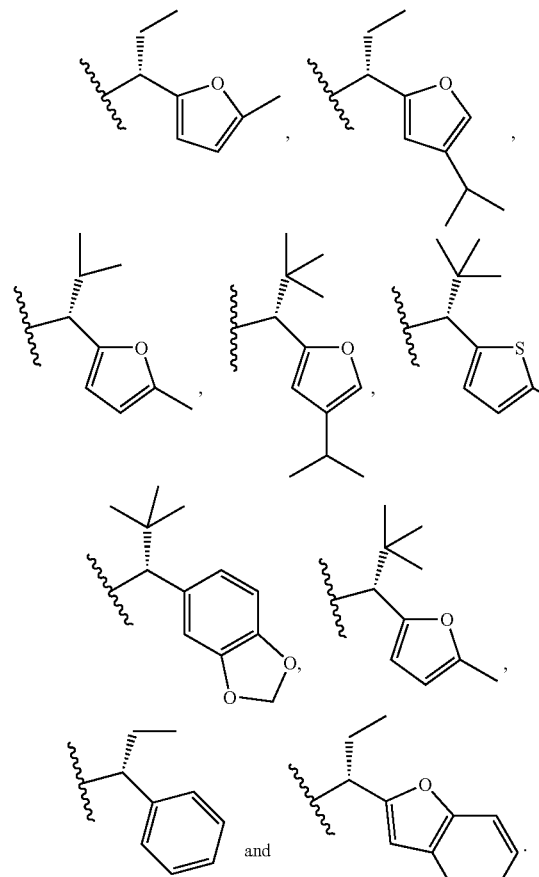

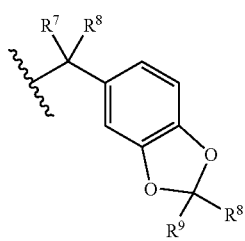

and

Embodiment No. 69 is directed to the methods of this invention using compounds of formula (I) wherein B is as described in any one of the Embodiment Nos. 1 to 59, and A is as defined in any one of the Embodiment Nos. 60 to 68.

Embodiment No. 70 is directed to the methods of this invention using compounds of formula (I) wherein B is as described in any one of the Embodiment Nos. 1 to 59, and A is:

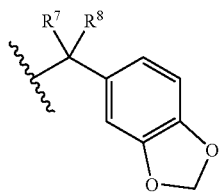

and all other substituents are as defined for formula (I).

Embodiment No. 71 is directed to the methods of this invention using compounds of formula (I) wherein B is as described in any one of the Embodiment Nos. 1 to 59, and A is:

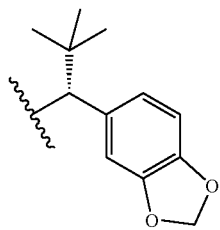

wherein $R^7$ is H, and $R^8$ is alkyl (e.g., methyl, ethyl, isopropyl, cyclopropyl and t-butyl), and all other substituents are as defined for formula (I).

Embodiment No. 72 is directed to the methods of this invention using compounds of formula (I) wherein B is as described in any one of the Embodiment Nos. 1 to 59, and A is:

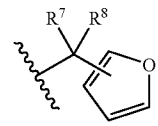

and all other substituents are as defined for formula (I).

Embodiment No. 73 is directed to the methods of this invention using compounds of formula (I) wherein B is as described in any one of the Embodiment Nos. 1 to 59, and A is:

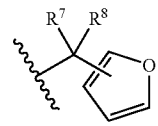

wherein the furan ring is unsubstituted or substituted as described in the definition of A for formula (I), and all other substituents are as defined for formula (I).

Embodiment No. 74 is directed to the methods of this invention using compounds of formula (I) wherein B is described in any one of the Embodiment Nos. 1 to 59, and A is

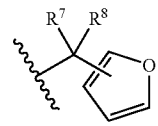

wherein the furan ring is substituted and all other substituents are as defined for formula (I).

Embodiment No. 75 is directed to the methods of this invention using compounds of formula (I) wherein B is as described in any one of the Embodiment Nos. 1 to 59, and A is

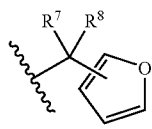

wherein the furan ring is substituted with at least one (e.g., 1 to 3, or 1 to 2) alkyl group and all other substituents are as defined for formula (I).

Embodiment No. 76 is directed to the methods of this invention using compounds of formula (I) wherein B is as described in any one of the Embodiment Nos. 1 to 59, A is

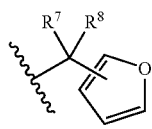

wherein the furan ring is substituted with one alkyl group and all other substituents are as defined for formula (I).

Embodiment No. 77 is directed to the methods of this invention using compounds of formula (I) wherein B is as described in any one of the Embodiment Nos. 1 to 59, and A is

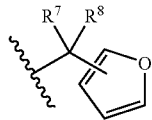

wherein the furan ring is substituted with one $C_1$ to $C_3$ alkyl group (e.g., methyl or isopropyl), and all other substituents are as defined for formula (I).

Embodiment No. 78 is directed to the methods of this invention using compounds of formula (I) wherein B is as described in any one of the Embodiment Nos. 1 to 59, and A is as defined in any one of the Embodiment Nos. 73 to 77, except that $R^7$ and $R^8$ are the same or different and each is selected from the group consisting of: H and alkyl.

Embodiment No. 79 is directed to the methods of this invention using compounds of formula (I) wherein B is as described in any one of the Embodiment Nos. 1 to 59, and A is as defined in any one of the Embodiment Nos. 73 to 77, except that $R^7$ is H, and $R^8$ is alkyl (e.g., ethyl or t-butyl).

Embodiment No. 80 is directed to the methods of this invention using compounds of formula (I) wherein:

(1) substituent A in formula (I) is selected from the group consisting of:

(a)

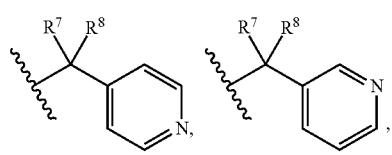

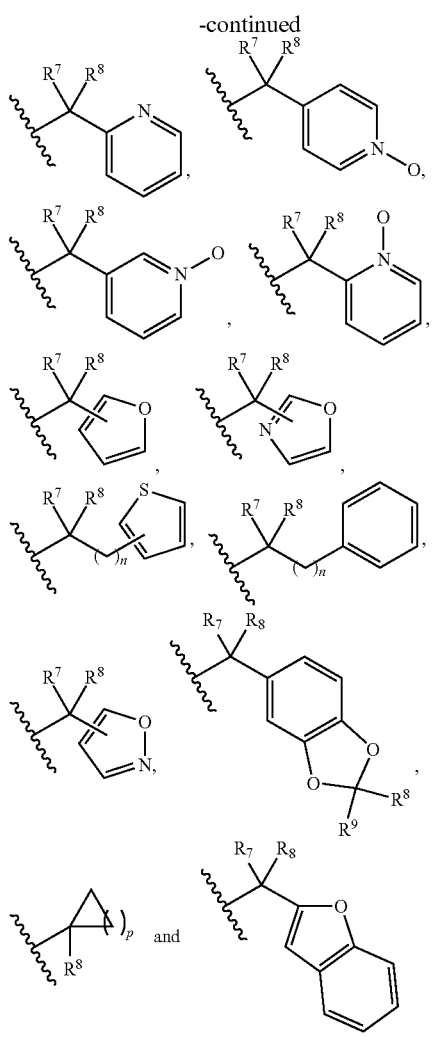

wherein the above rings are unsubstituted, as described for formula (I); and (b)

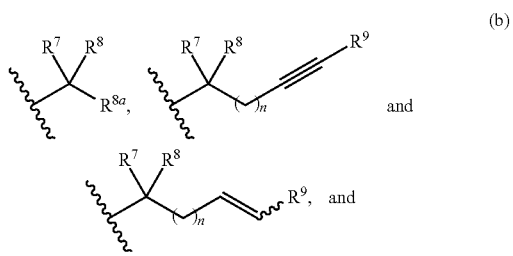

wherein in (a) and (b) above: each $R^7$ and $R^8$ is independently selected from the group consisting of: H, unsubstituted or substituted alkyl, unsubstituted or substituted aryl, unsubstituted or substituted heteroaryl, unsubstituted or substituted arylalkyl, unsubstituted or substituted heteroarylalkyl, unsubstituted or substituted cycloalkyl, unsubstituted or substituted cycloalkylalkyl, —$CO_2R^{13}$, —$CONR^{13}R^{14}$, fluoroalkyl, alkynyl, alkenyl, and cycloalkenyl, wherein said substituents on said $R^7$ and $R^8$ substituted groups are selected from the group consisting of: a) cyano, b) —$CO_2R^{13}$, c) —$C(O)NR^{13}R^{14}$, d) —$SO_2NR^{13}R^{14}$, e) —$NO_2$, f) —$CF_3$, g)

—OR[13], h) —NR[13]R[14], i) —OC(O)R[13], j) —OC(O)NR[13]R[14], and k) halogen; and R[8a] and R[9] are as defined in formula (I); and (2) substituent B in formula (I) is selected from the group consisting of:

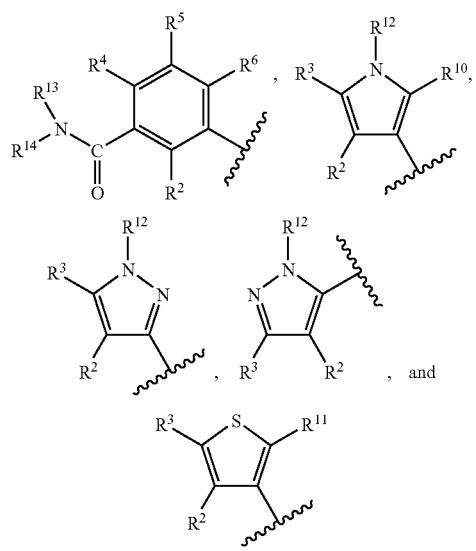

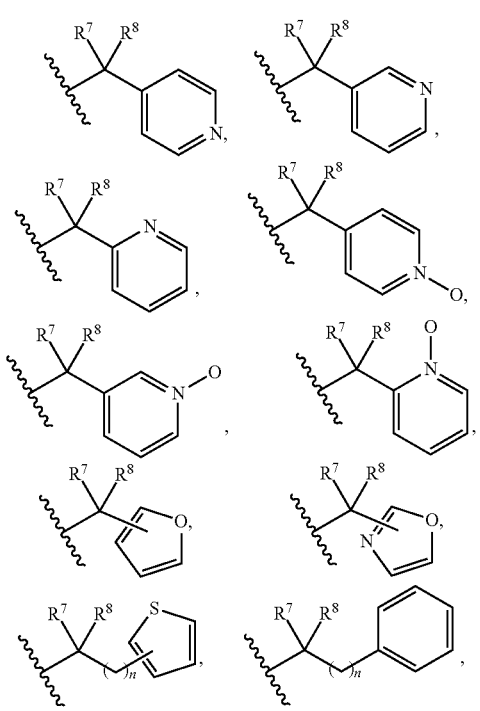

wherein R[2] to R[6] and R[10] to R[14] are as defined above for the compounds of formula (I).

Embodiment No. 81 is directed to the methods of this invention using compounds of formula (I) wherein:

(1) substituent A in formula (I) is selected from the group consisting of:

(a)

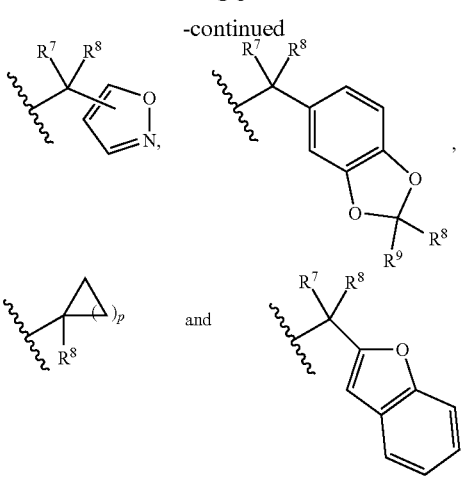

wherein the above rings are unsubstituted, or the above rings are substituted with 1 to 3 substituents independently selected from the group consisting of: halogen, alkyl, cycloalkyl, —CF$_3$, cyano, —OCH$_3$, and —NO$_2$; each R[7] and R[8] is independently selected from the group consisting of: H, alkyl (e.g., methyl, ethyl, t-butyl, and isopropyl), fluoroalkyl (such as, —CF$_3$ and —CF$_2$CH$_3$), cycloalkyl (e.g., cyclopropyl, and cyclohexyl), and cycloalkylalkyl (e.g., cyclopropylmethyl); and R[9] is selected from the group consisting of: H, halogen, alkyl, cycloalkyl, —CF$_3$, cyano, —OCH$_3$, and —NO$_2$; and (b)

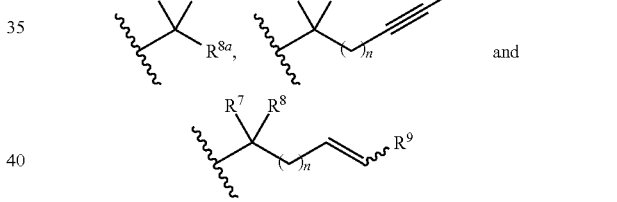

wherein each R[7] and R[8] is independently selected from the group consisting of: H, alkyl (e.g., methyl, ethyl, t-butyl, and isopropyl), fluoroalkyl (such as, —CF$_3$ and —CF$_2$CH$_3$), cycloalkyl (e.g., cyclopropyl, and cyclohexyl), and cycloalkylalkyl (e.g., cyclopropylmethyl); wherein R[8a] is as defined in formula (I), and wherein R[9] is selected from the group consisting of: H, halogen, alkyl, cycloalkyl, —CF$_3$, cyano, —OCH$_3$, and —NO$_2$; each R[7] and R[8] is independently selected from the group consisting of: H, alkyl (e.g., methyl, ethyl, t-butyl, and isopropyl), fluoroalkyl (such as, —CF$_3$ and —CF$_2$CH$_3$), cycloalkyl (e.g., cyclopropyl, and cyclohexyl), and cycloalkylalkyl (e.g., cyclopropylmethyl); and (2) substituent B in formula (I) is selected from the group consisting of:

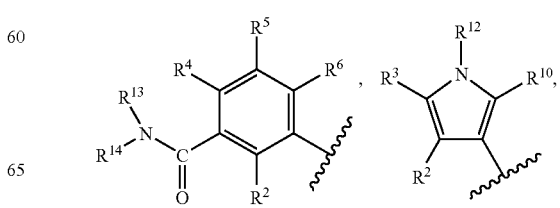

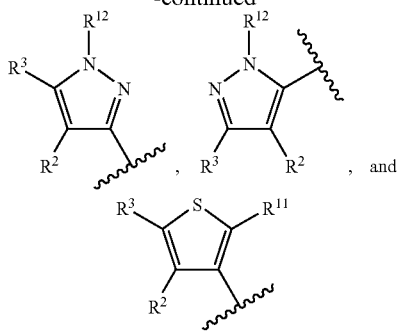
, and

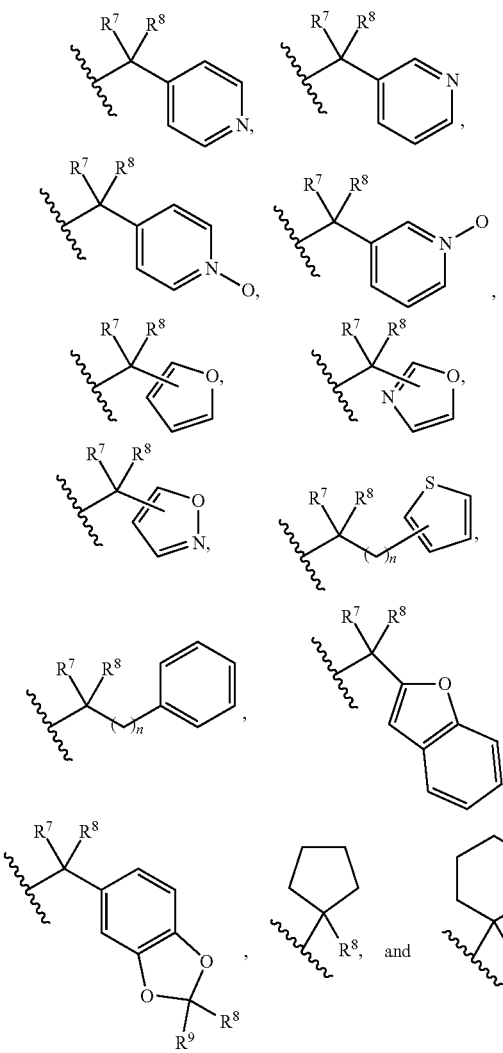

wherein

R² is selected from the group consisting of: H, OH, —NHC(O)R¹³ or and —NHSO₂R¹³;

R³ is selected from the group consisting of: —SO₂NR¹³R¹⁴, —NO₂, cyano, —C(O)NR¹³R¹⁴, —SO₂R¹³; and —C(O)OR¹³;

R⁴ is selected from the group consisting of: H, —NO₂, cyano, —CH₃, halogen, and —CF₃;

R⁵ is selected from the group consisting of: H, —CF₃, —NO₂, halogen and cyano;

R⁶ is selected from the group consisting of: H, alkyl and —CF₃;

each R¹⁰ and R¹¹ is independently selected from the group consisting of: R¹³, hydrogen, halogen, —CF₃, —NR¹³R¹⁴, —NR¹³C(O)NR¹³R¹⁴, —C(O)OR¹³, —SH, —SO₍ₜ₎NR¹³R¹⁴, —SO₂R¹³, —NHC(O)R¹³, —NHSO₂NR¹³R¹⁴, —NHSO₂R¹³, —C(O)NR¹³R¹⁴, —C(O)NR¹³OR¹⁴, —OC(O)R¹³, —COR¹³, —OR¹³, and cyano;

each R¹³ and R¹⁴ is independently selected from the group consisting of: H, methyl, ethyl and isopropyl; or R¹³ and R¹⁴ when taken together with the nitrogen they are attached to in the groups —NR¹³R¹⁴, —C(O)NR¹³R¹⁴, —SO₂NR¹³R¹⁴, —OC(O)NR¹³R¹⁴, —CONR¹³R¹⁴, —NR¹³C(O)NR¹³R¹⁴, —SO₍ₜ₎NR¹³R¹⁴, —NHSO₂NR¹³R¹⁴ form an unsubstituted or substituted saturated heterocyclic ring (preferably a 3 to 7 membered ring) optionally having one additional heteroatom selected from the group consisting of: O, S or NR¹⁸; wherein R¹⁸ is selected from the group consisting of: H, alkyl, aryl, heteroaryl, —C(O)R¹⁹, —SO₂R¹⁹ and —C(O)NR¹⁹R²⁰; wherein each R¹⁹ and R²⁰ is independently selected from the group consisting of: alkyl, aryl and heteroaryl; wherein there are 1 to 3 substituents on the substituted cyclized R¹³ and R¹⁴ groups (i.e., the substituents on the ring formed when R¹³ and R¹⁴ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR¹⁵, —C(O)NR¹⁵R¹⁶, —SO₍ₜ₎NR¹⁵R¹⁶, —C(O)R¹⁵, —SO₂R¹⁵ provided that R¹⁵ is not H, —NHC(O)NR¹⁵R¹⁶ and halogen; and wherein each R¹⁵ and R¹⁶ is independently selected from the group consisting: of H, alkyl, aryl, arylalkyl, cycloalkyl and heteroaryl.

Embodiment No. 82 is directed to the methods of this invention using compounds of formula (I) wherein substituent A is even more preferably selected from the group consisting of:

wherein the above rings are unsubstituted, or the above rings are substituted with 1 to 3 substituents independently selected from the group consisting of: H, F, Cl, Br, alkyl, cycloalkyl, and —CF₃; R⁷ is selected from the group consisting of: H, fluoroalkyl, alkyl and cycloalkyl; R⁸ is selected form the group consisting of: H, alkyl, —CF₂CH₃ and —CF₃; and R⁹ is selected from the group consisting of: H, F, Cl, Br, alkyl or —CF₃; and

wherein R⁷ is selected from the group consisting of: H, fluoroalkyl, alkyl and cycloalkyl; R⁸ is selected form the group consisting of: H, alkyl, —CF₂CH₃ and —CF₃; and R⁸ᵃ is as defined for formula (I).

Embodiment No. 83 is directed to the methods of this invention using compounds of formula (I) wherein:

(1) substituent A is selected from the group consisting of:

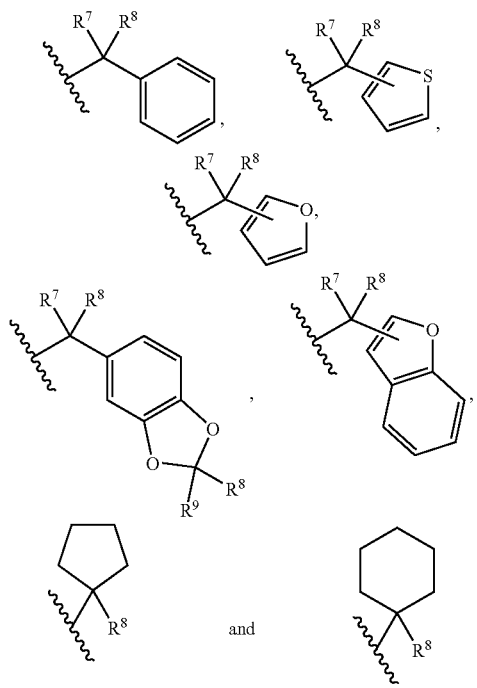

(a)

wherein the above rings are unsubstituted, or the above rings are substituted with 1 to 3 substituents independently selected from the group consisting of: H, F, Cl, Br, alkyl, cycloalkyl, and —$CF_3$; $R^7$ is selected from the group consisting of: H, —$CF_3$, —$CF_2CH_3$, methyl, ethyl, isopropyl, cyclopropyl and t-butyl; and $R^8$ is H; and

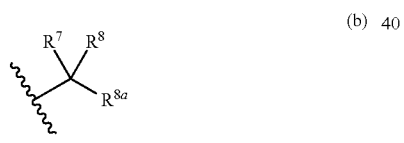

(b)

wherein $R^7$ is selected from the group consisting of: H, —$CF_3$, —$CF_2CH_3$, methyl, ethyl, isopropyl, cyclopropyl and t-butyl; and $R^8$ is H; and $R^{8a}$ is as defined for formula (I); and (2) substituent B is selected from the group consisting of:

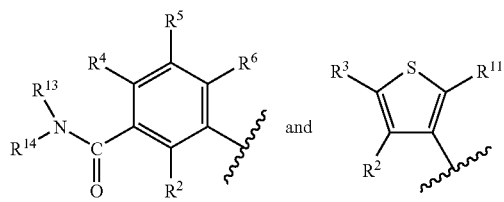

wherein:

$R^2$ is selected from the group consisting of: H, OH, —NHC(O)$R^{13}$ and —NHSO$_2R^{13}$;

$R^3$ is selected from the group consisting of: —C(O)NR$^{13}R^{14}$, —SO$_2NR^{13}R^{14}$, —NO$_2$, cyano, —SO$_2R^{13}$; and —C(O)OR$^{13}$;

$R^4$ is selected from the group consisting of: H, —NO$_2$, cyano, —CH$_3$ or —CF$_3$;

$R^5$ is selected from the group consisting of: H, —CF$_3$, —NO$_2$, halogen and cyano; and $R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: H, methyl, ethyl and isopropyl; or $R^{13}$ and $R^{14}$ when taken together with the nitrogen they are attached to in the groups —NR$^{13}R^{14}$, —C(O)NR$^{13}R^{14}$, —SO$_2NR^{13}R^{14}$, —OC(O)NR$^{13}R^{14}$, —CONR$^{13}R^{14}$, —NR$^{13}$C(O)NR$^{13}R^{14}$, —SO$_t$NR$^{13}R^{14}$, —NHSO$_2NR^{13}R^{14}$ form an unsubstituted or substituted saturated heterocyclic ring (preferably a 3 to 7 membered ring) optionally having one additional heteroatom selected from O, S or NR$^{18}$ wherein R$^{18}$ is selected from H, alkyl, aryl, heteroaryl, —C(O)R$^{19}$, —SO$_2R^{19}$ and —C(O)NR$^{19}R^{20}$, wherein each R$^{19}$ and R$^{20}$ is independently selected from alkyl, aryl and heteroaryl, wherein there are 1 to 3 substituents on the substituted cyclized R$^{13}$ and R$^{14}$ groups (i.e., on the ring formed when R$^{13}$ and R$^{14}$ are taken together with the nitrogen to which they are bound) and each substituent is independently selected from the group consisting of: alkyl, aryl, hydroxy, hydroxyalkyl, alkoxy, alkoxyalkyl, arylalkyl, fluoroalkyl, cycloalkyl, cycloalkylalkyl, heteroaryl, heteroarylalkyl, amino, —C(O)OR$^{15}$, —C(O)NR$^{15}R^{16}$, —SO$_t$NR$^{15}R^{16}$, —C(O)R$^{15}$, —SO$_2R^{15}$ provided that R$^{15}$ is not H, —NHC(O)NR$^{15}R^{16}$ and halogen; and wherein each R$^{15}$ and R$^{16}$ is independently selected from the group consisting of: H, alkyl, aryl, arylalkyl, cycloalkyl and heteroaryl.

Embodiment No. 84 is directed to the methods of this invention using compounds of formula (I) wherein:

(1) substituent A is selected from the group consisting of:

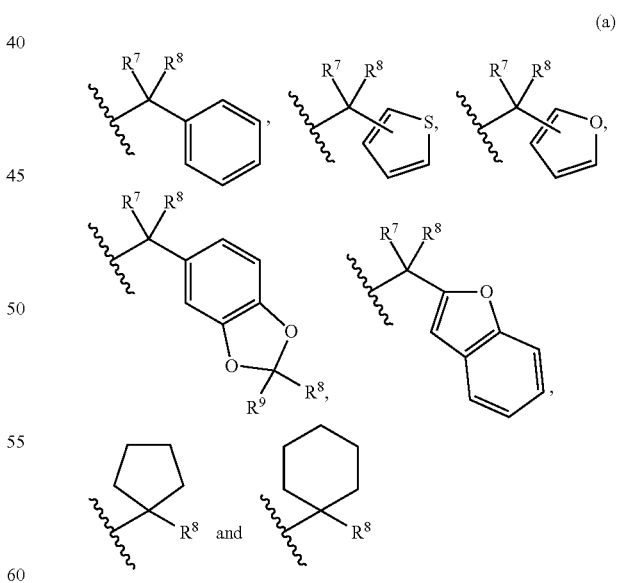

(a)

wherein the above rings are unsubstituted, or the above rings are substituted with 1 to 3 substituents independently selected from the group consisting of: F, Cl, Br, alkyl, cycloalkyl, and —CF$_3$; R$^7$ is selected from the group consisting of: H, —CF$_3$, —CF$_2CH_3$, methyl, ethyl, isopropyl, cyclopropyl and t-butyl; and R$^8$ is H; and

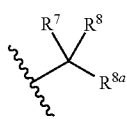

wherein $R^7$ is selected from the group consisting of: H, —$CF_3$, —$CF_2CH_3$, methyl, ethyl, isopropyl, cyclopropyl and t-butyl; and $R^8$ is H; and $R^{8a}$ is as defined for formula (I);

(2) substituent B is selected from the group consisting of:

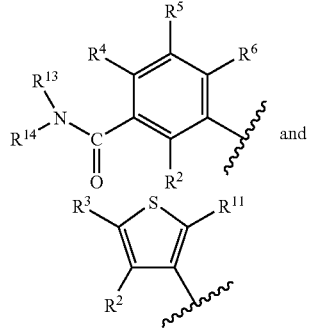

wherein:

$R^2$ is selected from the group consisting of: H, OH, —NHC(O)$R^{13}$ and —NHSO$_2R^{13}$;

$R^3$ is selected from the group consisting of: —C(O)NR$^{13}$R$^{14}$—SO$_2$NR$^{13}$R$^{14}$, —NO$_2$, cyano, and —SO$_2$R$^{13}$;

$R^4$ is selected from the group consisting of: H, —NO$_2$, cyano, —CH$_3$ or —CF$_3$;

$R^5$ is selected from the group consisting of: H, —CF$_3$, —NO$_2$, halogen and cyano; and $R^6$ is selected from the group consisting of: H, alkyl and —CF$_3$;

$R^{11}$ is selected from the group consisting of: H, halogen and alkyl; and each $R^{13}$ and $R^{14}$ is independently selected from the group consisting of: H, methyl and ethyl.

Embodiment No. 85 is directed to the methods of this invention using compounds of formula (I) wherein:

(1) substituent A is selected from the group consisting of:

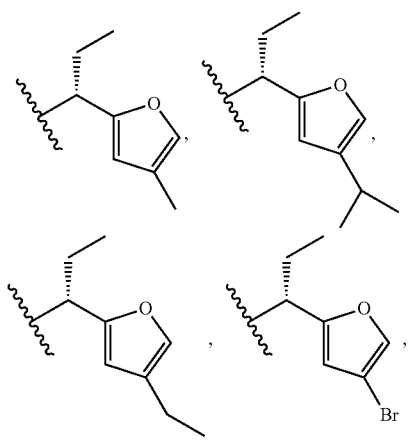

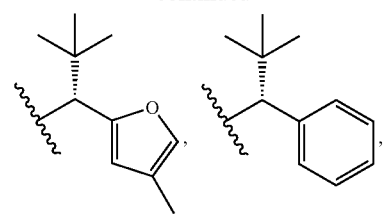

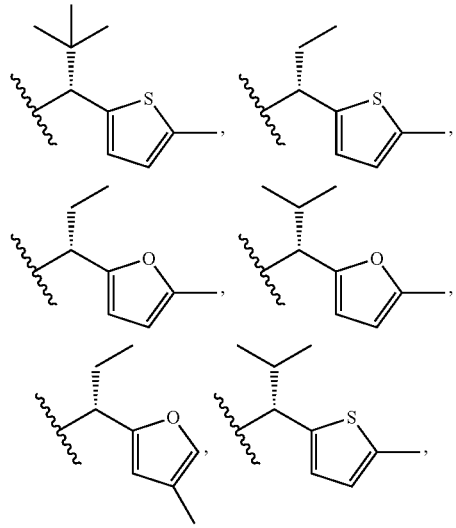

(2) substituent B is selected from the group consisting of:

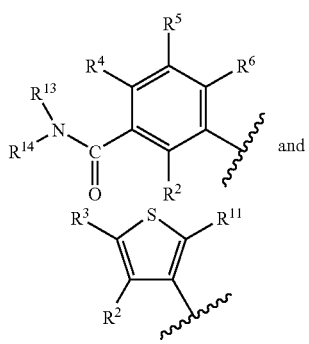

wherein:

R² is —OH;

R³ is selected from the group consisting of: —SO₂NR¹³R¹⁴ and —CONR¹³R¹⁴;

R⁴ is selected form the group consisting of: H, —CH₃ and —CF₃;

R⁵ is selected from the group consisting of: H and cyano;

R⁶ is selected from the group consisting of: H, —CH₃ and —CF₃;

R¹¹ is H; and

R¹³ and R¹⁴ are independently selected from the group consisting of H and methyl (e.g., for —SO₂NR¹³R¹⁴ both R¹³ and R¹⁴ are H, or both R¹³ and R¹⁴ are methyl, also, for example, for —CONR¹³R¹⁴ both R¹³ and R¹⁴ are methyl).

Embodiment No. 86 is directed to the methods of this invention using compounds of formula (I) wherein substituent A is as defined in Embodiment No. 65 and substituent B is as defined in Embodiment No. 57.

Embodiment No. 87 is directed to the methods of this invention using compounds of formula (I) wherein substituent A is as defined in Embodiment No. 65 and substituent B is as defined in Embodiment No. 58.

Embodiment No. 88 is directed to the methods of this invention using compounds of formula (I) wherein substituent A is as defined in Embodiment No. 65 and substituent B is as defined in Embodiment No. 59.

Embodiment No. 89 is directed to the methods of this invention using compounds of formula (I) wherein substituent A is as defined in Embodiment No. 66 and substituent B is as defined in Embodiment No. 57.

Embodiment No. 90 is directed to the methods of this invention using compounds of formula (I) wherein substituent A is as defined in Embodiment No. 66 and substituent B is as defined in Embodiment No. 58.

Embodiment No. 91 is directed to the methods of this invention using compounds of formula (I) wherein substituent A is as defined in Embodiment No. 66 and substituent B is as defined in Embodiment No. 59.

Embodiment No. 92 is directed to the methods of this invention using compounds of formula (I) wherein substituent A is as defined in Embodiment No. 67 and substituent B is as defined in Embodiment No. 57.

Embodiment No. 93 is directed to the methods of this invention using compounds of formula (I) wherein substituent A is as defined in Embodiment No. 67 and substituent B is as defined in Embodiment No. 58.

Embodiment No. 94 is directed to the methods of this invention using compounds of formula (I) wherein substituent A is as defined in Embodiment No. 67 and substituent B is as defined in Embodiment No. 59.

Embodiment No. 95 is directed to the methods of this invention using compounds of formula (I) wherein substituent A is as defined in Embodiment No. 68 and substituent B is as defined in Embodiment No. 57.

Embodiment No. 96 is directed to the methods of this invention using compounds of formula (I) wherein substituent A is as defined in Embodiment No. 68 and substituent B is as defined in Embodiment No. 58.

Embodiment No. 97 is directed to the methods of this invention using compounds of formula (I) wherein substituent A is as defined in Embodiment No. 68 and substituent B is as defined in Embodiment No. 59.

Embodiment No. 98 is directed to the methods of this invention using compounds of formula (I) as defined in any one of the Embodiment Nos. 1 to 97 wherein the compound of formula (I) is a pharmaceutically acceptable salt.

Embodiment No. 99 is directed to the methods of this invention using compounds of formula (I) as defined in any one of the Embodiment Nos. 1 to 97 wherein the compound of formula (I) is a sodium salt.

Embodiment No. 100 is directed to the methods of this invention using compounds of formula (I) as defined in any one of the Embodiment Nos. 1 to 97 wherein the compound of formula (I) is a calcium salt.

Embodiment No. 101 is directed to the methods of this invention using a pharmaceutically acceptable salt of any one of the representative compounds of formula (I) described below.

Embodiment No. 102 is directed to the methods of this invention using a sodium salt of any one of the representative compounds of formula (I) described below.

Embodiment No. 103 is directed to the methods of this invention using a calcium salt of any one of the representative compounds of formula (I) described below.

Embodiment No. 104 is directed to the methods of this invention using a pharmaceutical composition comprising at least one (e.g., 1 to 3, usually 1) compound of formula (I) as described in any one of the Embodiment Nos. 1 to 103 in combination with a pharmaceutically acceptable carrier (or diluent).

Embodiment No. 105 is directed to a pharmaceutically acceptable salt of a novel compound of formula (I), wherein said compound is selected from the group consisting of:

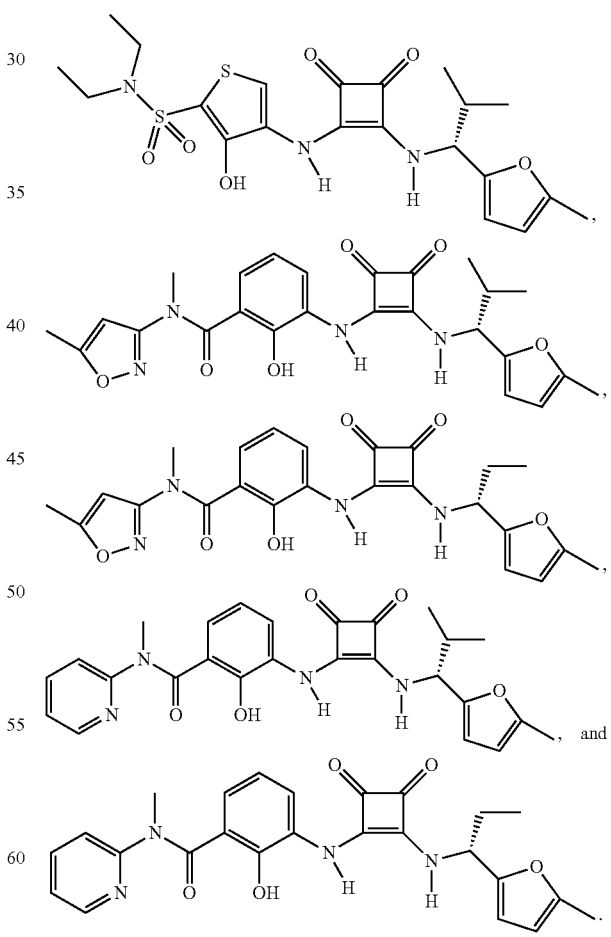

Embodiment No. 106 is directed to a calcium salt of any one of the novel compounds of formula (I) described in Embodiment No. 105.

Embodiment No. 107 is directed to a sodium salt of any one of the novel compounds of formula (I) described in Embodiment No. 105.

Embodiment No. 108 is directed to a pharmaceutical composition comprising at least one (e.g., 1 to 3, usually 1) novel compound of formula (I) as described in Embodiment No. 105 in combination with a pharmaceutically acceptable carrier (or diluent).

Representative compounds of formula (I) useful in the methods of this invention include but are not limited to:

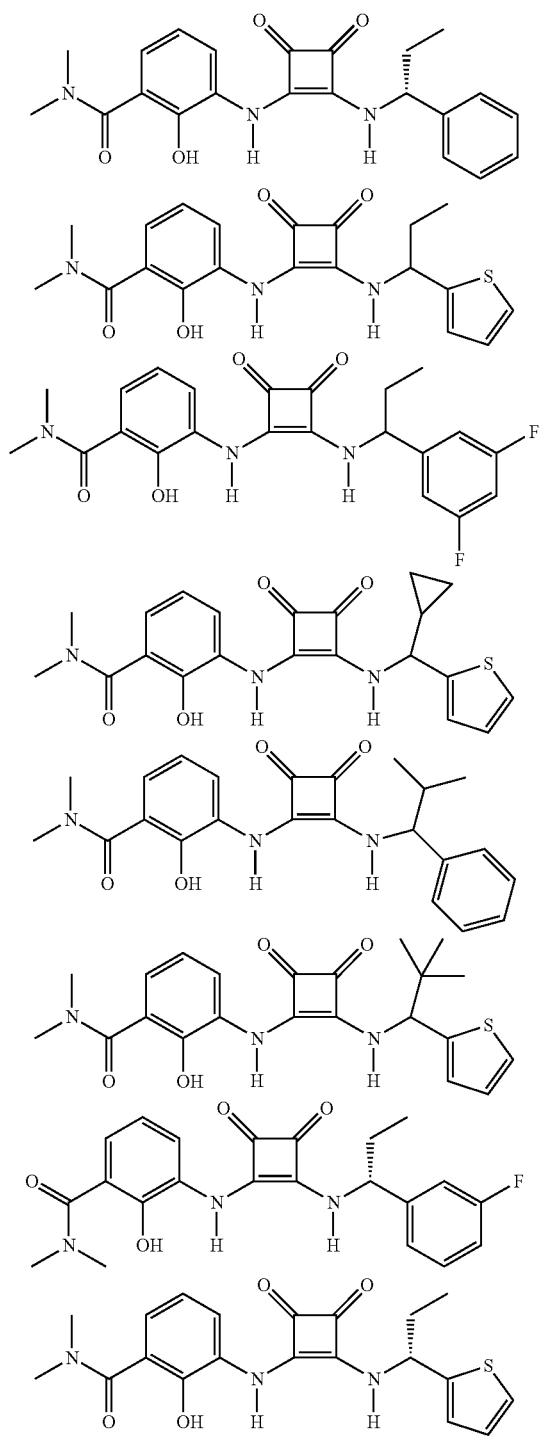

-continued

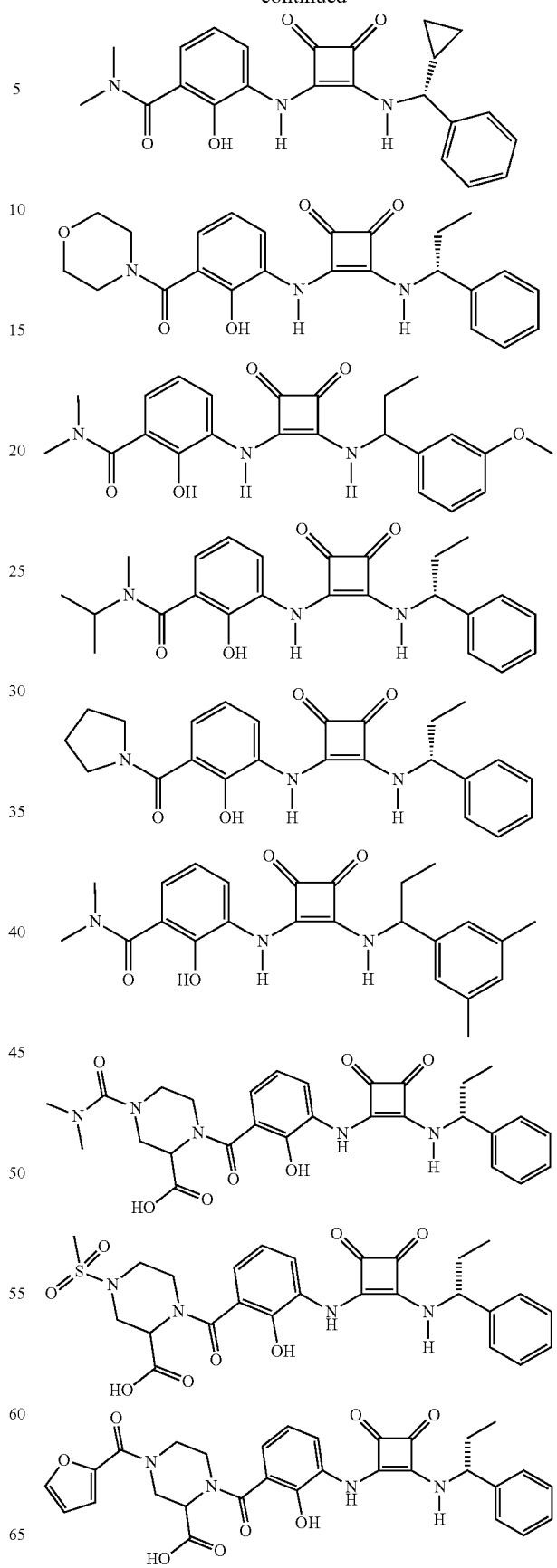

67
-continued
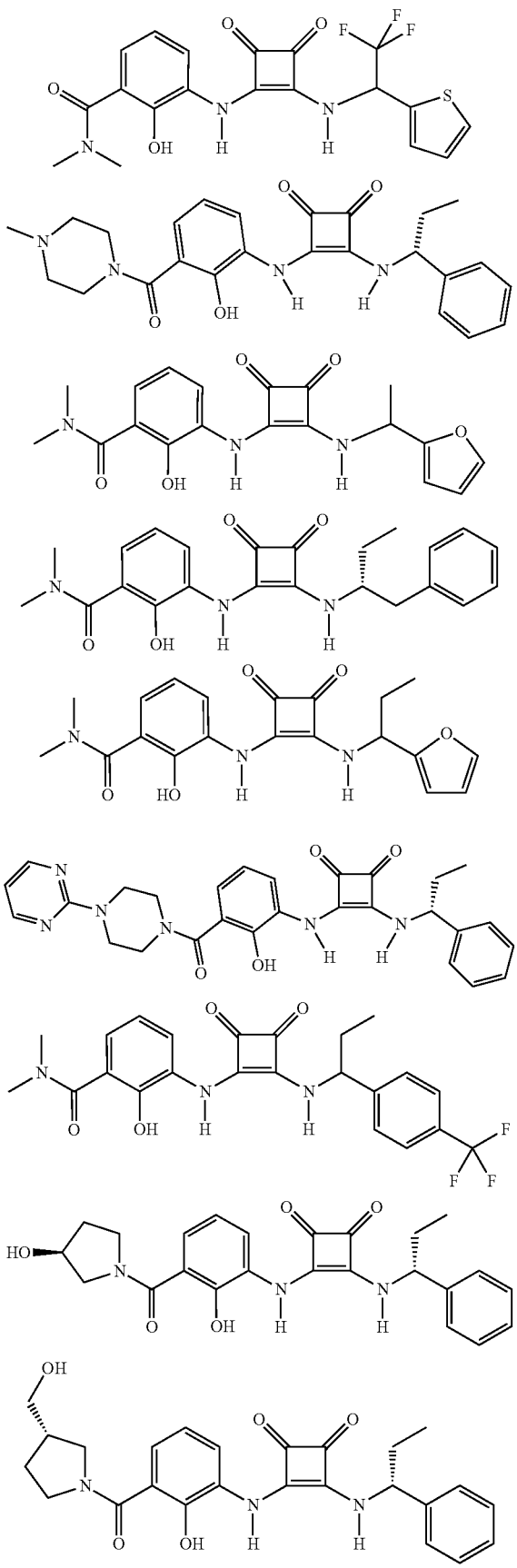
68
-continued
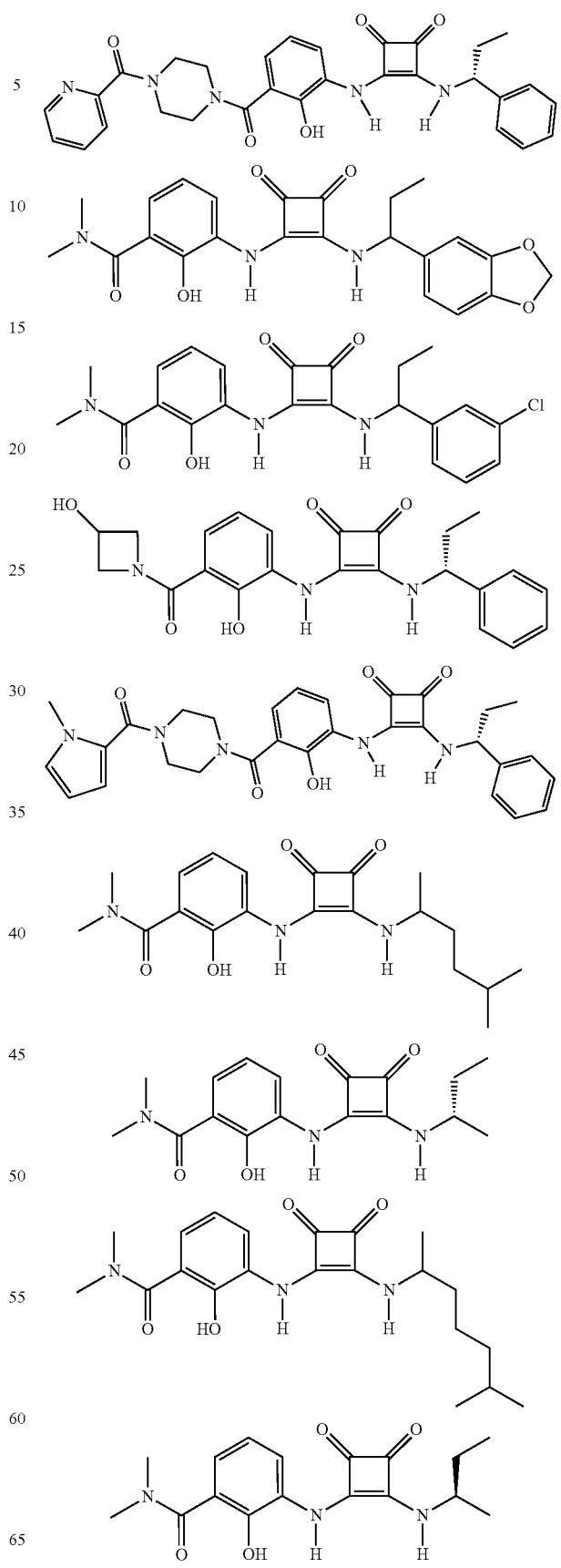

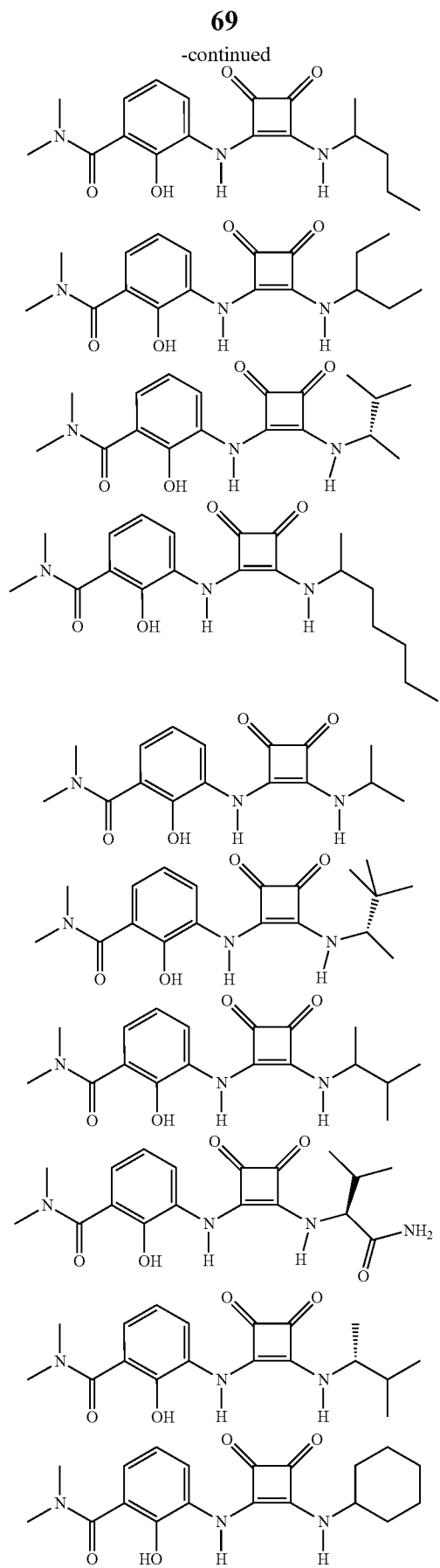
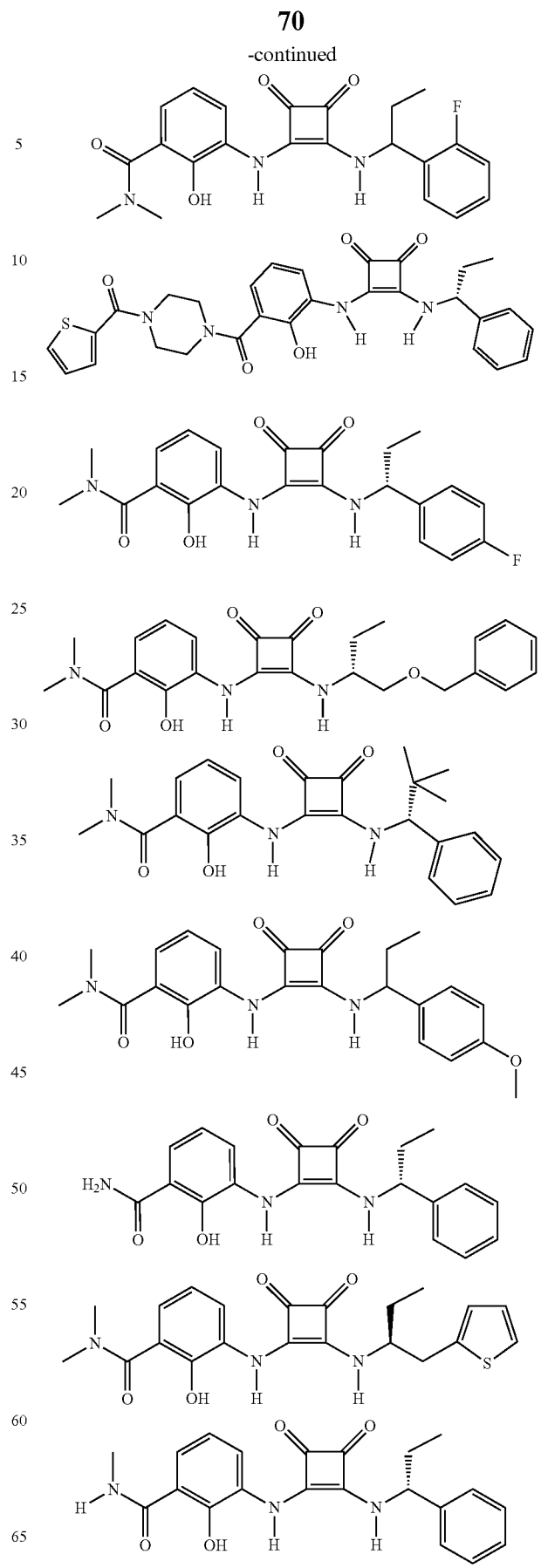

71
-continued
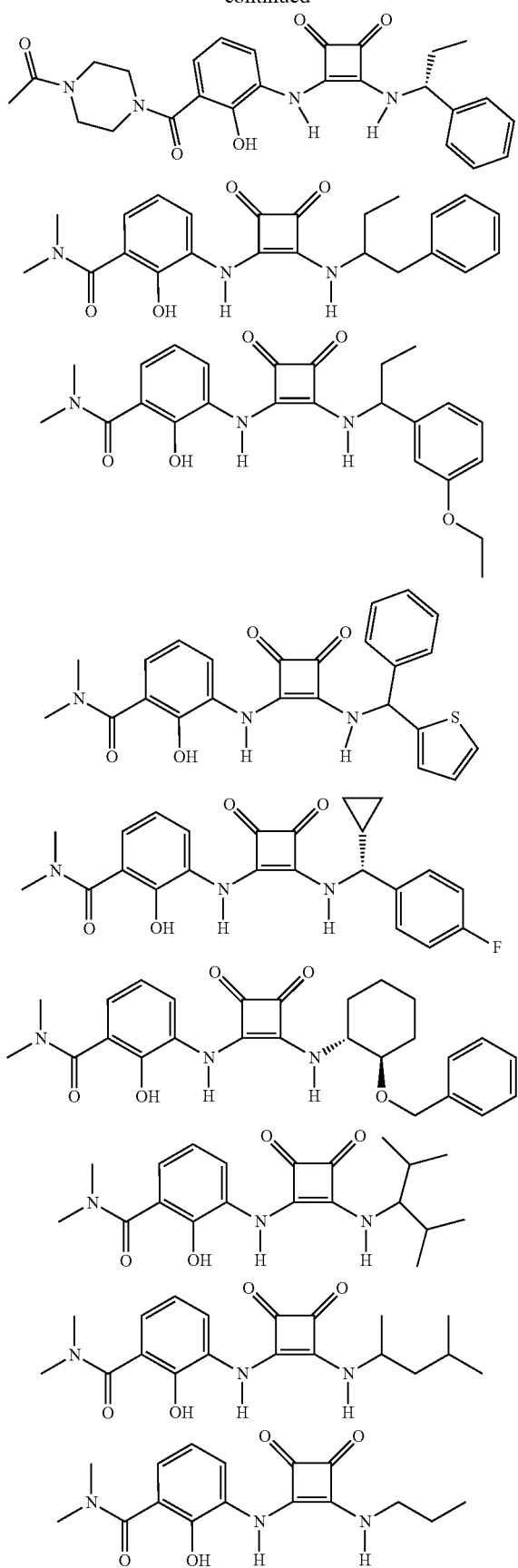
72
-continued
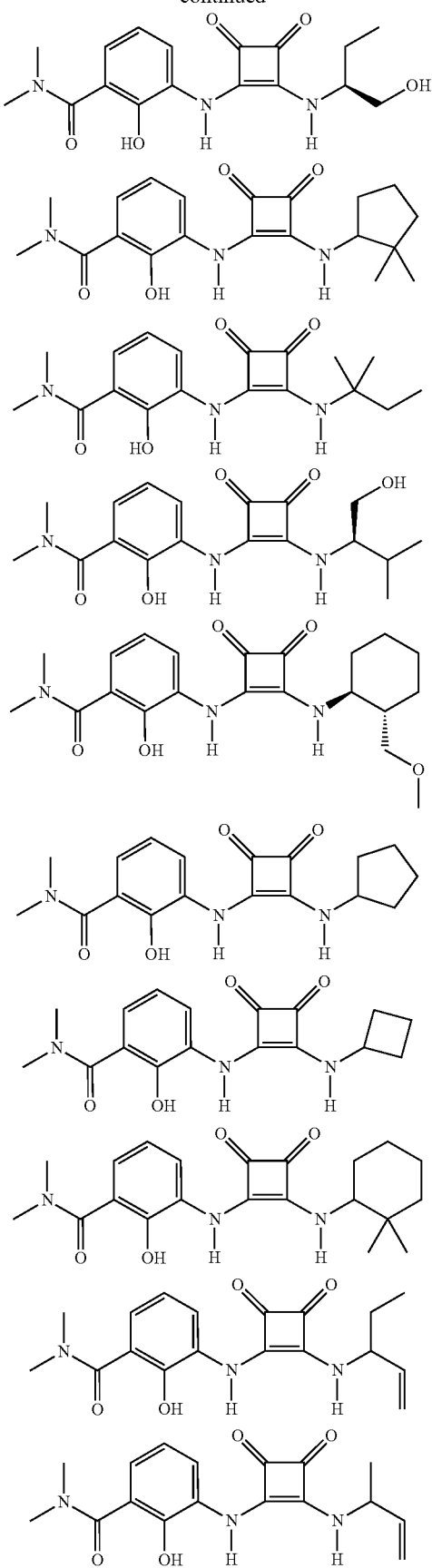

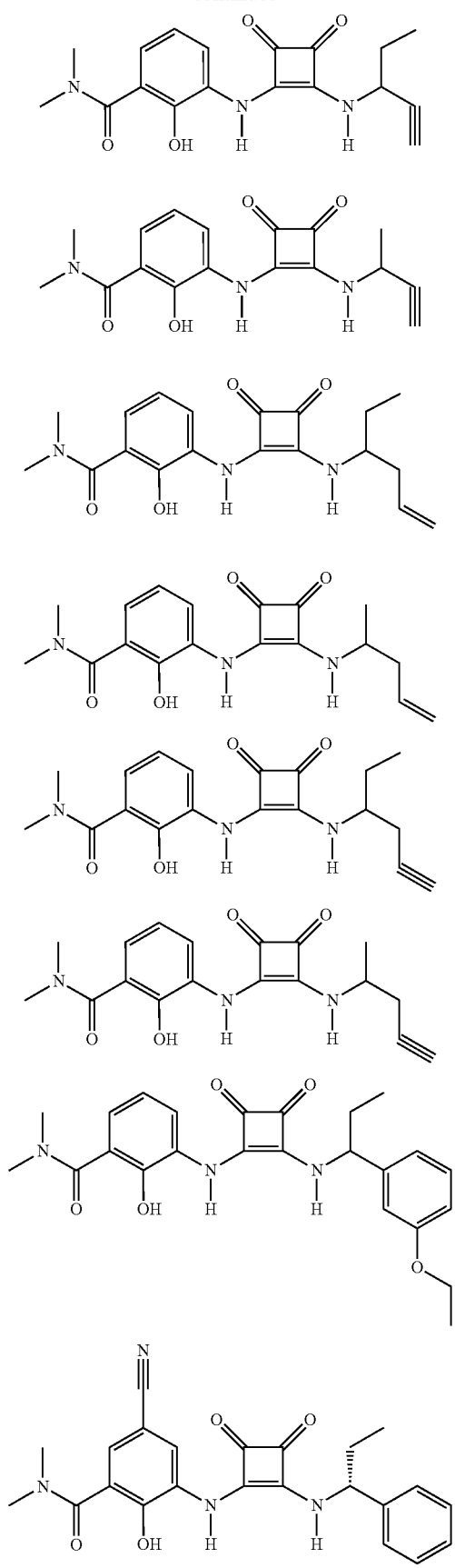
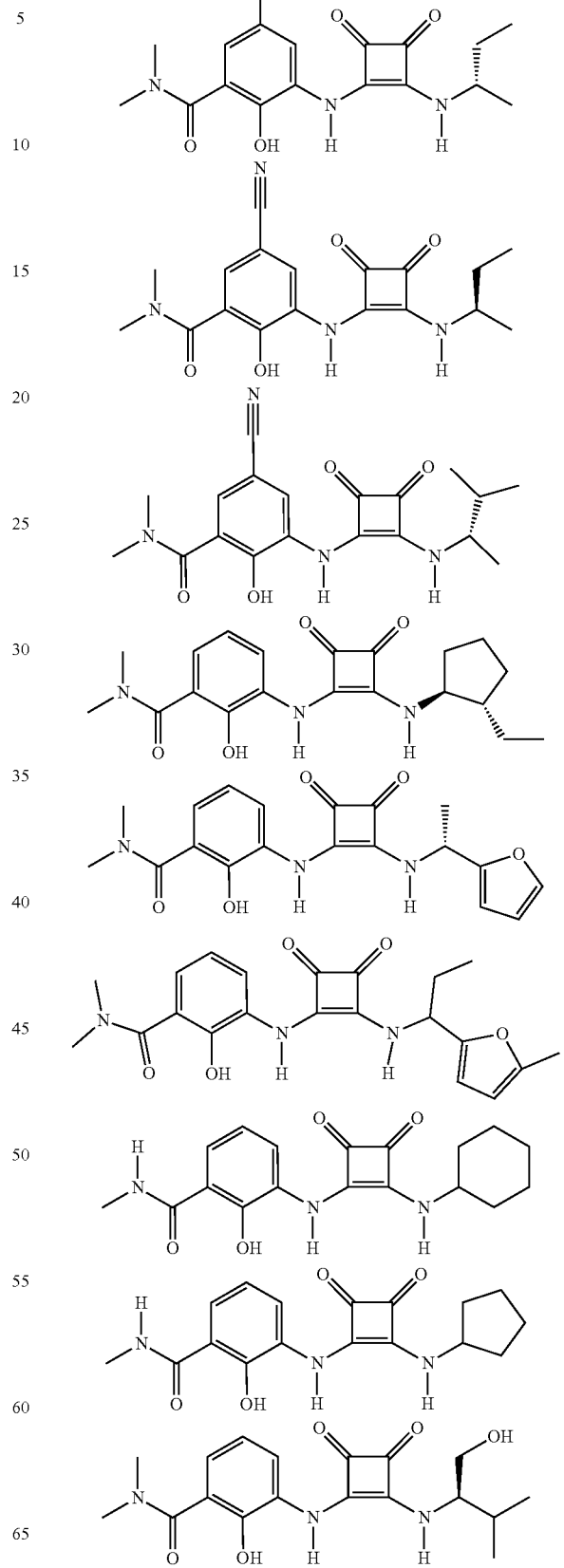

75
-continued
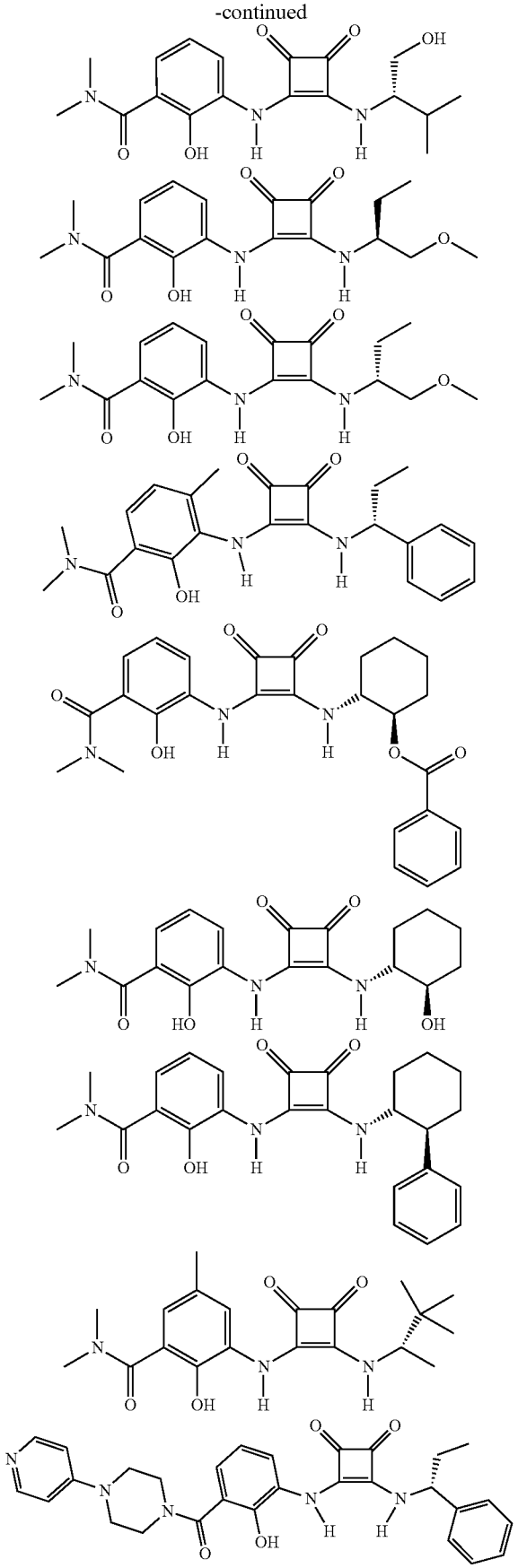
76
-continued
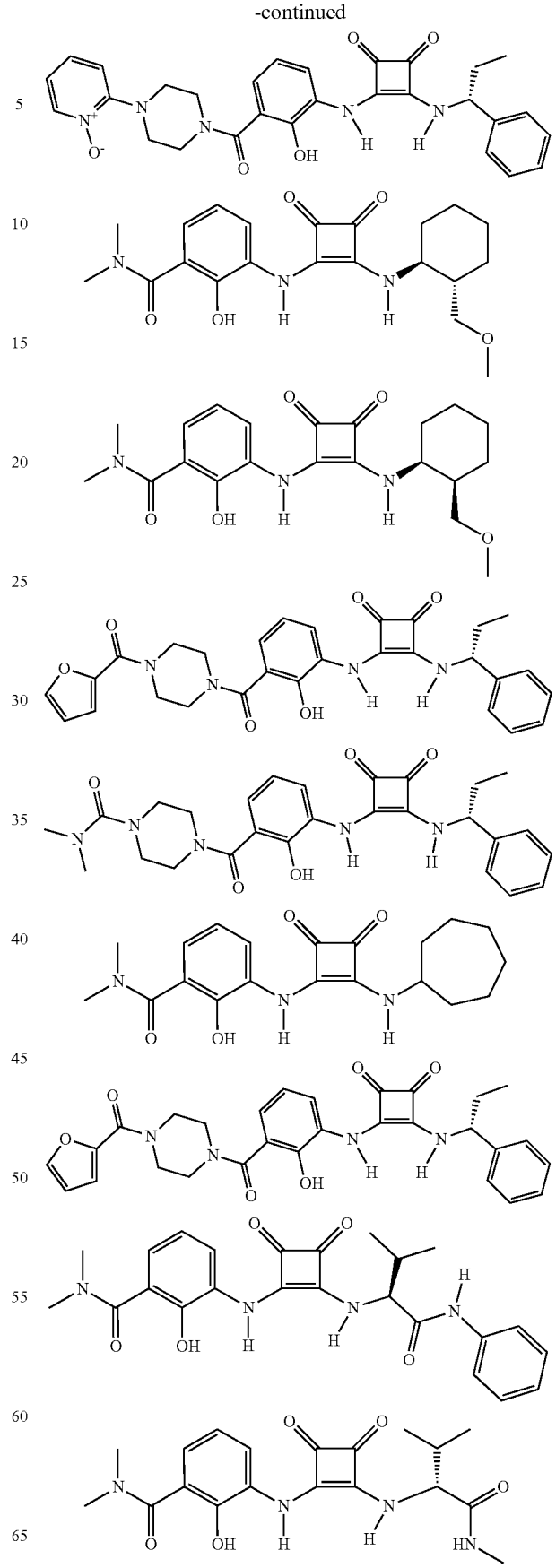

77
-continued
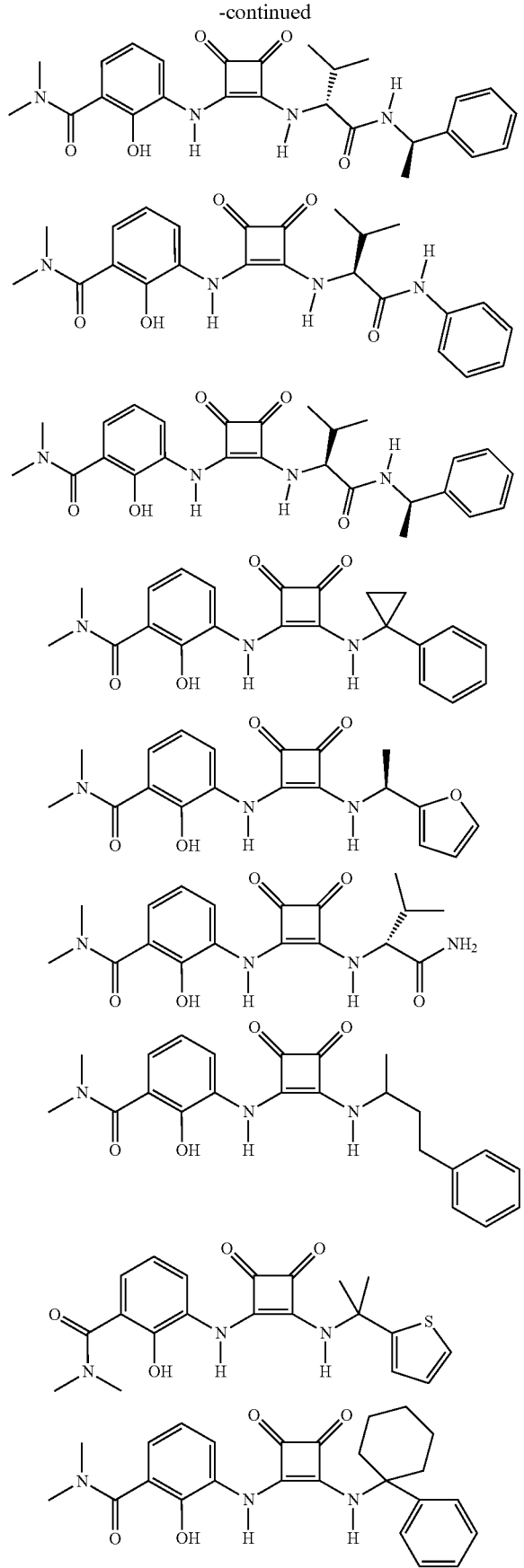
78
-continued
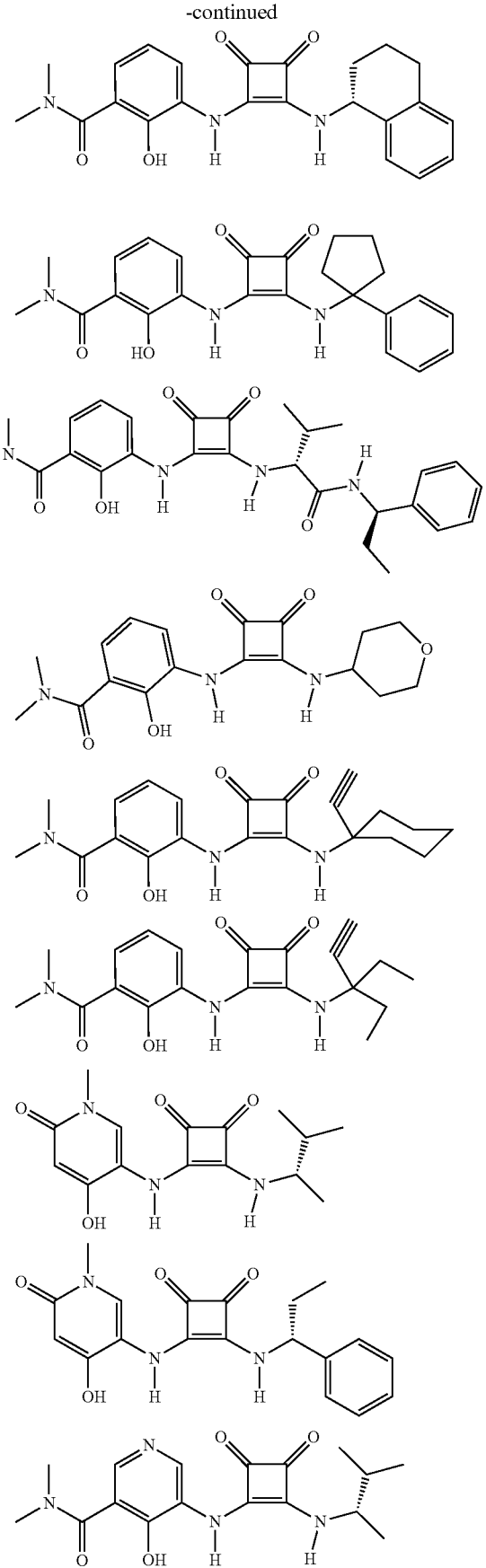

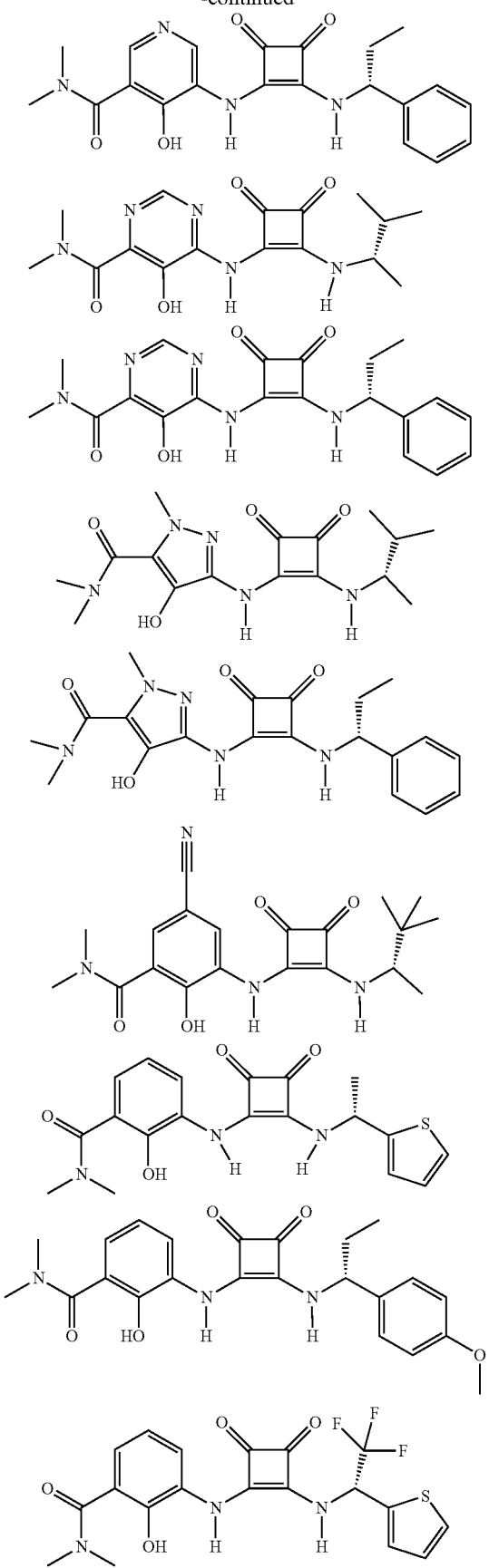
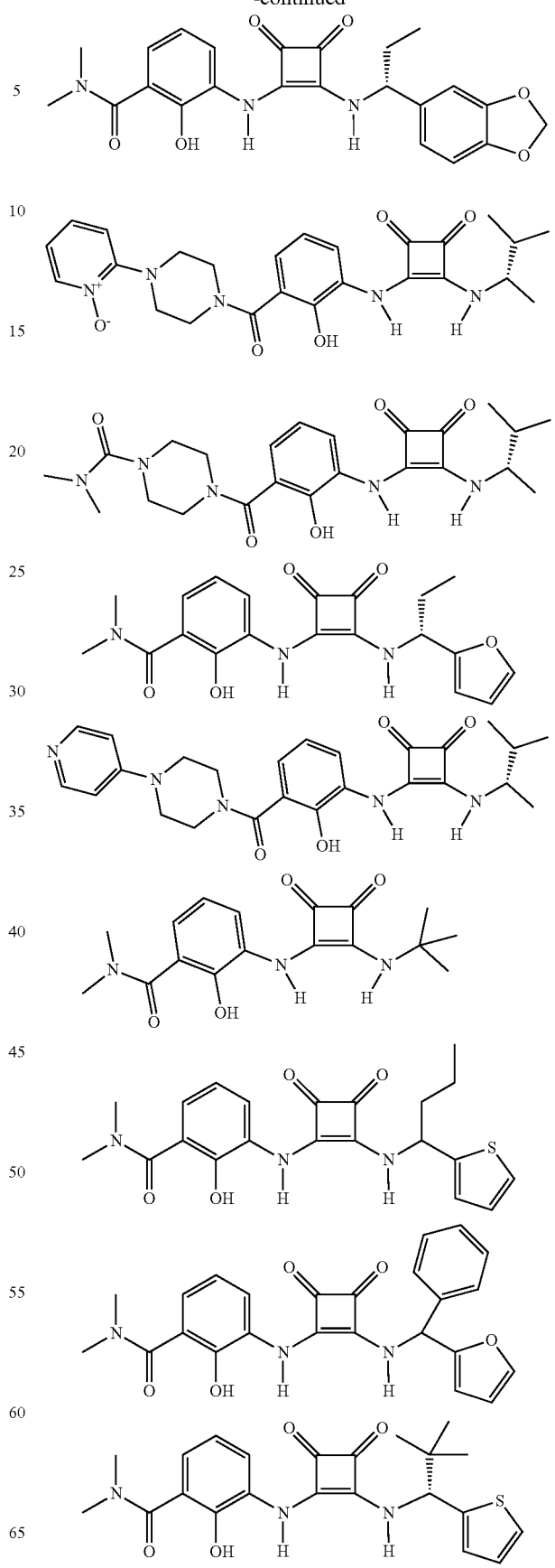

81
-continued
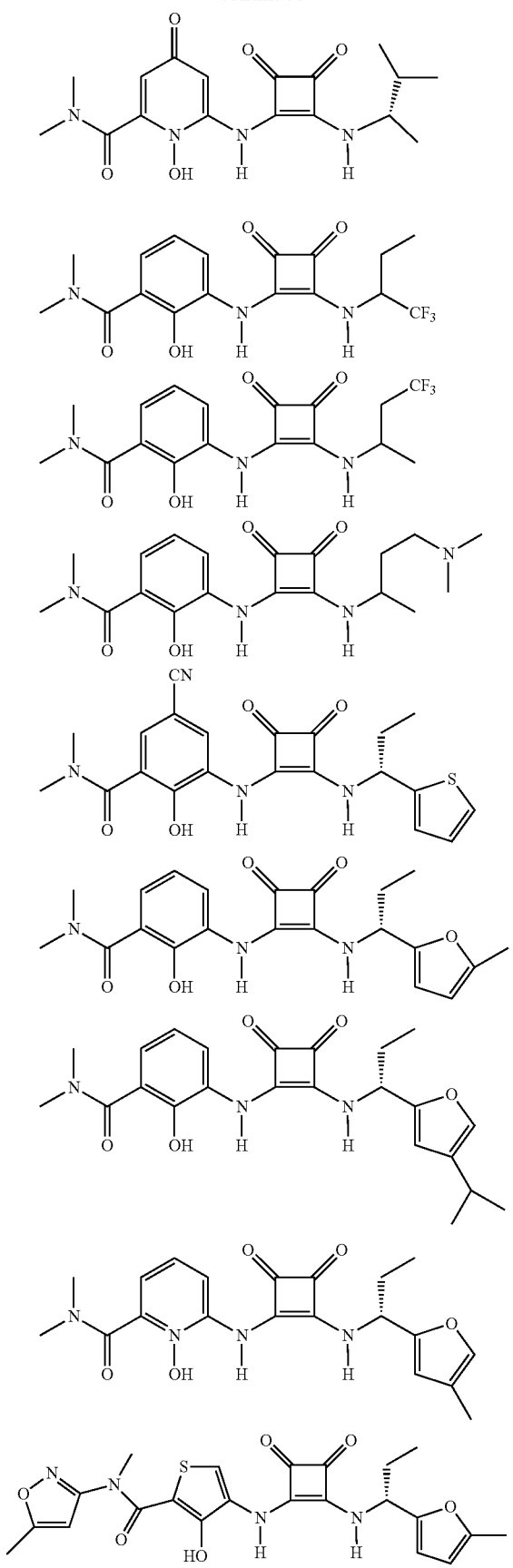
82
-continued
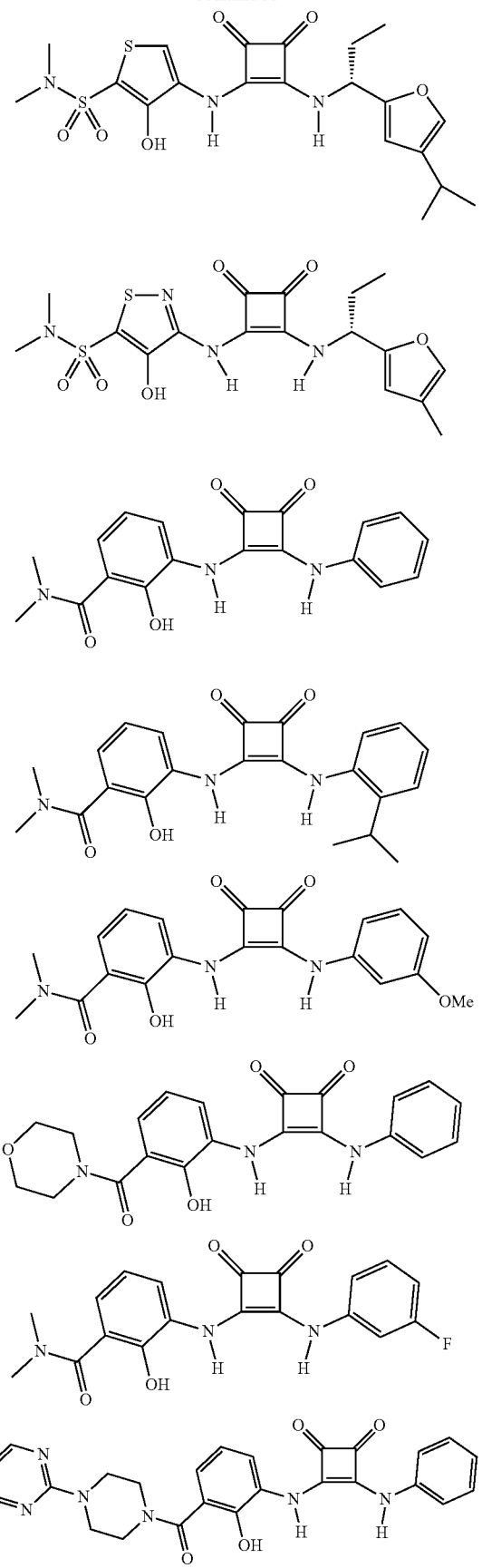

83
-continued
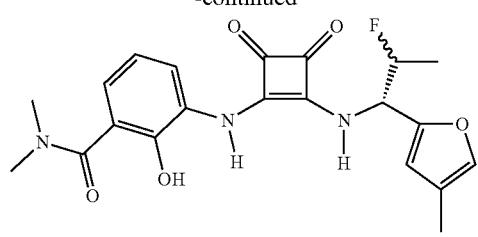
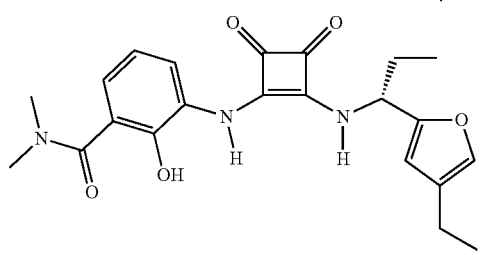
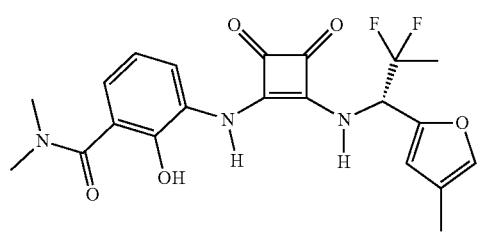
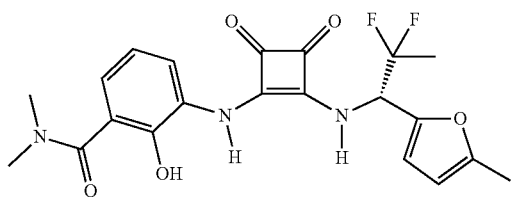
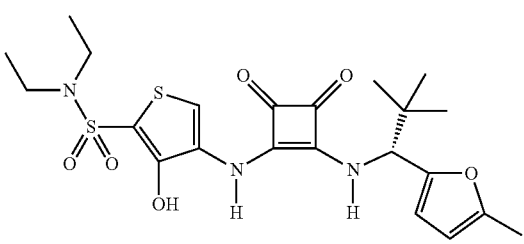
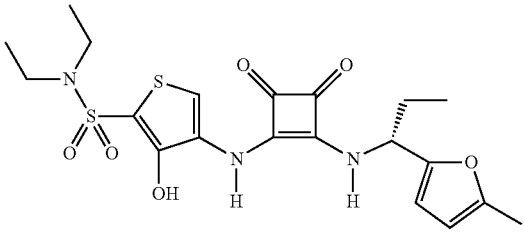
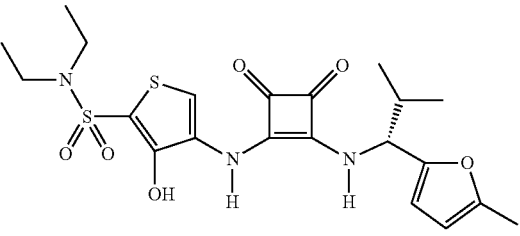
84
-continued
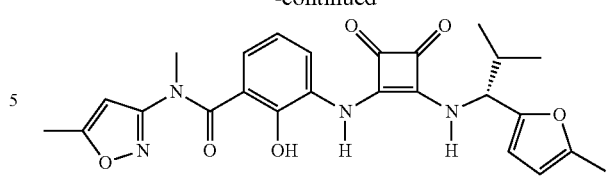
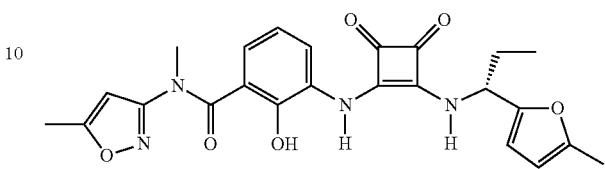
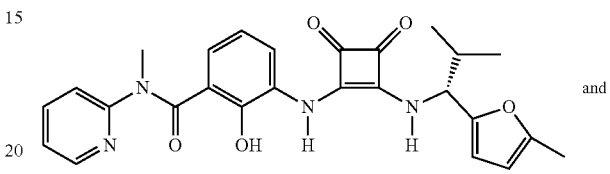
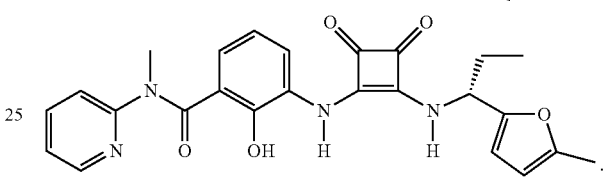
and
Preferred compounds of formula (I) useful in the methods of this invention include:
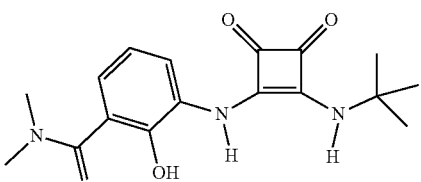
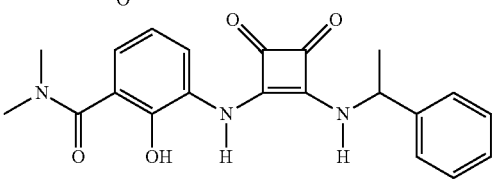
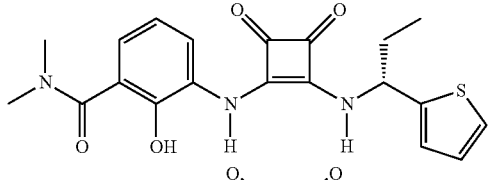
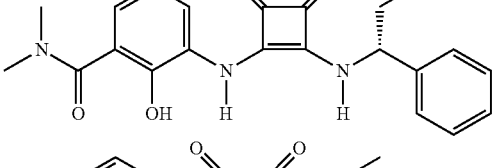
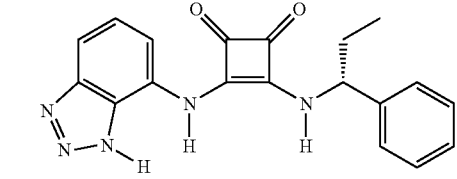

85
-continued
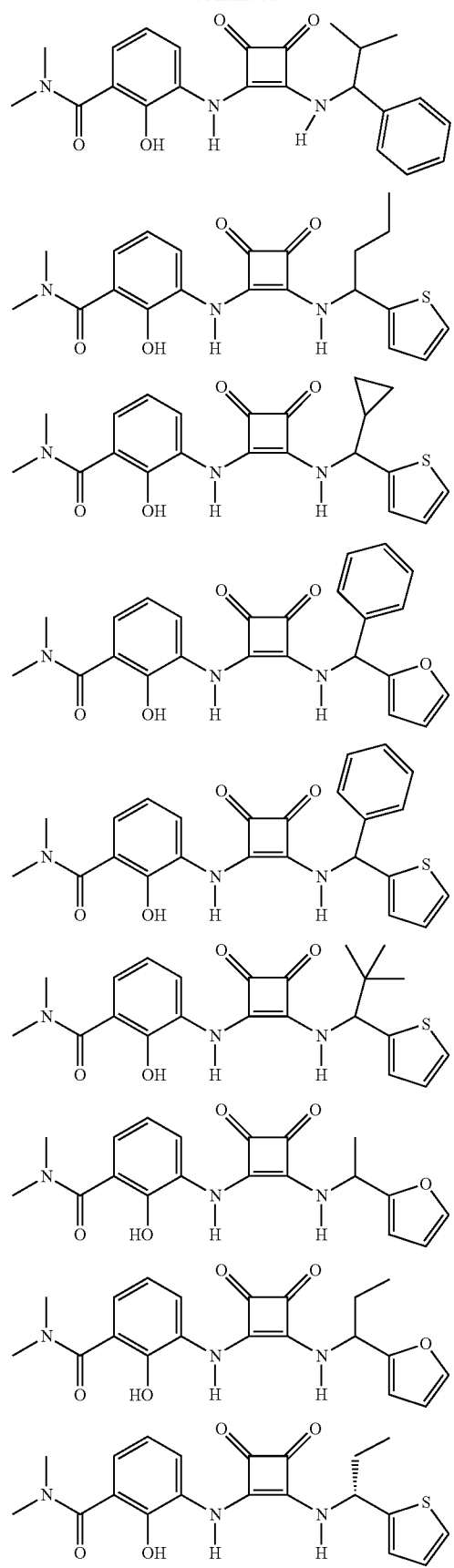
86
-continued
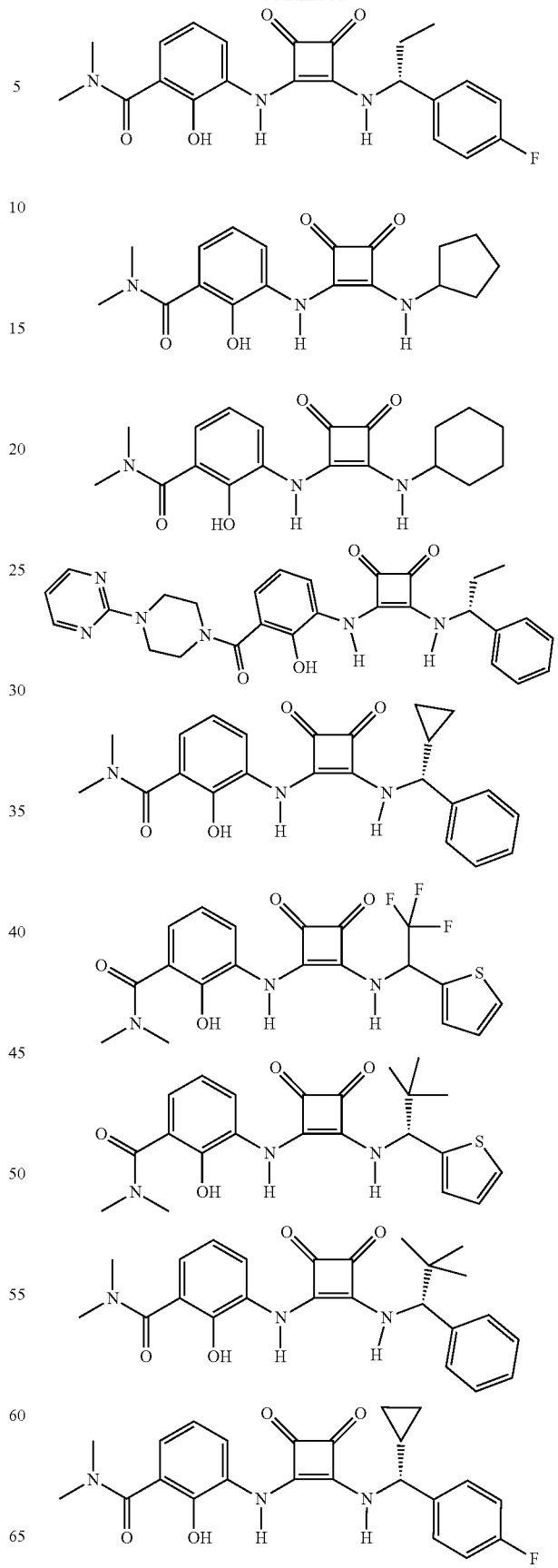

87
-continued
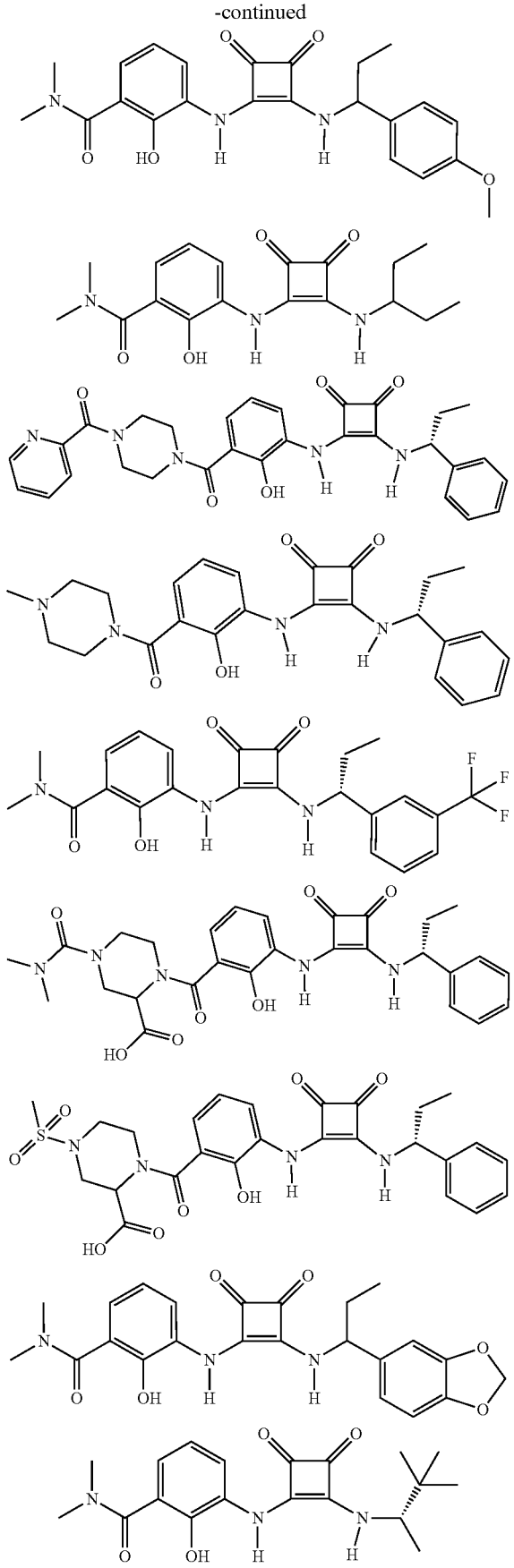
88
-continued
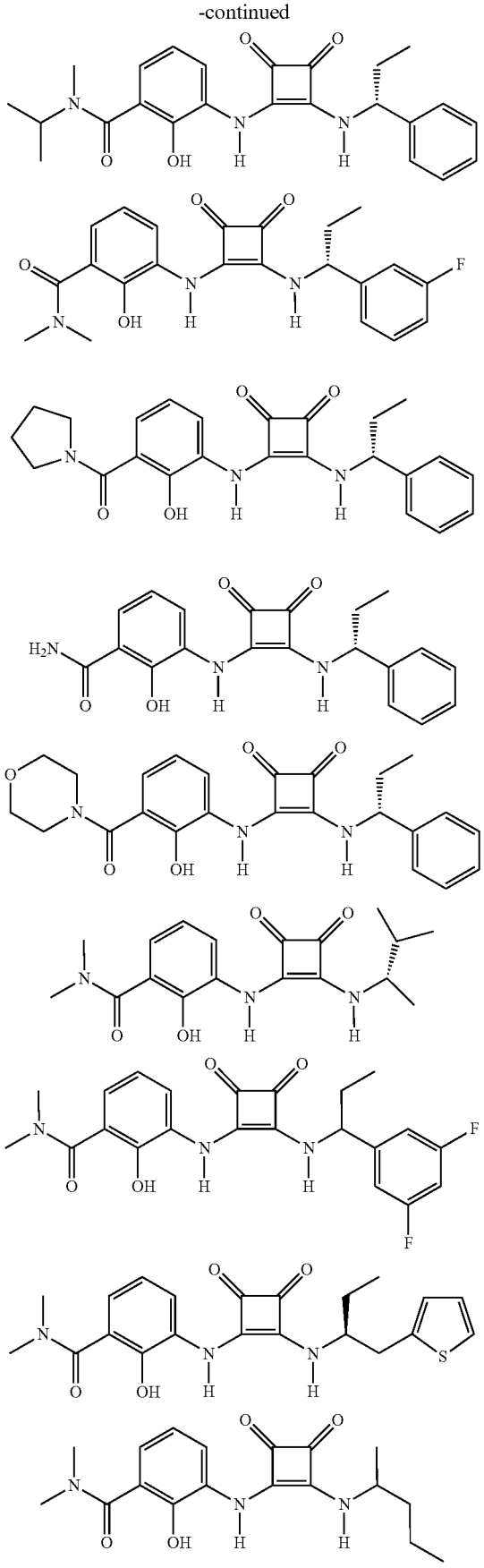

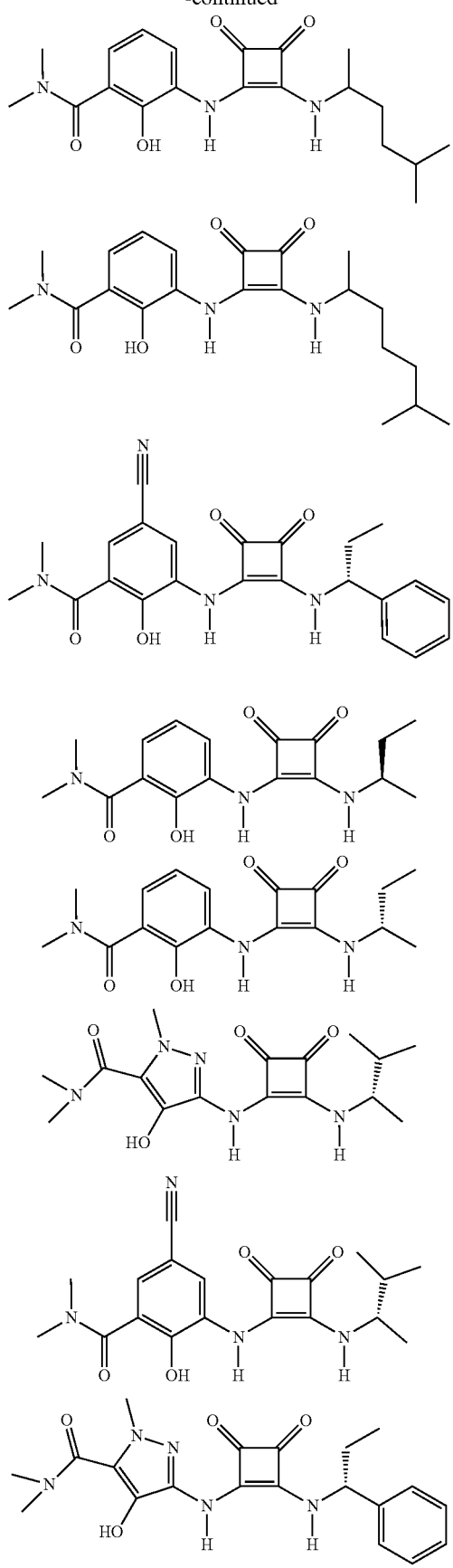

91
-continued
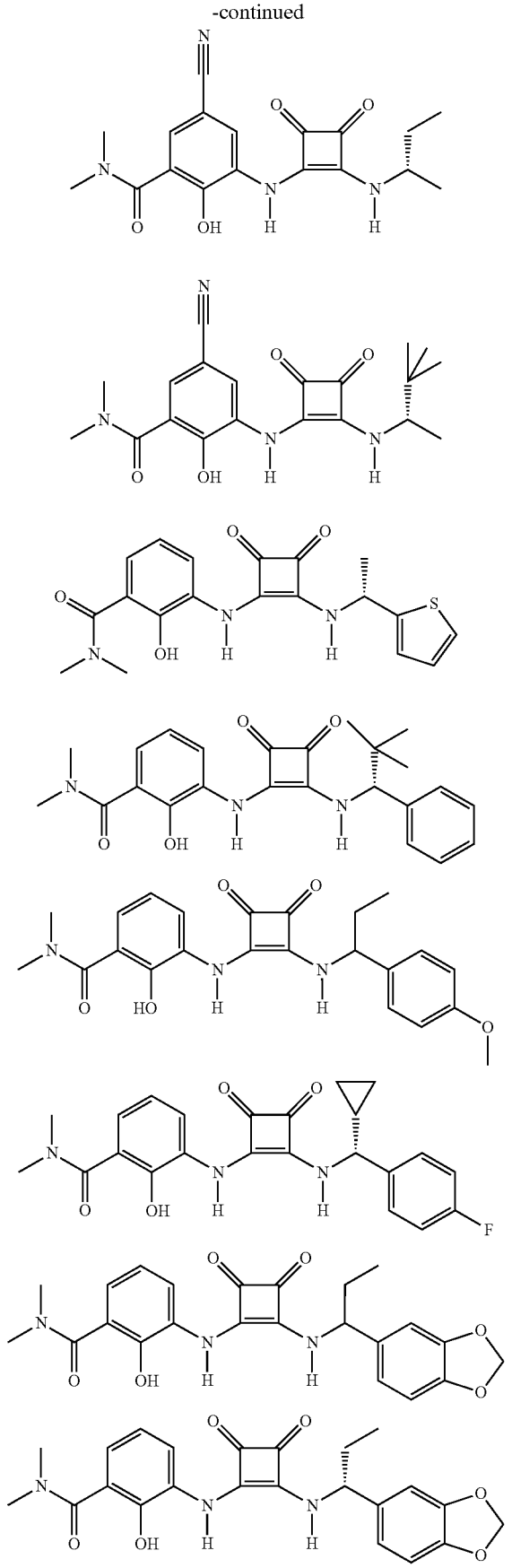
92
-continued
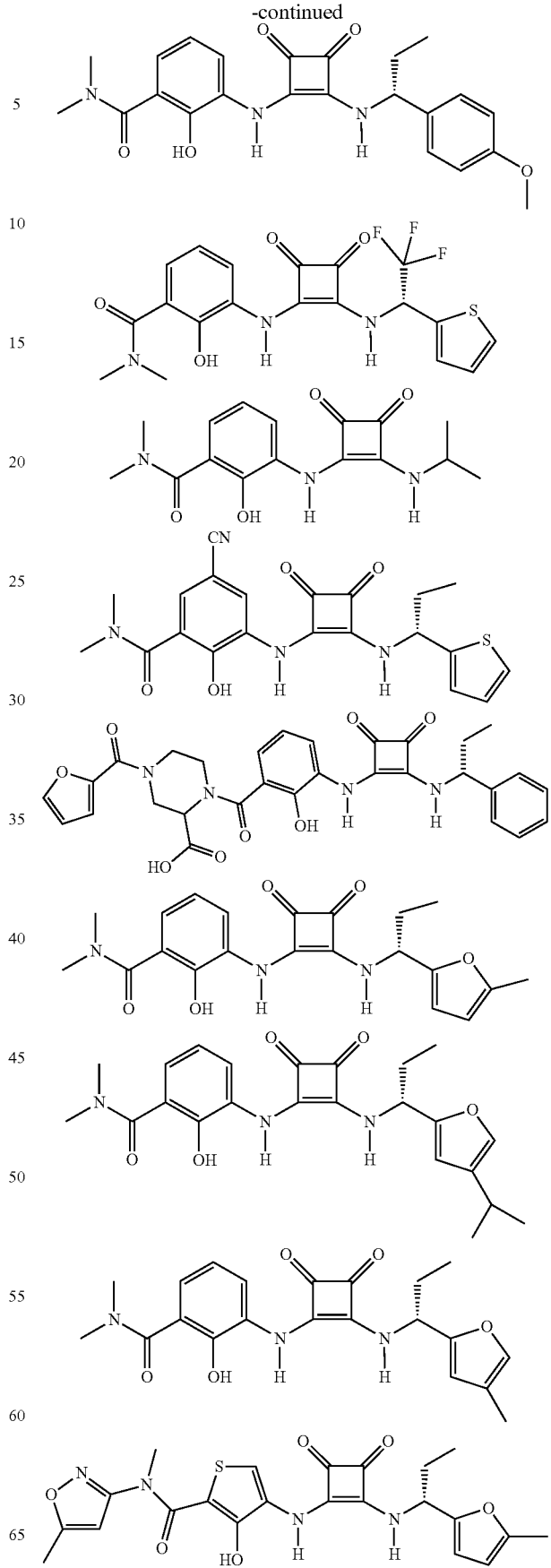

93
-continued
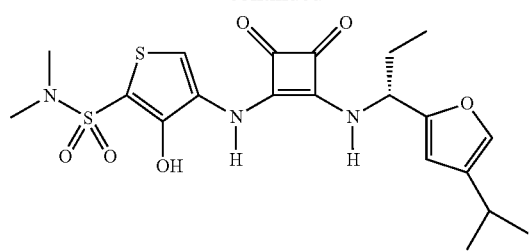
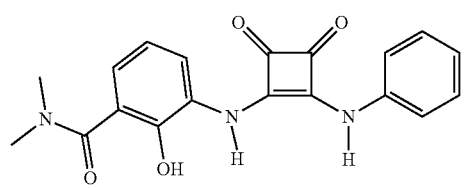
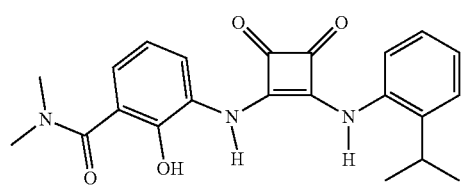
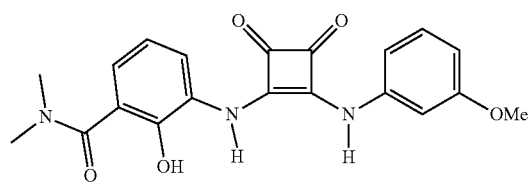
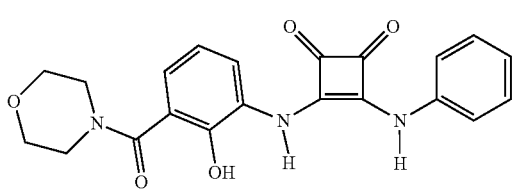
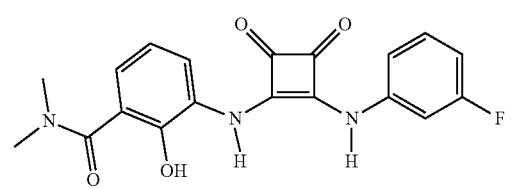
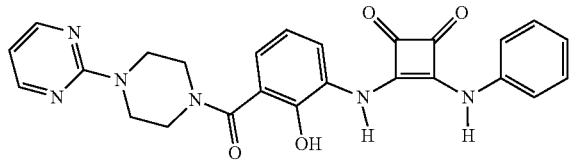
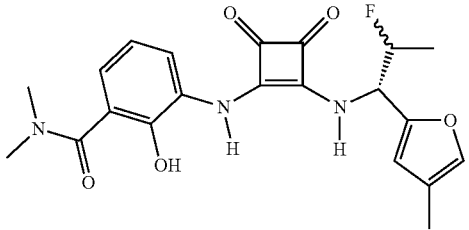
94
-continued
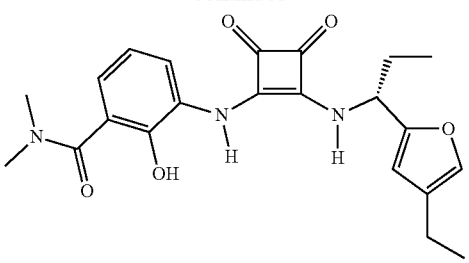
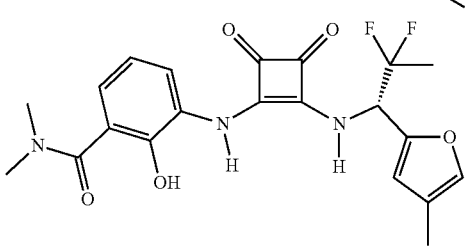
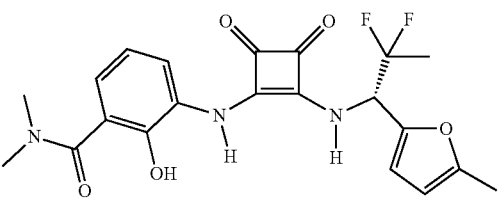
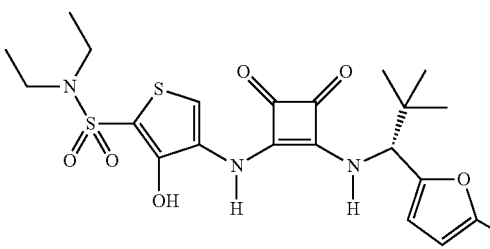
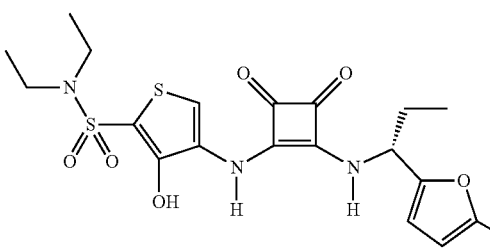
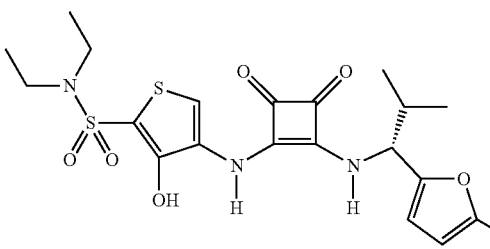
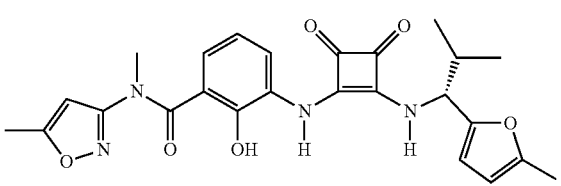

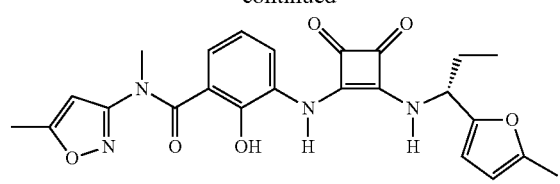
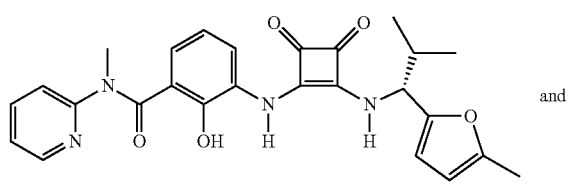
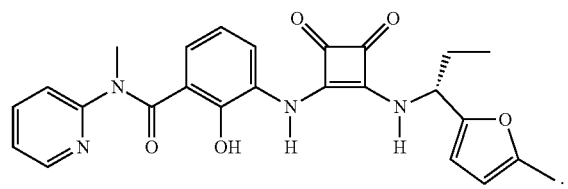
A more preferred group of compounds of formula (I) useful in the methods of this invention include:
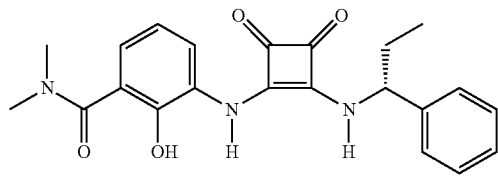
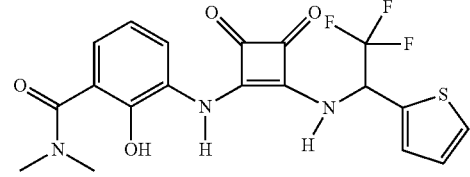
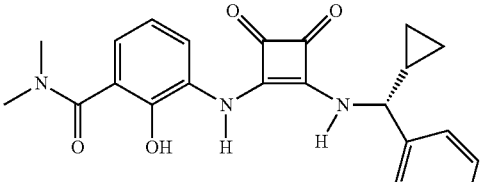
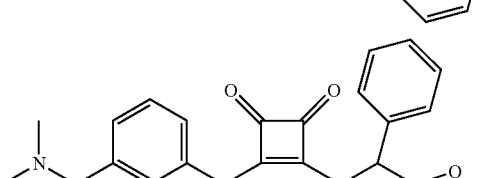
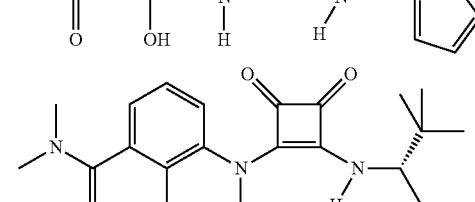
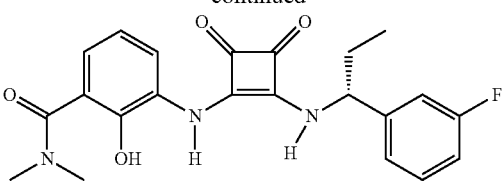
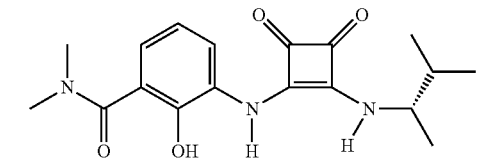
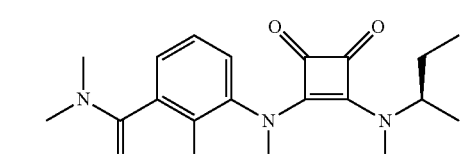
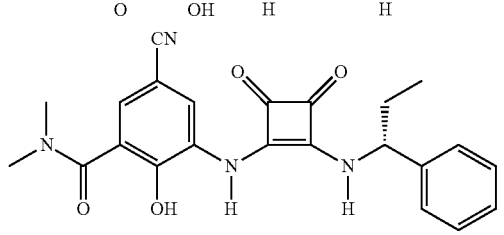
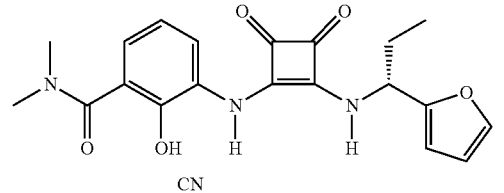
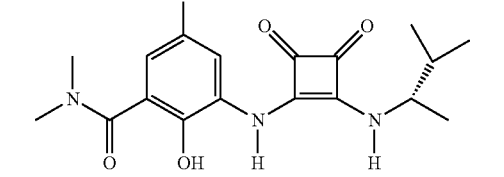
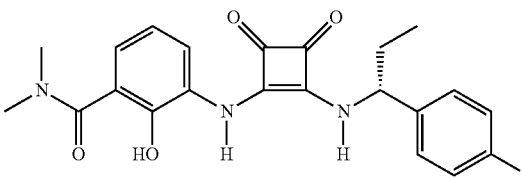

97
-continued
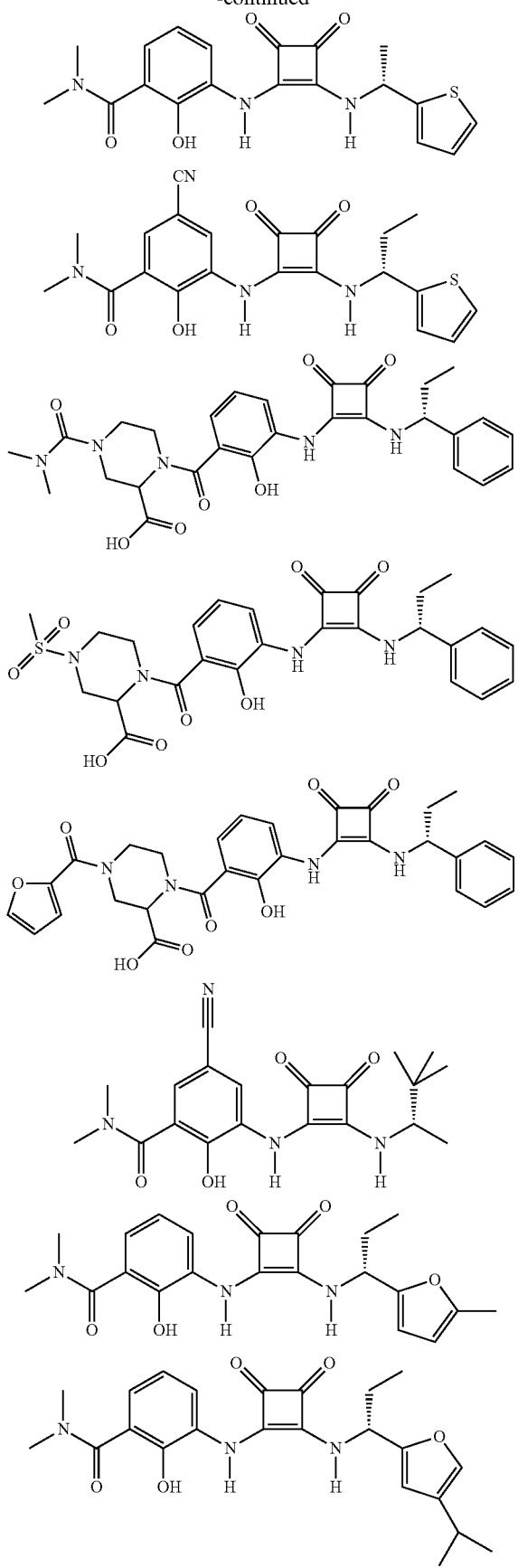
98
-continued
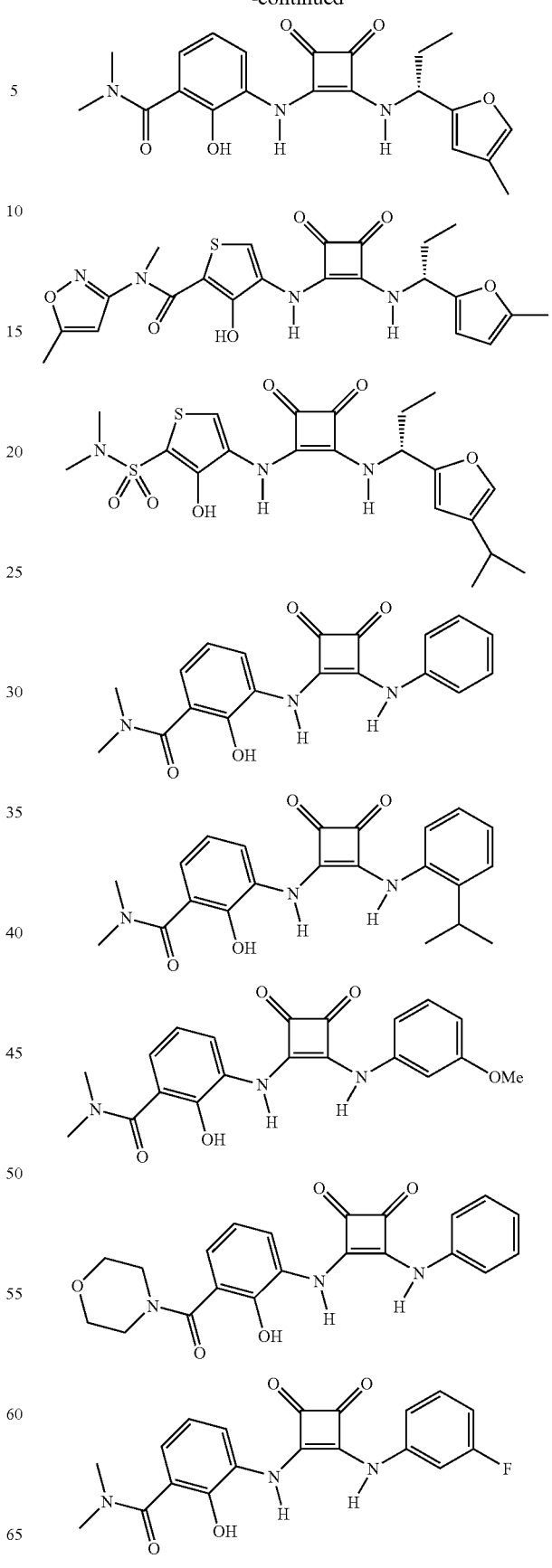

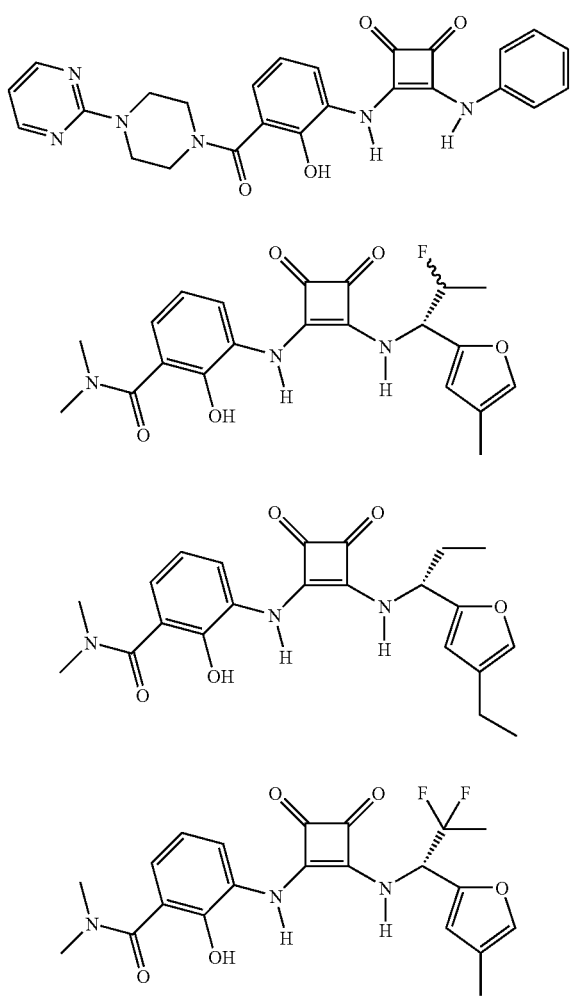
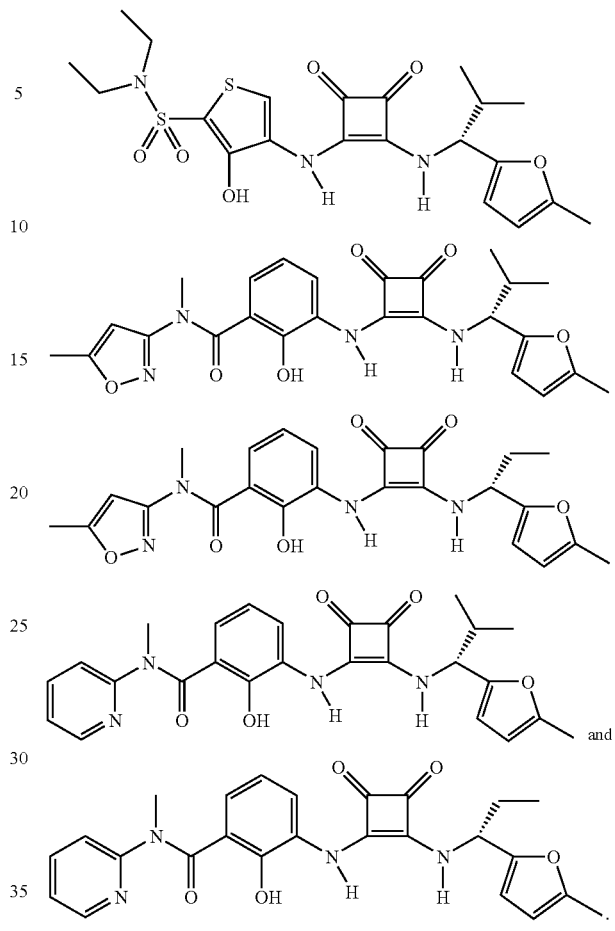
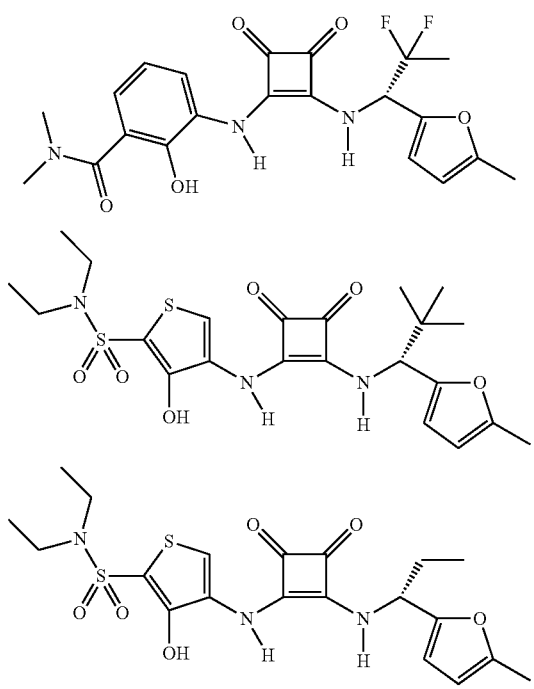
A most preferred group of compounds of formula (I) useful in the methods of this invention include:
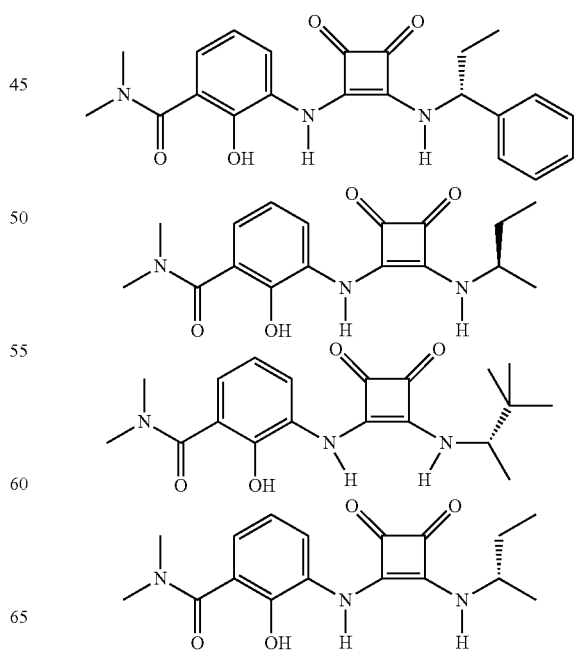

101
-continued
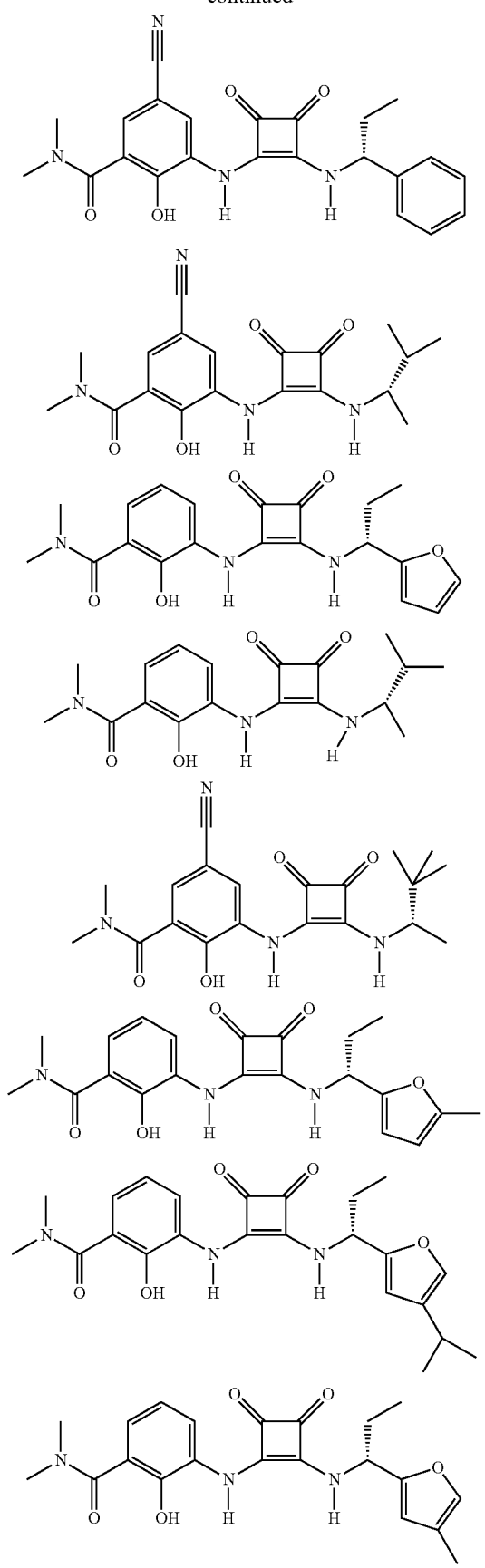
102
-continued
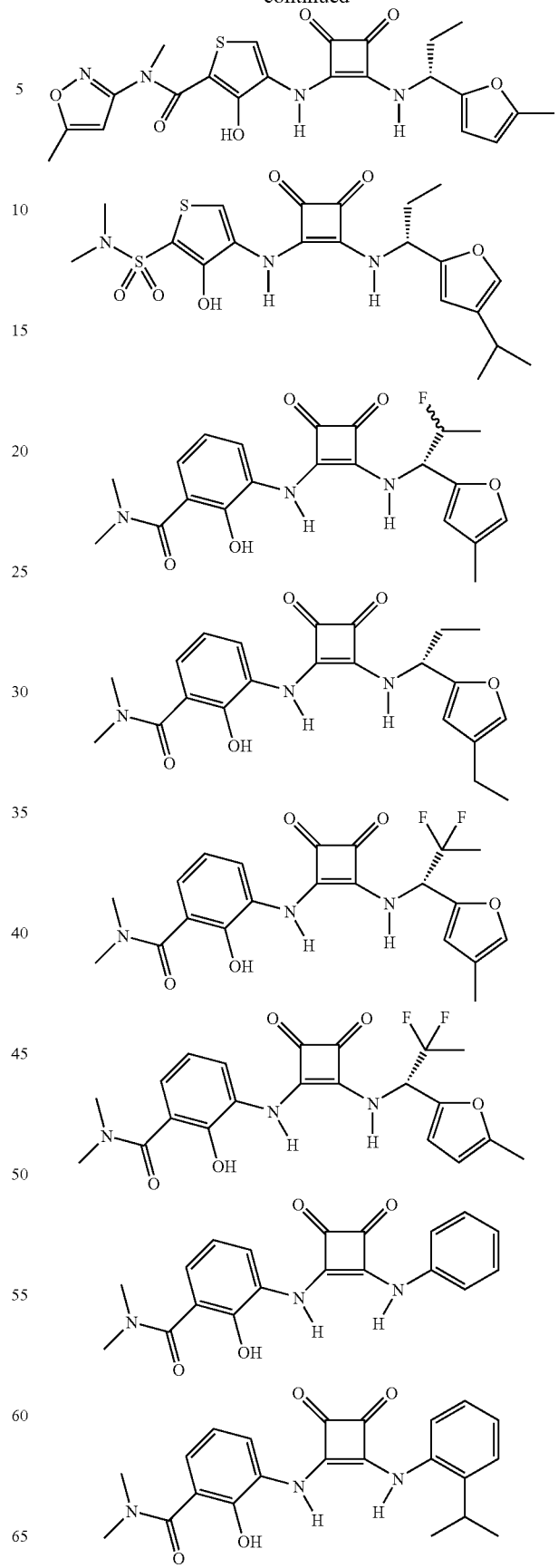

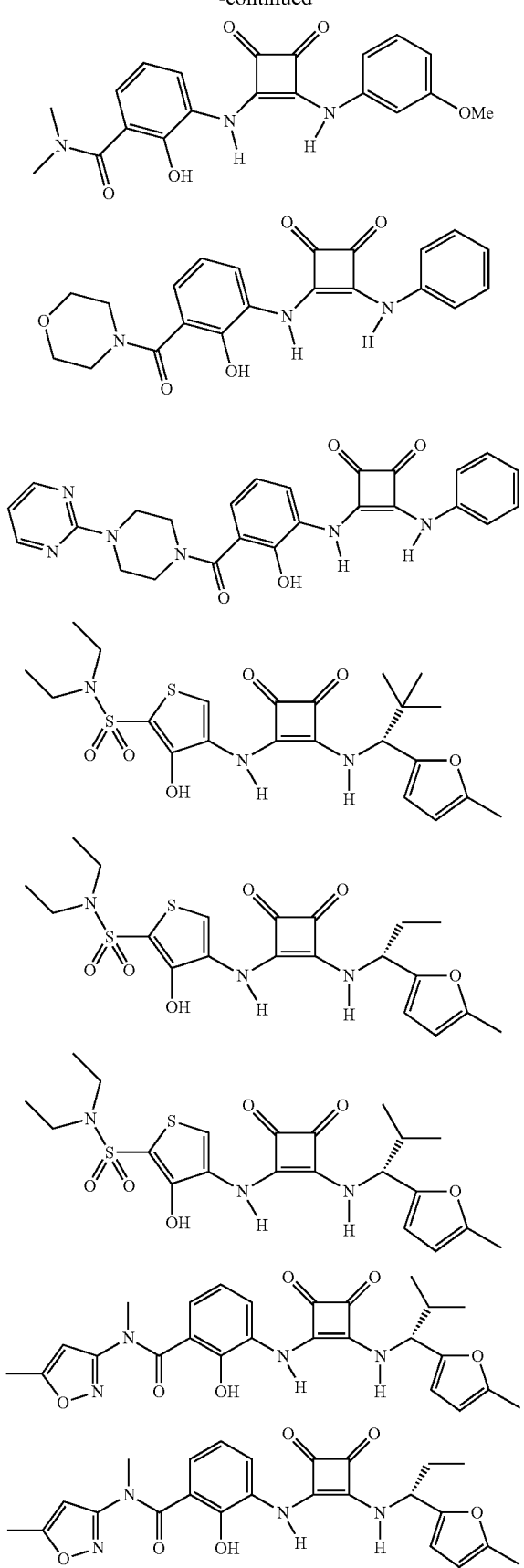

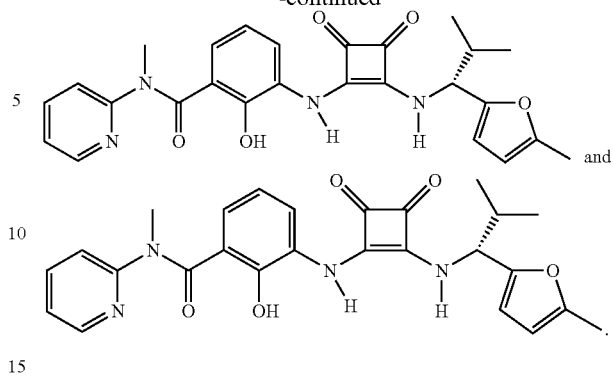

Certain compounds of formula (I) may exist in different stereoisomeric forms (e.g., enantiomers, diastereoisomers and atropisomers). The invention contemplates all such stereoisomers both in pure form and in admixture, including racemic mixtures. Isomers can be prepared using conventional methods.

Certain compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of formula (I) can exist in unsolvated and solvated forms, including hydrated forms. In general, the solvated forms, with pharmaceutically acceptable solvents such as water, ethanol and the like, are equivalent to the unsolvated forms for the purposes of this invention.

This invention also includes Prodrugs of the novel compounds of this invention, and of the compounds of formula (I) useful in the methods of this invention. The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

For preparing pharmaceutical compositions from the compounds of formula (I), inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of formula (I) may also be deliverable transdermally. The transdermal composition can take the form of creams, lotions, aerosols and/or emulsions and can be included in a transdermal patch of the matrix or reservoir type as are conventional in the art for this purpose.

Preferably the compound of formula (I) is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compounds of formula (I) and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The compounds used in combination with the compounds of formula (I) can be administered in their normally prescribed amounts as know by the skilled clinician (see, for example, the Physicians' Desk Reference, 56$^{th}$ edition, 2002, published by Medical Economics company, Inc. at Montvale, N.J. 07645-1742, the disclosure of which is incorporated herein by reference thereto). The amount and frequency of administration of the compounds used in combination with the compounds of formula (I) will be regulated according to the judgment of the attending clinician considering such factors as age, condition and size of the patient as well as severity of the symptoms being treated.

Biological Assays

The compounds of formula (I) are useful in the treatment of CXC-chemokine mediated conditions and diseases. This utility is manifested in their ability to inhibit IL-8 and GRO-α chemokine as demonstrated by the following in vitro assays.

Receptor Binding Assays:

CXCR1 SPA Assay

For each well of a 96 well plate, a reaction mixture of 10 µg hCXCR1-CHO overexpressing membranes (Biosignal) and 200 µg/well WGA-SPA beads (Amersham) in 100 µl was prepared in CXCR1 assay buffer (25 mM HEPES, pH 7.8, 2 mM $CaCl_2$, 1 mM $MgCl_2$, 125 mM NaCl, 0.1% BSA) (Sigma). A 0.4 nM stock of ligand, [125I]-IL-8 (NEN) was prepared in the CXCR1 assay buffer. 20× stock solutions of test compounds were prepared in DMSO (Sigma). A 6× stock solution of IL-8 (R&D) was prepared in CXCR2 assay buffer. The above solutions were added to a 96-well assay plate (PerkinElmer) as follows: 10 µl test compound or DMSO, 40 µl CXCR1 assay buffer or IL-8 stock, 100 µl of reaction mixture, 50 µl of ligand stock (Final [Ligand]=0.1 nM). The assay plates were shaken for 5 minutes on plate shaker, then incubated for 8 hours before cpm/well were determined in Microbeta Trilux counter (PerkinElmer). % Inhibition of Total binding-NSB (250 nM IL-8) was determined for $IC_{50}$ values.

Alternative CXCR1 SPA Assay

Protocol Using CXCR1-Expressing Membranes from Biosignal Packard

For each 50 µl reaction, a working stock of 0.25 µg/µl hCXCR1-CHO overexpressing membranes with a specific activity of 0.05 pmol/mg (Biosignal Packard) and 25 µp/µl WGA-SPA beads (Perkin Elmer Life Sciences) was prepared in CXCR1 assay buffer (25 mM HEPES, pH 7.8, 0.1 mM $CaCl_2$, 1 mM $MgCl_2$, 100 mM NaCl) (Sigma). This mixture was incubated on ice for 30 minutes and then centrifuged at 2500 rpm for 5 minutes. The beads and membranes were resuspended in CXCR1 assay buffer to the same concentrations as in the original mixture. A 0.125 nM stock of ligand, [$^{125}$I]-IL-8 (Perkin Elmer Life Sciences), was prepared in the CXCR1 assay buffer. Test compounds were first serially diluted by half-logs in DMSO (Sigma) and then diluted 20-fold in CXCR1 assay buffer. The above solutions were added to a Corning NBS (non-binding surface) 96-well assay plate as follows: 20 µl test compound or 5% DMSO (final [DMSO]=2%), 20 µl of membranes and SPA bead mixture (Final [membrane]=5 µg/reaction; Final [SPA bead]=500 µg/reaction), 10 µl of ligand stock (Final [$^{125}$I-IL-8]=0.025 nM). The assay plates were incubated for 4 hours before cpm/well were determined in a Microbeta Trilux counter (Perkin Elmer Life Sciences). $IC_{50}$ values were quantified using nonlinear regression analysis in GraphPad Prism.

Alternative CXCR1 SPA Assay
Protocol Using CXCR1-Expressing Membranes from Euroscreen For each 50 μl reaction, a working stock of 0.025 μg/μl hCXCR1-CHO overexpressing membranes with a specific activity of 3.47 pmol/mg (Euroscreen) and 5 μg/μl WGA-SPA beads (Perkin Elmer Life Sciences) was prepared in CXCR1 assay buffer (25 mM HEPES, pH 7.8, 2.0 mM CaCl$_2$, 1 mM MgCl$_2$, 125 mM NaCl) (Sigma). This mixture was incubated on ice for 5 minutes. A 0.125 nM stock of ligand, [$^{125}$I]-IL-8 (Perkin Elmer Life Sciences), was prepared in the CXCR1 assay buffer. Test compounds were first serially diluted by half-logs in DMSO (Sigma) and then diluted 13.3-fold in CXCR1 assay buffer. The above solutions were added to a Corning NBS (non-binding surface) 96-well assay plate as follows: 20 μl test compound or 7.5% DMSO (final [DMSO]= 3%), 20 μl of membranes and SPA bead mixture (Final [membrane]=0.5 μg/reaction; Final [SPA bead]=100 μg/reaction), 10 μl of ligand stock (Final [$^{125}$I-IL-8]=0.025 nM). The assay plates were incubated for 4 hours before cpm/well were determined in a Microbeta Trilux counter (Perkin Elmer Life Sciences). IC$_{50}$ values were quantified using nonlinear regression analysis in GraphPad Prism.

For the CXCR1 assay, compounds of formula (I) had an IC$_{50}$ of <20 μM

CXCR2 SPA Assay

For each well of a 96 well plate, a reaction mixture of 4 μg hCXCR2-CHO overexpressing membranes (Biosignal) and 200 μg/well WGA-SPA beads (Amersham) in 100 μl was prepared in CXCR2 assay buffer (25 mM HEPES, pH 7.4, 2 mM CaCl$_2$, 1 mM MgCl$_2$). A 0.4 nM stock of ligand, [125I]-IL -8 (NEN), was prepared in the CXCR2 assay buffer. 20× stock solutions of test compounds were prepared in DMSO (Sigma). A 6× stock solution of GRO-α (R&D) was prepared in CXCR2 assay buffer. The above solutions were added to a 96-well assay plate (PerkinElmer or Corning) as follows: 10 μl test compound or DMSO, 40 ul CXCR2 assay buffer or GRO-α stock, 100 μl of reaction mixture, 50 μl of ligand stock (Final [Ligand]=0.1 nM). When 40× stock solutions of test compounds in DMSO were prepared, then the above protocol was used except instead 5 μl test compound or DMSO and 45 μl CXCR2 assay buffer were used. The assay plates were shaken for 5 minutes on a plate shaker, then incubated for 2-8 hours before cpm/well were determined in Microbeta Trilux counter (PerkinElmer). % Inhibition of total binding minus non-specific binding (250 nM Gro-α or 50 μM antagonist) was determined and IC50 values calculated. Compounds of formula (I) had an IC$_{50}$ of <5 μM.

Alternative CXCR2 SPA Assay
Protocol Using the CXCR2 50 μl Assay

For each 50 μl reaction, a working stock of 0.031 μg/μl hCXCR2-CHO overexpressing membranes with a specific activity of 0.4 pmol/mg (Biosignal Packard) and 2.5 μg/μl WGA-SPA beads (Perkin Elmer Life Sciences) was prepared in CXCR2 assay buffer (25 mM HEPES, pH 7.4, 2.0 mM CaCl$_2$, 1 mM MgCl$_2$) (Sigma). This mixture was incubated on ice for 5 minutes. A 0.50 nM stock of ligand, [$^{125}$I]-IL-8 (Perkin Elmer Life Sciences), was prepared in the CXCR2 assay buffer. Test compounds were first serially diluted by half-logs in DMSO (Sigma) and then diluted 13.3-fold in CXCR2 assay buffer. The above solutions were added to a Corning NBS (non-binding surface) 96-well assay plate as follows: 20 μl test compound or 7.5% DMSO (final [DMSO]= 3%), 20 μl of membranes and SPA bead mixture (final [membrane]=0.625 μg/reaction; final [SPA bead]=50 μg/reaction), 10 μl of ligand stock (final [$^{125}$I-IL-8]=0.10 nM). The assay plates were incubated for 2 hours before cpm/well were determined in a Microbeta Trilux counter (Perkin Elmer Life Sciences). IC$_{50}$ values were quantified using nonlinear regression analysis in GraphPad Prism.

Alternative CXCR2 SPA Assay
Protocol Using the CXCR2 200 μl Assay

For each 200 μl reaction, a working stock of 0.02 μg/μl hCXCR2-CHO overexpressing membranes with a specific activity of 0.6 pmol/mg (Biosignal Packard) and 2 μg/μl WGA-SPA beads (Perkin Elmer Life Sciences) was prepared in CXCR2 assay buffer (25 mM HEPES, pH 7.4, 2.0 mM CaCl$_2$, 1 mM MgCl$_2$) (Sigma). This mixture was incubated on ice for 5 minutes. A 0.40 nM stock of ligand, [$^{125}$I]-IL -8 (Perkin Elmer Life Sciences), was prepared in the CXCR2 assay buffer. Test compounds were first serially diluted by half-logs in DMSO (Sigma) and then diluted 20-fold in CXCR2 assay buffer. The above solutions were added to a Corning NBS (non-binding surface) 96-well assay plate as follows: 50 μl test compound or 10% DMSO (final [DMSO]= 2.5%), 100 μl of membranes and SPA bead mixture (final [membrane]=2 μg/reaction; final [SPA bead]=200 μg/reaction), 50 μl of ligand stock (final [$^{125}$I-IL-8]=0.10 nM). The assay plates were incubated for 2 hours before cpm/well were determined in a Microbeta Trilux counter (Perkin Elmer Life Sciences). IC$_{50}$ values were quantified using nonlinear regression analysis in GraphPad Prism.

For the CXCR2 assay, compounds of formula (I) had a K$_i$<20 μM.

Carrageenan-Induced Rat Paw Edema Model

Carrageenan (0.05 ml of an 1% solution in saline) was injected into one hindpaw of male Sprague-Dawley rats. Paw volumes (ml) were measured by a water displacement plethysmometer prior to and 3 h after the injection of carrageenan. The increase in paw volume that occurred between the two timepoints was determined for each group. Rats received Compound A:

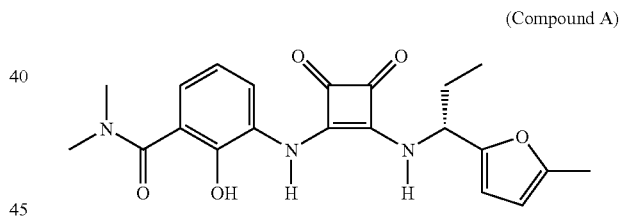

(Compound A)

(see Example 405 of WO 02/083624) or standard drugs in methylcellulose vehicle by the oral route, 1 hr before carrageenan injection. The percentage by which the edematous response was inhibited was calculated by comparing the increase in paw edema of drug-treated rats to that of vehicle-treated controls. To determine neutrophil accumulation in the paws, rats were sacrificed at 3 hrs and myeloperoxidase (MPO) activity was measured from inflammatory fluid expressed from the hindpaw using a colorimetric assay (Bradley et al., 1982). PGE$_2$ production in the hindpaw was assessed by ELISA (R&D Systems, Minneapolis, Minn.).

Combination studies were performed with Compound A and the following standard anti-inflammatory agents—the non-selective anti-inflammatory drug indomethacin, and the steroid betamethasone. The combination of suboptimal doses of compound A at 1 mg/kg (20% inhibition) and indomethacin at 0.5 mg/kg (0% inhibition) caused a significant 41% reduction of paw edema, suggesting that this combination results in greater efficacy than either agent alone. This combination did not cause a further reduction in MPO activity in the hindpaw compared to compound A alone (Compound A=67% inhibition; indomethacin=−58% inhibition; combination=55% inhibition). The combination of suboptimal doses of Compound A at 1 mg/kg and betamethasone at 0.05 mg/kg (32% inhibition) also demonstrated greater efficacy in inhibiting edema (61% inhibition). An additive inhibition of paw PGE$_2$ levels was also observed (31% inhibition by either betamethasone or Compound A alone, versus 78% inhibition with the combination).

Streptococcal Cell Wall-Induced Mouse Knee Swelling Model

The method described by Lubberts et al, 1998 was used for these studies, with some modifications. Female 8-12 week old C57BL/6J animals were fasted overnight and dosed orally with Compound A, indomethacin, or a combination of these agents suspended in methylcellulose one hour prior to a single intra-articular injection of 6 μl containing 25 μg of bacterial SCW (4.32 mg/ml rhammose; Lee Laboratories, Grayson, Ga.) in saline into the right knee joint. The left knee joint received an injection of 6 μl of saline at the same time. In other experiments, a neutralizing rat anti-mouse TNFα antibody or matched rat IgG isotype control was administered intraperitoneally two hours prior to SCW injection and Compound A or methylcellulose vehicle was orally administered one hour prior to SCW injection. Knee swelling measurements were performed 2 hours after SCW injection using a dial-gauge caliper (Starret, Athol, Mass.) by measuring the difference in swelling between the right and left knee joints. Patellar organ cultures for assessment of synovial cytokine and chemokine and prostaglandin levels were prepared at 2 hours after SCW injection and established as described (Lubberts et al, 1998), using ELISA kits obtained from R&D Systems (Minneapolis, Minn.). Statistical analysis was performed using the Student's t-test, with p<0.05 considered to be indicative of statistical significant differences between groups.

Combination therapy with Compound A (10 mg/kg=46% inhibition; 25 mg/kg=70% inhibition) and indomethacin (2 mg/kg=42% inhibition) resulted in significantly greater reduction of knee swelling compared to either agent alone in all instances. Thus, the combination of Compound A at 10 mg/kg with indomethacin resulted in a 74% inhibition of the response, while Compound A at 25 mg/kg in combination with indomethacin led to a 93% inhibition of the swelling response. Compound A administered alone significantly inhibited IL-1β production by ex vivo patellar organ culture (49% inhibition at 10 mg/kg; 64% inhibition at 25 mg/kg) while indomethacin treatment resulted in a 11% inhibition. Combination treatment resulted in a 71% (10 mg/kg Compound A+indomethacin) and 57% inhibition (25 mg/kg Compound A+indomethacin) of IL-1β production, consistent with the concept that the effect on IL-1β was attributable to the pharmacological action of Compound A. In comparison, the effect of combination therapy on PGE$_2$ levels (86% and 85% inhibition, respectively) in patellar organ culture was accounted for by the activity of indomethacin alone (89% inhibition) while Compound A alone had mild activity (34-40% inhibition at 10-25 mg/kg).

REFERENCES

Bradley, P. P., D. A. Priebat, R. D. Christensen and G. Rothstein. 1982. Measurement of cutaneous inflammation: Estimation of neutrophil content with an enzyme marker. *J. Invest. Dermatol.* 78:206-209.

Lubberts, E., L. A. B. Joosten, M. M. A. Helsen and W. B. van den Berg. 1998. Regulatory role of interleukin 10 in joint inflammation and cartilage destruction in murine streptococcal cell wall (SCW) arthritis. More therapeutic benefit with IL-4/IL-10 combination therapy than with IL-10 treatment alone. *Cytokine* 10:361-369.

Compounds of formula (I) may be produced by processes known to those skilled in the art, in the following reaction schemes, and in the preparations and examples below. Specific procedures for the preparation of many of the compounds of formula (I) may be found in in WO 02/076926 published Oct. 3, 2002, and WO 02/083624 published Oct. 24, 2002.

A general procedure for the preparation of compounds of formula (I) is as follows:

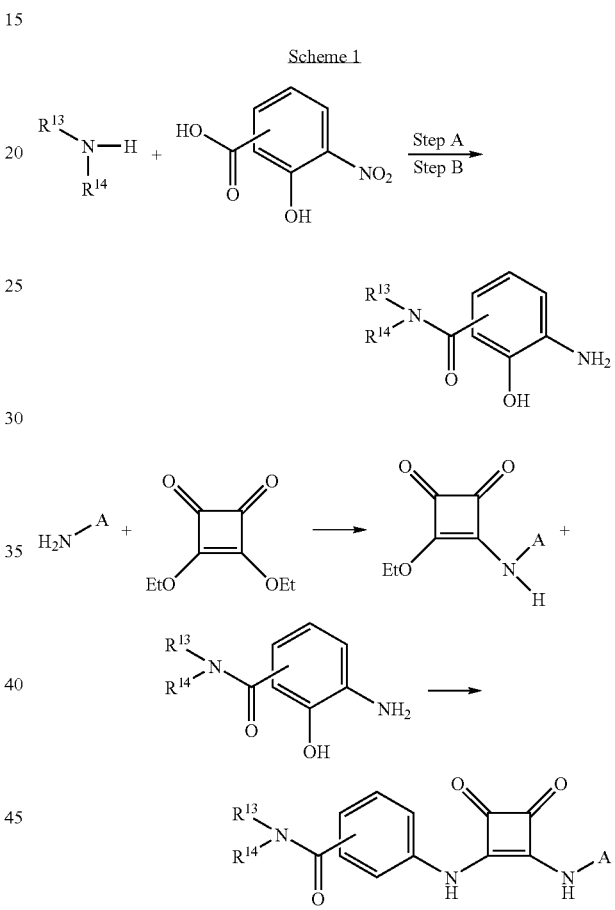

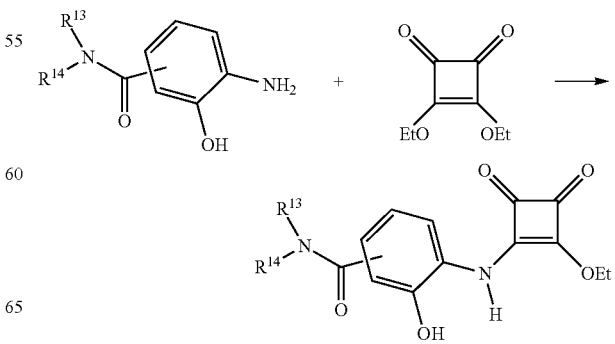

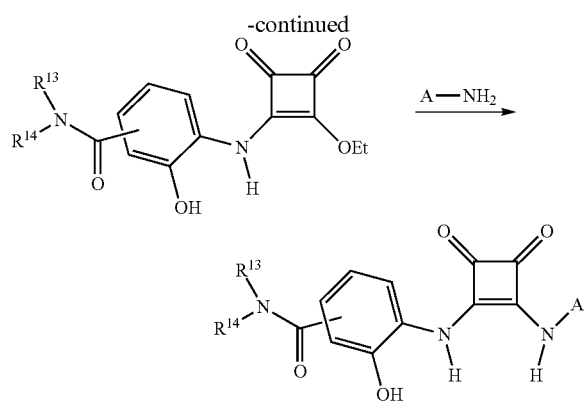

Scheme 1

An amine is condensed (Step A) with a nitrosalicylic acid under standard coupling conditions and the resulting nitrobenzamide is reduced (Step B) under hydrogen atmosphere in the presence of a suitable catalyst. The remaining partner required for the synthesis of the final target is prepared by condensing an aryl amine with the commercially available diethylsquarate to give the aminoethoxysquarate product. Subsequent condensation of this intermediate with the aminobenzamide prepared earlier provides the desired chemokine antagonist (Scheme 1).

Scheme 2

Alternatively, the aminobenzamide of Scheme 1 is first condensed with commercially available diethylsquarate to give an alternate monoethoxy intermediate. Condensation of this intermediate with an amine gives the desired chemokine antagonist.

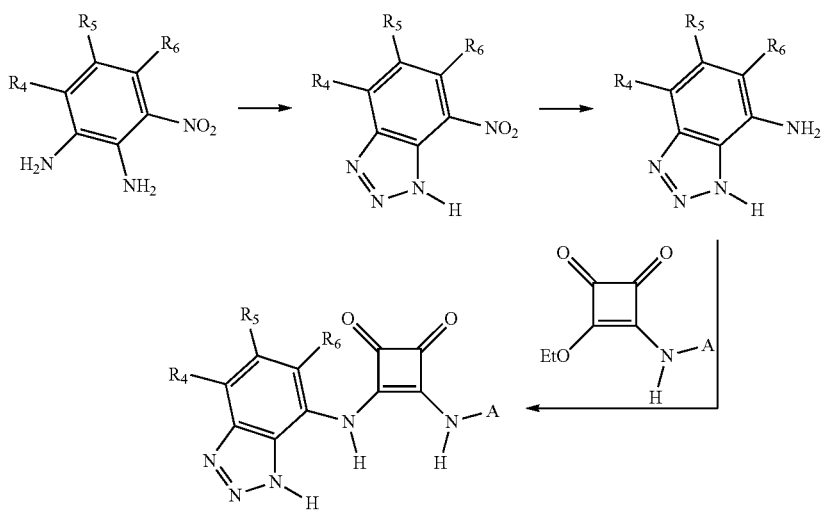

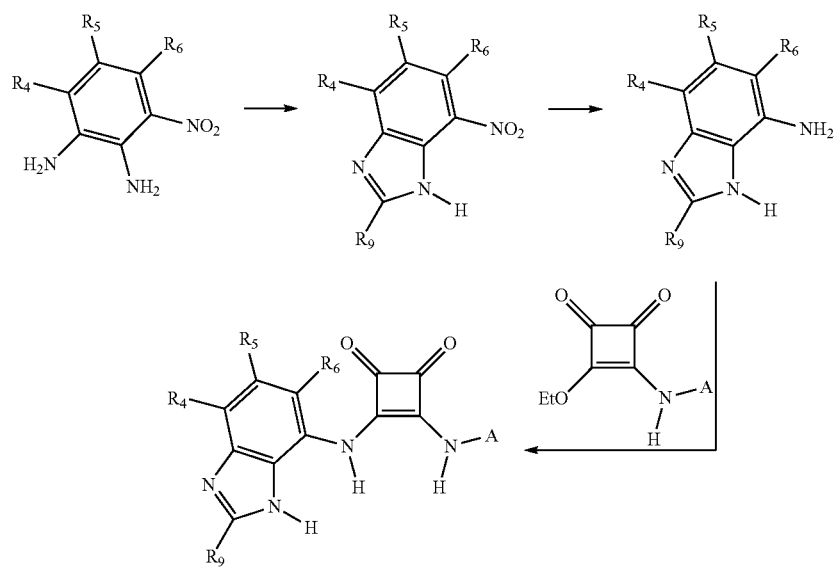

Scheme 3

Benztriazole compounds of Formula (I) are prepared by stirring nitrophenylenediamines with sodium nitrite in acetic acid at 60° C. to afford the nitrobenzotriazole intermediate (Scheme 3). Reduction of the nitro group in the presence of palladium catalyst and hydrogen atmosphere provides the amine compound. Subsequent condensation of this intermediate with the aminooethoxysquarate prepared earlier (Scheme 1) provides the desired chemokine antagonist.

Scheme 4

Condensation of nitrophenylenediamines with anhydrides or activated acids at reflux (Scheme 4) affords benzimidazole intermediates which after reduction with hydrogen gas and palladium catalyst and condensation with the aminoethoxysquarate previously prepared (Scheme 1) affords benzimidazole chemokine antagonists.

Scheme 5

Indazole structures of Formula (I) can be prepared according to Scheme 5 by reduction of nitroindazole A (*J. Am. Chem Soc.* 1943, 65, 1804-1805) to give aminoindazole B and subsequent condensation with the aminoethoxysquarate prepared earlier (Scheme 1).

Scheme 6

Indole structures of Formula (I) can be prepared according to Scheme 6 by reduction of nitroindole A (*J. Med. Chem.* 1995, 38, 1942-1954) to give aminoindole B and subsequent condensation with the aminoethoxysquarate prepared earlier (Scheme 1).

The invention disclosed herein is exemplified by the following preparations and examples which should not be construed to limit the scope of the disclosure. Alternative mechanistic pathways and analogous structures may be apparent to those skilled in the art.

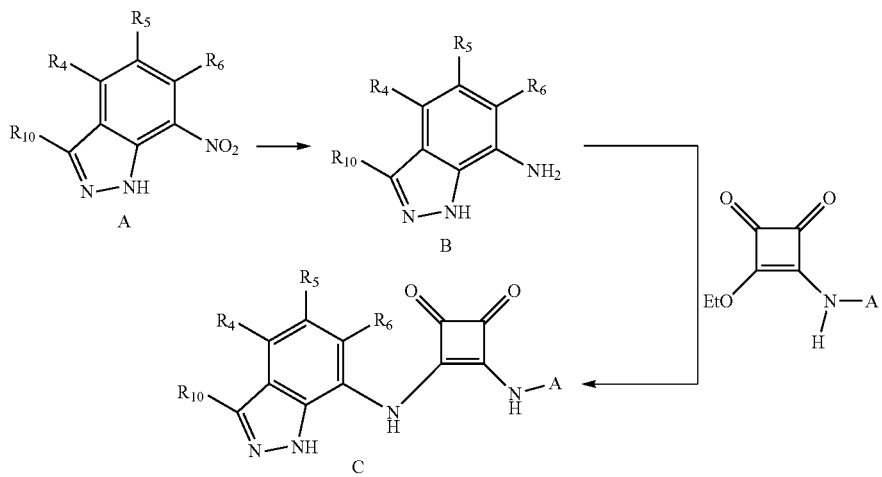

Scheme 5

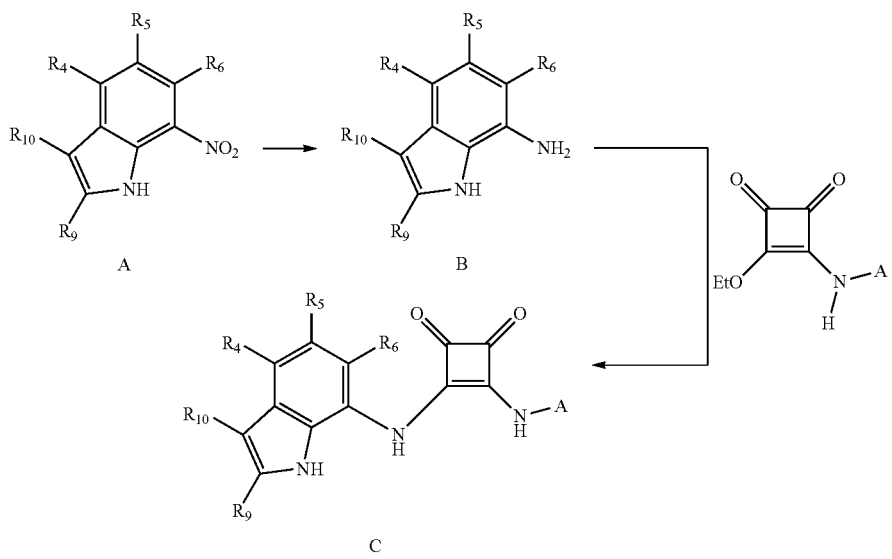

Scheme 6

PREPARATIVE EXAMPLES 13.17A-13.17B

Following the procedure set forth in Preparative Example 13.13 in WO 02/083624, but using the prepared or commercially available aldehydes, the optically pure amine products in the Table below were obtained.

| Prep Ex. | Aldehyde | Amine | Product | Yield (%) |
|---|---|---|---|---|
| 13.17A | 34.8 ![aldehyde with isopropyl furan] | ![amine with CF3, isopropyl furan] | ![ClH·H2N salt with CF3, isopropyl furan] | 38 |
| 13.17B | ![aldehyde with tert-butyl furan] | ![amine with CF3, tert-butyl furan] | ![ClH H2N salt with CF3, tert-butyl furan] | 31 |

PREPARATIVE EXAMPLE 13.29

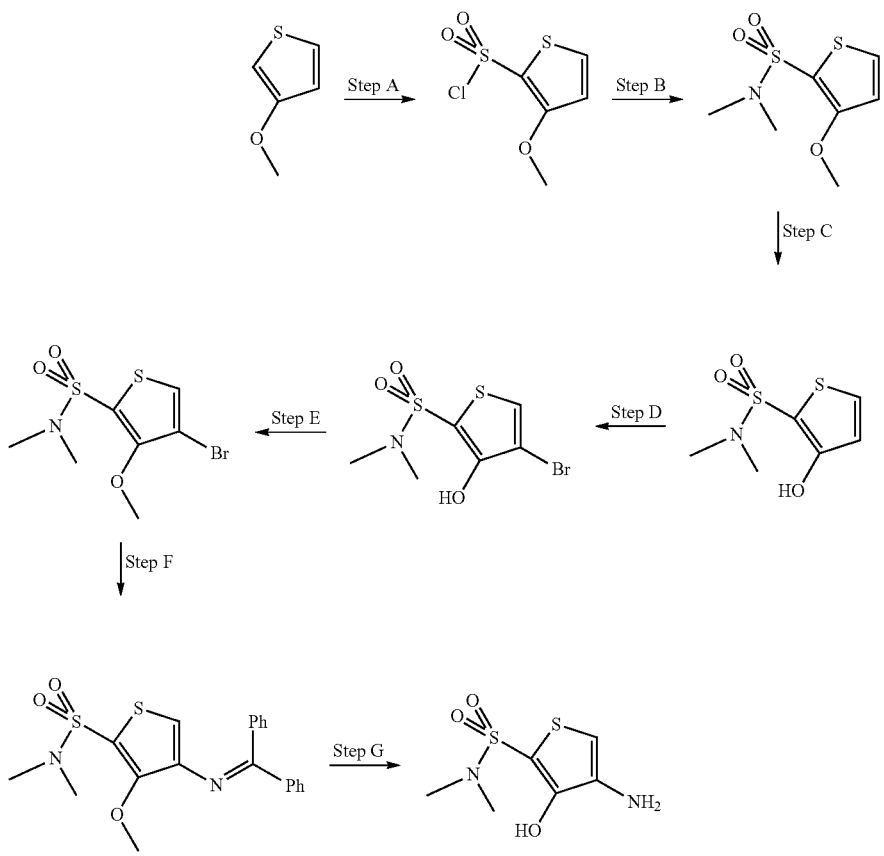

Step A

To a solution of 3-methoxythiophene (3 g) in dichloromethane (175 mL) at −78° C. was added chlorosulfonic acid (8.5 mL) dropwise. The mixture was stirred for 15 min at −78° C. and 1.5 h at room temp. Afterwards, the mixture was poured carefully into crushed ice, and extracted with dichloromethane. The extracts were washed with brine, dried over magnesium sulfate, filtered through a 1-in silica gel pad. The filtrate was concentrated in vacuo to give the desired compound (4.2 g).

Step B

The product from Step A above (4.5 g) was dissolved in dichloromethane (140 mL) and added with triethylamine (8.8 mL) followed by diethyl amine in THF (2M, 21 mL). The resulting mixture was stirred at room temperature overnight. The mixture was washed with brine and saturated bicarbonate (aq) and brine again, dried over sodium sulfate, filtered through a 1-in silica gel pad. The filtrate was concentrated in vacuo to give the desired compound (4.4 g).

Step C

The product from Step B above (4.3 g) was dissolved in dichloromethane (125 mL) and cooled in a −78° C. bath. A solution of boron tribromide (1.0 M in dichloromethane, 24.3 mL) was added. The mixture was stirred for 4 h while the temperature was increased slowly from −78° C. to 10° C. $H_2O$ was added, the two layers were separated, and the aqueous layer was extracted with dichloro-methane. The combined organic layer and extracts were washed with brine, dried over magnesium sulfate, filtered, and concentrated in vacuo to give 3.96 g of the desired hydroxy-compound.

Step D

The product from step C above (3.96 g) was dissolved in 125 mL of dichloromethane, and added with potassium carbonate (6.6 g) followed by bromine (2 mL). The mixture was stirred for 5 h at room temperature, quenched with 100 mL of $H_2O$. The aqueous mixture was adjusted to pH ~5 using a 0.5N hydrogen chloride aqueous solution, and extracted with dichloromethane. The extracts were washed with a 10% $Na_2S_2O_3$ aqueous solution and brine, dried over sodium sulfate, and filtered through a celite pad. The filtrate was concentrated in vacuo to afford 4.2 g of the desired bromo-compound.

Step E

The product from Step D (4.2 g) was dissolved in 100 mL of acetone and added with potassium carbonate (10 g) followed by iodomethane (9 mL). The mixture was heated to reflux and continued for 3.5 h. After cooled to room temperature, the mixture was filtered through a Celite pad. The filtrate was concentrated in vacuo to a dark brown residue, which was purified by flash column chromatography eluting with dichloromethane-hexanes (1:1, v/v) to give 2.7 g of the desired product.

Step F

The product from step E (2.7 g) was converted to the desired imine compound (3 g), following the similar procedure to that of Preparative Example 13.19 step D.

Step G

The imine product from step F (3 g) was dissolved in 80 mL of dichloromethane and cooled in a −78° C. bath. A solution of boron tribromide (1.0 M in dichloromethane, 9.2 mL) was added dropwise. The mixture was stirred for 4.25 h from −78° C. to 5° C. $H_2O$ (50 mL) was added, and the layers were separated. The aqueous layer was extracted with dichloromethane. The organic layer and extracts were combined, washed with brine, and concentrated to an oily residue. The residue was dissolved in 80 mL of methanol, stirred with sodium acetate (1.5 g) and hydroxyamine hydrochloride (0.95 g) at room temperature for 2 h. The mixture was poured into an aqueous mixture of sodium hydroxide (1.0 M aq, 50 mL) and ether (100 mL). The two layers were separated. The aqueous layer was washed with ether three times. The combined ether washings were re-extracted with $H_2O$ once. The aqueous layers were combined, washed once with dichloromethane, adjusted to pH ~6 using 3.0 M and 0.5 M hydrogen chloride aqueous solutions, and extracted with dichloromethane. The organic extracts were combined, washed with brine, dried over sodium sulfate, and concentrated in vacuo to give 1.2 g of desired amine compound.

PREPARATIVE EXAMPLES 13.30-13.32-A

Following the procedures set forth in Example 13.29, but using commercially available amines, hydroxy-aminothiophene products in the Table below were obtained.

| Prep Ex. | Amine | Product | Yield MH+ |
|---|---|---|---|
| 13.30 | (Bn)$_2$NH | Bn,N(Bn)-SO$_2$-thiophene(OH)(NH$_2$) | 10% 375.1 |
| 13.31 | Me(Bn)NH | Bn,N(Me)-SO$_2$-thiophene(OH)(NH$_2$) | 14% 299.0 |
| 13.32 | Et(Bn)NH | Bn,N(Et)-SO$_2$-thiophene(OH)(NH$_2$) | 22% |
| 13.32A | (Et)$_2$NH | Et,N(Et)-SO$_2$-thiophene(OH)(NH$_2$) | 25% |

PREPARATIVE EXAMPLE 13.33

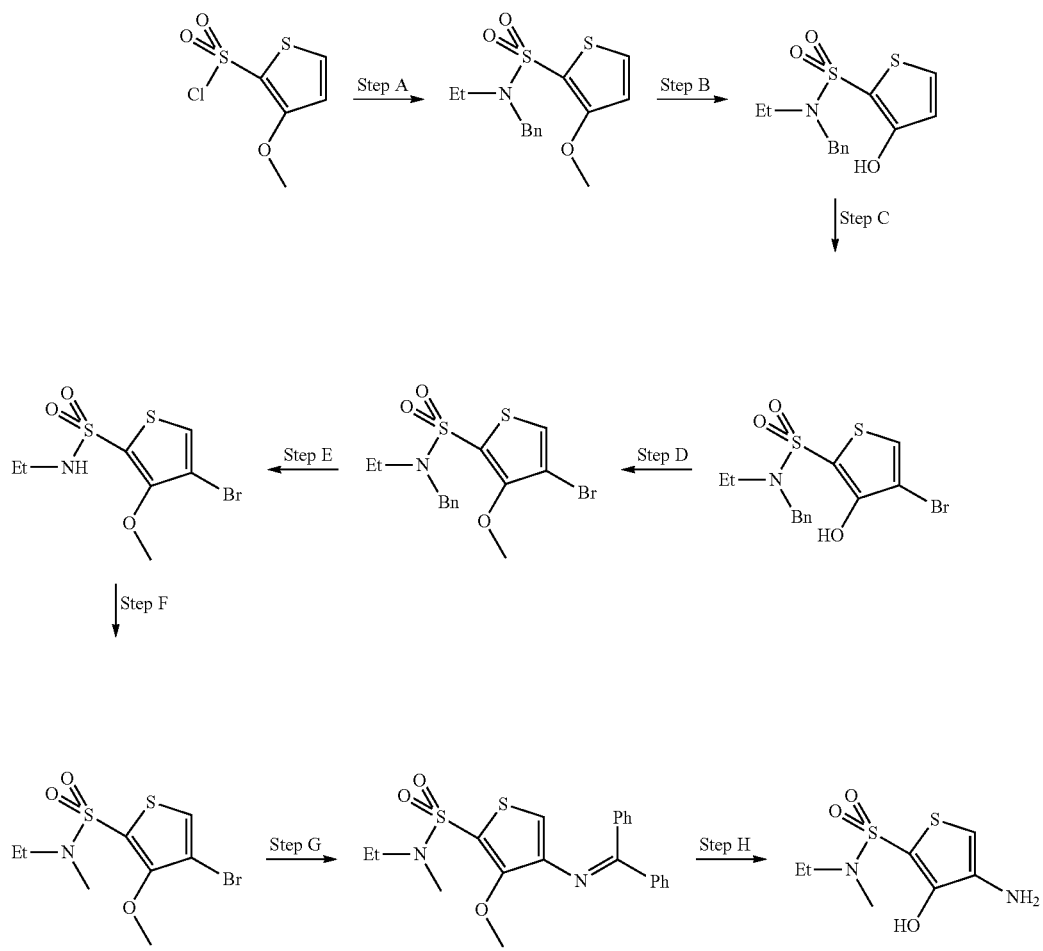

Step A
2-Chlorosulfonyl-3-methoxy-thiophene (4.0 g, 18.8 mmol), the product from Step A of Preparative Example 13.29 was converted to 3-methoxy-2-ethylbenzylsulfonyl-thiophene (5.5 g, 94%, MH$^+$=312.1) by using ethylbenzylamine, following the procedure set forth in Preparative Example 13.29, Step B.

Step B
The product from Step A above (5.5 g, 17.70 mmol) was demethylated following the procedure set forth in Preparative Example 13.29, Step C. The alcohol product was obtained in 4.55 g (87%, MH$^+$=298.0).

Step C
The product from Step B above (4.55 g, 15.30 mmol) was brominated using the procedure set forth in Preparative Example 13.29, Step D. The corresponding bromide was obtained in 4.85 g (84%).

Step D
The bromo-alcohol from Step C above (4.84 g, 12.86 mmol) was methylated using the procedure set forth in Preparative Example 13.29, Step E. The product was obtained in 4.82 g (96%).

Step E
The product from Step D above (4.82 g, 12.36 mmol) was stirred with concentrated sulfuric acid (5 mL) at room temperature ro 3 h. Ice water (30 mL) was added to the mixture followed by CH$_2$Cl$_2$ (50 mL). The aqueous mixture was adjusted to pH ~6 using a 1.0 M NaOH aqueous solution. The layers were separated. The aqueous layer was extracted with CH$_2$Cl$_2$ (50 mL×3). The combined organic layers were washed with brine, dried over Na$_2$SO$_4$, and concentrated to a dark brown oil, which was purified by flash column chromatography, eluting with CH$_2$Cl$_2$-hexanes (1:1, v/v). Removal of solvents afforded 3.03 g (82%) of the debenzylated product (M$^+$=300.0, M+2=302.0).

Step F
The product from Step E (1.34 g, 4.45 mmol) was methylated using the procedure set forth in Preparative Example 13.29, Step E. The desired product was obtained in 1.36 g (97%, M$^+$=314.1, M+2=316.0).

Step G
The product from Step F (1.36 g, 4.33 mmol) was converted to imine product (1.06 g, 55%, MH$^+$=415.1) using the procedure set forth in Preparative Example 13.29, Step F.

Step H
The imine product from Step G (1.06 g, 2.56 mmol) was converted to the desired hydroxy-amino thiophene compound (0.26 g, 43%) using the procedure set forth in Preparative Example 13.29, Step G.

PREPARATIVE EXAMPLE 13.34

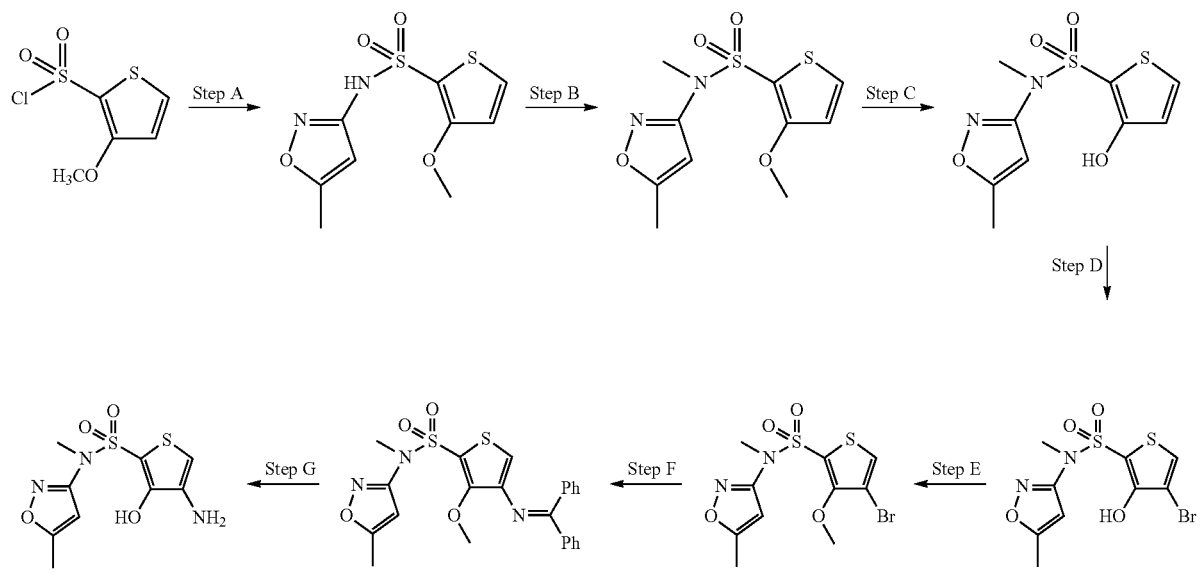

Step A

2-Chlorosulfonyl-3-methoxy-thiophene (3.8 g, 17.87 mmol), the product from step A of Preparative Example 13.29, was dissolved in 100 mL of $CH_2Cl_2$ and 20 mL of pyridine. 3-Amino-5-methyl-isoxazole (3.5 g, 35.68 mmol) was added. The mixture was stirred for 20 h at room temperature, diluted with 100 mL of $CH_2Cl_2$, and washed with a 0.5 N HCl aqueous solution (50 mL×2), $H_2O$ (50 mL), and brine (50 mL). The organic solution was dried with $Na_2SO_4$, and conentrated in vacuo to a brown oil. This oil was dissolved in 100 mL of $CH_2Cl_2$, washed again with a 0.5 M HCl aqueous solution (30 mL×3) and brine. After dried over $Na_2SO_4$, the organic solution was concentrated in vacuo to a yellow solid, 4.48 g (91%, $MH^+=275.0$) of the desired product.

Step B

The product from Step A above (4.48 g, 16.33 mmol) was dissolved in acetone (100 mL), added with potassium carbonate (5.63 g, 40.80 mmol) and iodomethane (10.1 mL, 163.84 mmol). The mixture was stirred at room temperature for 1.5 h, diluted with 100 mL of hexanes and 50 mL of $CH_2Cl_2$, and filtered through a 1-in silica gel pad, rinsing with $CH_2Cl_2$. The filtrate was concentrated under reduced pressure to give 4.23 g (90%, $MH^+=289.0$) of the desired product as a light yellow solid.

Step C

To a stirred suspension of sodium hydride (130 mg, 95%, 5.4 mmol) in 8 mL of N,N'-dimethylforamide at room temperature was added ethanethiol (0.45 mL, 6.0 mmol) dropwise. After 5 min, the mixture became a clear solution, and was added to a stirred solution of the product obtained from Step B above (0.45 g, 1.56 mmol) in 2 mL of N,N'-dimethylforamide in a round bottom flask. The flask was sealed with a ground glass stopper, and the mixture was heated at 90-95° C. for 4 h. After cooled to room temperature, the mixture was poured into 20 mL of a 1.0 M NaOH aqueous solution, further rinsed with 20 mL of $H_2O$. The aqueous mixture was washed with diethyl ether (30 mL×2), adjusted to PH ~5 using a 0.5 M HCl aqueous solution, and extracted with $CH_2Cl_2$ (50 mL×4). The combined extracts were washed with brine, dried ($Na_2SO_4$), and concentrated to a dark yellow solution. This was dissolved in 50 mL of ethyl acetate, washed with $H_2O$ (30 mL×2) and brine (30 mL), dried over $Na_2SO_4$. Evaporation of solvent gave 0.422 g of the alcohol product (99%, $MH^+=275.0$).

Step D

The alcohol obtained from Step C above (0.467 g, 1.70 mmol) was brominated using the procedure set forth in Preparative Example 13.29, Step D, to afford the corresponding bromide in 0.607 g (100%).

Step E

The bromide obtained from Step D above (0.607 g, 1.72 mmol) was methylated using the procedure set forth in Preparative Example 13.29, Step E, to give the desired product in 0.408 g (65%, $M^+=367$, $M+2=369.1$).

Step F

The product (0.405 g, 1.103 mmol) from Step E above was converted to the imine compound (0.29 g, 56%) using the procedure set forth in Preparative Example 13.29, Step F.

Step G

The imine product obtained from Step F above (0.29 g, 0.61 mmol) was demethylated using the procedure set forth in Step C above to give the corresponding alcohol as a dark yellow oil, which was dissolved in 5 mL methanol and added with sodium acetate (0.12 g, 1.46 mmol) and hydroxyamine hydrochloride (0.075 g, 1.08 mmol). The resulting mixture was stirred at room temperature for 3 h, and poured into 10 mL of 1.0 M NaOH aqueous solution. 30 mL of $H_2O$ was used as rinsing and combined to the aqueous layer. The aqueous mixture was washed with diethyl ether (40 mL×3), adjusted to pH ~6 using a 1.0 M HCl aqueous solution, and extracted with ethyl acetate (40 mL×3). The organic extracts were washed with $H_2O$ (20 mL ×2), brine (20 mL), dried over $Na_2SO_4$, and concentrated in vacuo to give 0.112 g of the desired hydroxy-amino thiophene sulfonamide (64%, $MH^+=290$).

PREPARATIVE EXAMPLE 13.35

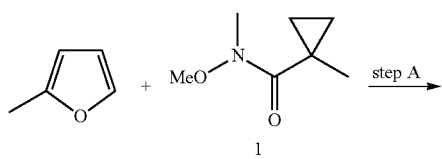

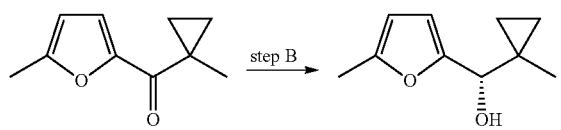

Step A

To a solution of 2-methyl furan (1.72 g) in ether was added BuLi (8.38 mL) at −78° C. and stirred at room temperature for half an hour. The reaction mixture again cooled to −78° C. and quenched with cyclopropyl amide 1 and stirred for two hours at −78° C. and slowly warmed to room temperature. The reaction mixture stirred for three hours at room temperature and quenched with the addition of saturated ammonium chloride solution. The mixture was taken to a separatory funnel, washed with water, brine and dried over anhydrous sodium sulfate. Filtration and removal of solvent afforded the crude ketone, which was purified by using column chromatography to afford the ketone 3.0 g (87%) as a pale yellow oil.

Step B

To a solution of ketone (1.0 g) in THF (5.0 mL) at 0° C. was added R-methyl oxazoborolidine (1.2 mL, 1M in toluene) dropwise followed by addition of a solution of borane complexed with dimethyl sulfide (1.85 mL, 2M in THF). The reaction mixture was stirred for 30 minutes at 0° C. and than at room temperature for one hour. The reaction mixture was cooled to 0° C. and MeOH was added carefully. The mixture was stirred for 20 minutes and was concentrated under reduced pressure. The residue was extracted with ether, washed with water, 1M HCl (10 mL), saturated sodium bicarbonate (10.0 mL) water and brine. The organic layer was dried over anhydrous sodium sulfate, filtered and removal of solvent afforded the crude alcohol which was purified by silica gel chromatography to afford the pure alcohol 0.91 g (91%) as yellow oil.

PREPARATIVE EXAMPLE 13.36

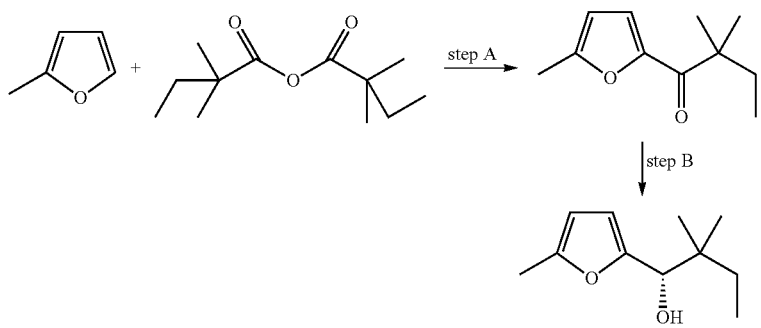

Step A

An equimolar mixture of 2-methylfuran (1.0 g) and anhydride (2.6 g) was mixed with $SnCl_4$ (0.05 mL) and heated at 100° C. for 3 hours. After cooling the reaction mixture, water (10 mL) was added, followed by saturated sodium carbonate solution until it becomes alkaline. The reaction mixture was extracted with ether several times and the combined ether layer was washed with water, brine and dried over anhydrous sodium sulfate. Filtration and removal of solvent afforded the crude ketone, which was purified by using silica gel chromatography to afford the ketone 0.9 g (43%) as a yellow oil.

Step B

The step B alcohol was obtained following a similar procedure set forth in the preparative example 13.35 Step B.

PREPARATIVE EXAMPLE 13.37

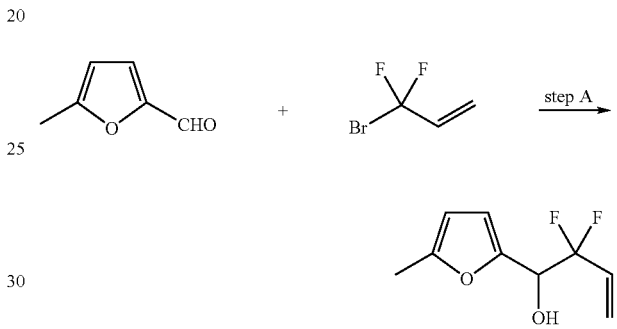

Step A

To a solution of 5-methyl furan-2-aldehyde (1.0 g) and 3-bromo-3,3-difluoropropene (2.24 g) in DMF (30 mL) was added indium powder (1.66 g) and lithium iodide (50.0 mg). The reaction mixture was stirred over night, diluted with water and extracted with ether. The ether layer was washed with water, brine and purified by silicagel chromatography to afford the pure alcohol 2.8 g (92%).

PREPARATIVE EXAMPLES 13.38-13.45

Following a similar procedure set forth in Preparative Examples 13.25 and 13.35, and using the indicated Furan and Electrophile, the following Alcohols in the Table below were prepared.

PREPARATIVE EXAMPLES 13.50-13.61

Following a similar procedure set forth in WO 02/083624, Preparative Example 13.25, and using the indicated Alcohol, the Amines in the Table below were prepared.

| Prep. Ex. | Furan | Electrophile | Alcohol | Yield |
|---|---|---|---|---|
| 13.38 | | | | 86% |
| 13.39 | | | | 69% |
| 13.40 | | | | 84% |
| 13.41 | | | | 82% |
| 13.42 | | | | 60% |
| 13.43 | | | | 65% |
| 13.44 | | | | 82% |
| 13.45 | | | | 89% |

| PREP. EX. | ALCOHOL | AMINE | YIELD |
|---|---|---|---|
| 13.50 | 13.45 | | 28% |
| 13.51 | 13.38 | | 58% |
| 13.52 | 13.36 | | 69% |
| 13.53 | 13.35 | | 81% |
| 13.54 | 13.37 | | 82% |
| 13.55 | 13.39 | | 45% |
| 13.56 | 13.41 | | 57% |

127
-continued

| PREP. EX. | ALCOHOL | AMINE | YIELD |
|---|---|---|---|
| | 13.40 | 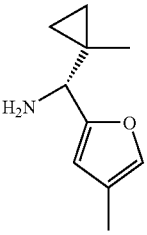 | 58% |
| 13.58 | 13.44 | 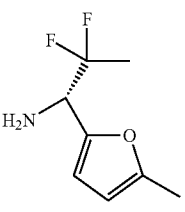 | 54% |
| 13.59 | 13.42 | 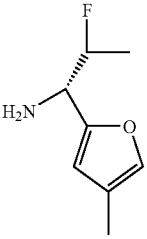 | 53% |

128
-continued

| PREP. EX. | ALCOHOL | AMINE | YIELD |
|---|---|---|---|
| 13.60 | 13.43 | 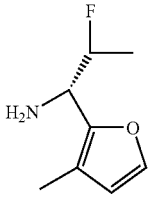 | 50% |
| 13.61 | 13.37 | 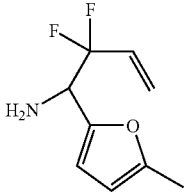 | 82% |

PREPARATIVE EXAMPLE 13.70

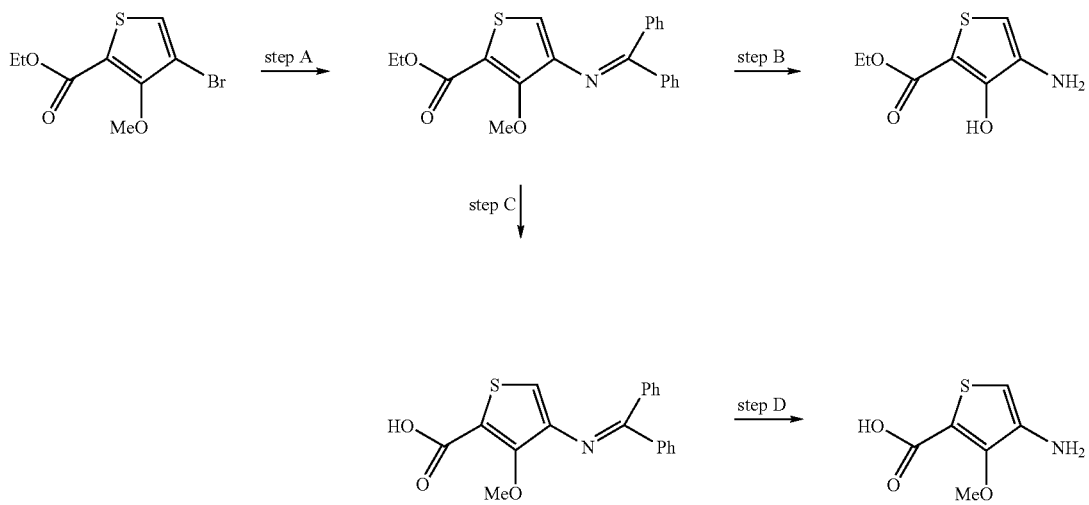

Step A

The imine was prepared following the procedure set forth in WO 02/083624 Preparative Example 13.19 from the known bromoester (1.0 g) as a yellow solid, Step A to yield 1.1 g (79%).

Step B

The Step A product (0.6 g) was reacted following the procedure set forth in the preparative example 13.19 to give the amine product 0.19 g (64%).

Step C

The Step B product (1.0 g) was reacted following the procedure set forth in WO 02/083624 Preparative Example 13.19 to give the acid as yellow solid 0.9 g (94%).

Step D

The Step C product (0.35 g) was reacted following the procedure set forth in WO 02/083624 Preparative Example 13.19 to give the amino acid as yellow solid 0.167 g (93%).

PREPARATIVE EXAMPLE 13.71

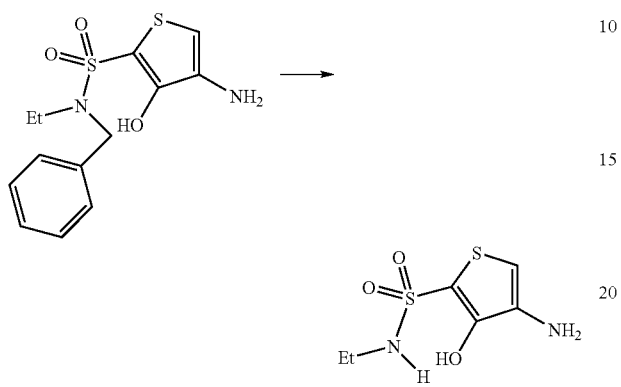

Following a similar procedure set forth in Preparative Example 13.33 Step E, but using the product from WO 02/083624 Preparative Example 13.32, the title compound was obtained (121 mg, 69% yield, MH+=223.0).

PREPARATIVE EXAMPLE 23.15A-23.15E

Following the procedures set forth in WO 02/083624 Preparative Example 19.2 but using the amines from the Preparative Example indicated in the Table below, the corresponding cyclobutenedione intermediates were prepared.

| Prep Ex. | Amine from Prep Ex. | Product | 1. Yield 2. MH+ |
|---|---|---|---|
| 23.15F | 13.32A | 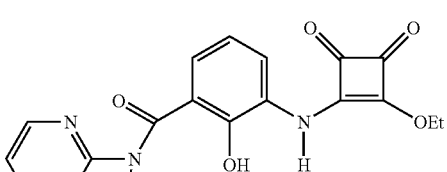 | 1. 68% 2. 375.1 |

PREPARATIVE EXAMPLE 24

Following the procedures set forth in WO 02/083624 Preparative Example 13.23 (but instead using 5-bromo-6-methoxybenzoic acid in Step A) and in WO 02/083624 Preparative Example 23.14, the corresponding cyclobutenedione intermediate could be prepared.

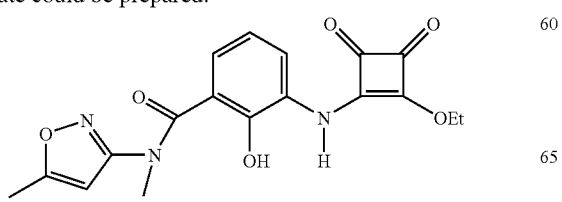

PREPARATIVE EXAMPLE 25

Following the procedures set forth in Preparative Example 13.24 (but instead using 2-aminopyridine) and in WO 02/083624 Preparative Example 23.14, the corresponding cyclobutenedione intermediate could be prepared.

PREPARATIVE EXAMPLE 26

Following the procedures set forth in WO 02/083624 Preparative Example 23.14 (but instead the title compound from WO 02/083624 Preparative Example 135), the corresponding cyclobutenedione intermediate could be prepared.

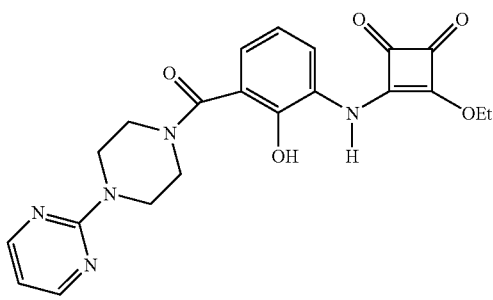

PREPARATIVE EXAMPLE 34.15-34.16

Following the procedures set forth in Preparative Example 34.8 in WO 02/083624 but using the nitroalkanes indicated in the table below, the aldehydes were prepared.

| PREP. Ex. | NITROALKANE | ALDEHYDE | YIELD (%) |
|---|---|---|---|
| 34.15 | cyclopentyl-NO₂ | 4-cyclopentyl-furan-2-carbaldehyde | 17 |
| 34.16 | cyclohexyl-NO₂ | 4-cyclohexyl-furan-2-carbaldehyde | 21 |

PREPARATIVE EXAMPLE 34.17

Step A

To a stirred suspension of 5-bromo-2-furoic acid (15.0 g, 78.54 mmol) in 225 mL of CH₂Cl₂ at room temperature was added oxalyl chloride followed by a catalytic amount of N,N'-dimethylformamide. After 1 h, ethanol (20 mL) was added followed by triethylamine (22 mL). Reaction was continued for 15 h. The mixture was concentrated under reduced pressure to a residue, which was extracted with excess volume of hexanes, and hexanes-CH₂Cl₂ (3:1, v/v). The extracts were filtered, the filtrated was concentrated to a yellow oil, dried on high vacuum, yielding 17.2 g (93%) of the desired ester.

Step B

The ester product obtained from Step A above (17.2 g, 73.18 mmol) was converted to 2-ethyl-4-tertbutyl-5-bromo-furoate (7.9 g, 37%) using the literature procedure: *J. Am. Chem. Soc.*, 1939, 61, 473-478 (the disclosure of which is incorporated herein by reference thereto).

Step C

The ester product obtained from Step B above (7.9 g, 27.13 mol) was reduced to the alcohol (6.32 g) using the procedure set forth in WO 02/083624 Preparative Example 34.8, Step C.

Step D

The product obtained from Step C above (6.32 g) was dissolved in 140 mL of THF and cooled in a −78° C. bath. A 2.5 M solution of n-butyllithium in hexanes (22 mL, 55.0 mmol) was added dropwise along the side wall of the flask. After 15 min, H₂O (~70 mL) was added. Cooling bath was removed, the mixture was stirred for an additional 1 h. Brine (50 mL) and CH₂Cl₂ (300 mL) were added, the two layers were separated, the aqueous layer was extracted with CH₂Cl₂ (100 mL), and the combined organic layers ere dried by Na₂SO₄. Evaporation of solvents afforded 5.33 g (crude) of the debrominated product as a reddish brown oil.

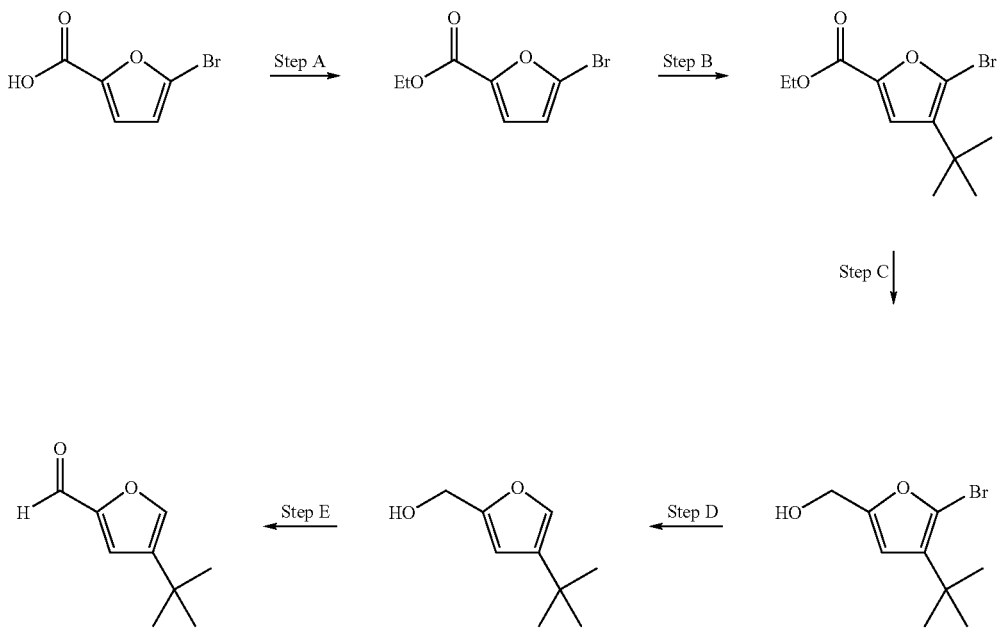

Step E

The alcohol product obtained from Step D above (5.33 g) was oxidized to the corresponding aldehyde (3.06 g, 74%

PREPARATIVE EXAMPLE 34.18

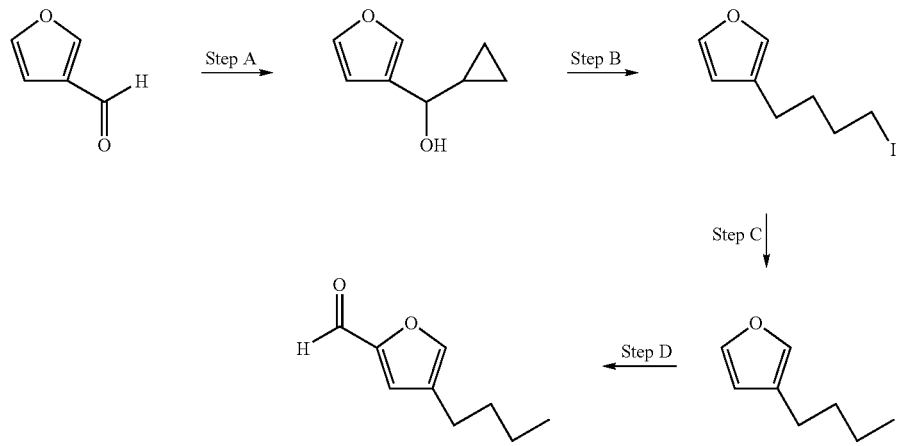

Step A

To a stirred solution of cyclopropyl bromide (4.0 mL, 50 mmol) in 120 mL of ether at −78° C. was added dropwise a 1.7M solution of t-butyllithium in pentane (44.5 mL, 75.7 mmol). After 10 min, cooling bath was removed, stirring was continued for 1.5 h. The mixture was cooled again in a −78° C. bath, and 3-furaldehyde (3.5 mL, 41.9 mmol) was added. Reaction was continued for 1 h, and quenched with a saturated NH4Cl aqueous solution. The aqueous mixture was extracted with $CH_2Cl_2$ (100 mL×3). The organic extracts were washed with brine, dried by $Na_2SO_4$, filtered, and concentrated in vacuo to give 5.3 g (91%) of the alcohol product as a yellow oil.

Step B

Chloro trimethylsilane (27.2 mL, 214.2 mmol) was added dropwise to a vigorously stirred suspension of sodium iodide (32 g, 213.5 mmol) in 100 mL of acetonitrile. After 5 min, a solution of the alcohol obtained from Step A above (4.93 g, 35.68 mmol) in 100 mL of acetonitrile was added dropwise. Stirring was continued for 5 min. $H_2O$ (100 mL) was added, the layers were separated, and the aqueous layer was extracted with ether (100 mL×2). The organic layers were combined, washed with a 10% $Na_2S_2O_3$ aqueous solution and brine, and dried over $Na_2SO_4$. Evaporation of solvents gave a dark brown oil, which was filtered through a 5-in silica gel column, eluting with $CH_2Cl_2$-hexanes (1:3.5, v/v). Removal of solvents afforded 4.22 g (47%) of the iodo product as a light yellow oil.

Step C

The iodo-product obtained from Step B above (2.2 g, 8.8 mmol) was dissolved in 60 mL of ether, and stirred in a −78° C. bath. A 1.7 M solution of t-butyllithium in pentane (10.4 mL, 17.7 mmol) was added dropwise. After 20 min, cooling bath was removed. Reaction was continued for 2.5 h, and quenched with $H_2O$ (20 mL). The aqueous mixture was stirred overnight and separated. The aqueous layer was extracted with ether (30 mL). The combined organic layers were washed with brine, dried by $Na_2SO_4$, and filtered through a Celite pad. Removal of solvent gave 1.10 g (100%) of 3-butylfuran as a reddish-yellow oil.

Step D

3-Butylfuran (1.1 g, 8.8 mmol), obtained from Step C above, was dissolved in 60 mL of ether, and stirred in a −78° C. bath. A 1.7 M solution of t-butyllithium in pentane (6.0 mL, 10.2 mmol) was added dropwise along the side wall of the flask. The mixture was stirred for 3 h from −78° C. to 0° C., and continued for 1 h at room temperature. A solution of N,N'-dimethylforamide (1.1 mL, 14.23 mmol) was added. Reaction was continued overnight, and quenched with a saturated $NH_4Cl$ aqueous solution. The two layers were separated, the aqueous layer was extracted with $CH_2Cl_2$ (30 mL×2). The combined organic layers were washed with brine, dried with $Na_2SO_4$, and concentrated to an oil, which was purified by preparative TLC ($CH_2Cl_2$-hexanes=1:1.5, v/v) to give 0.48 g (36%) of the aldehyde (contaminated by some 3-butyl-2-furaldehyde).

PREPARATIVE EXAMPLE 34.19

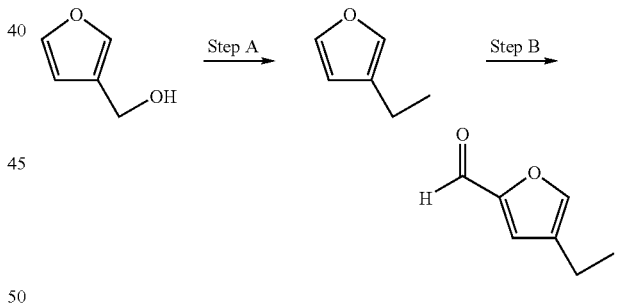

Step A

3-Ethylfuran was prepared from 3-hydroxymethylfuran according to literature procedure: *J. Org. Chem.*, 1983, 48, 1106-1107 (the disclosure of which is incorporated herein by reference thereto).

Step B

3-Ethylfuran obtained from Step A above was converted to 4-ethyl-2-furaldehyde using the procedure set forth in WO 02/083624 Preparative Example 34.18, Step D.

PREPARATIVE EXAMPLES 65-75.10J

Following the procedure set forth in WO 02/083624 Preparative Example 64 but using the aldehydes, amino alcohols, and organolithium reagents in the Table below (prepared according to the Preparative Examples indicated from WO 02/083624), the optically pure amine products in the Table below were obtained.

| Prep Ex. | Aldehyde | Amino Alcohol | Organo lithium | Product | 1. Yield (%) 2. MH+ |
|---|---|---|---|---|---|
| 75.10 N | (34.7) | | Li-cyclopropyl | | 1. 61 2. 135 [M – NH₂]⁺ |
| 75.10 B | (34.19) | | EtLi | | 1. 24 2. 154 |
| 75.10 C | (34.18) | | EtLi | | 1. 32 2. 165 [M – NH₂]⁺ |
| 75.10 D | (34.8) | | MeLi | | 1. 47 2. 137 [M – NH₂]⁺ |
| 75.10 E | (34.8) | | iPrLi | | 1. 30 2. 165 [M – NH₂]⁺ |
| 75.10 F | (34.8) | | Li-cyclopropyl | | 1. 67 2. 163.0 [M – NH₂]⁺ |

-continued

| Prep Ex. | Aldehyde | Amino Alcohol | Organo lithium | Product | 1. Yield (%) 2. MH+ |
|---|---|---|---|---|---|
| 75.10 G | (34.17) 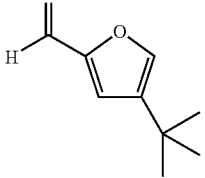 | 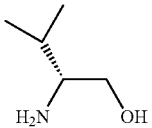 | EtLi | 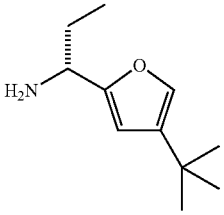 | 1. 24<br>2. 165<br>[M − NH₂]+ |
| 75.10 H | (34.15) 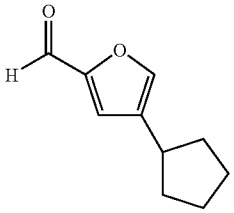 | 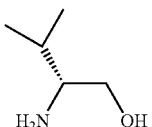 | EtLi | 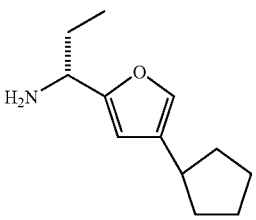 | 1. 70<br>2. 194 |
| 75.10 J | (34.16) 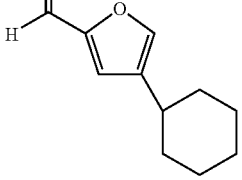 | 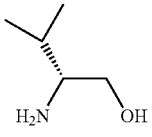 | EtLi | 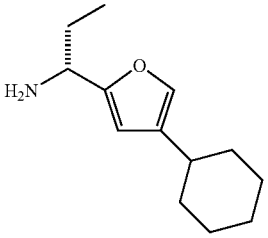 | 1. 54<br>2. 208 |

PREPARATIVE EXAMPLES 75.11-75.59

Following the procedure set forth in WO 02/083624 Preparative Example 64 but using the prepared or commercially available aldehydes, amino alcohols, and organolithium reagents in the Table below and carrying the amine on crude, the optically pure amine products in the Table below were obtained.

| Prep Ex. | Aldehyde | Amine Alcohol | Organo lithium | Product | Yield (%) |
|---|---|---|---|---|---|
| 75.60 | 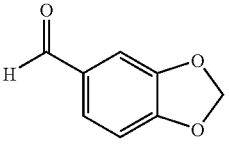 | 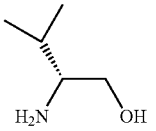 | t-BuLi | 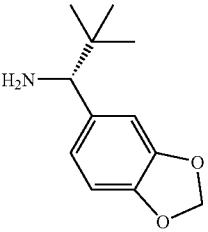 | 60 |

PREPARATIVE EXAMPLE 500.7

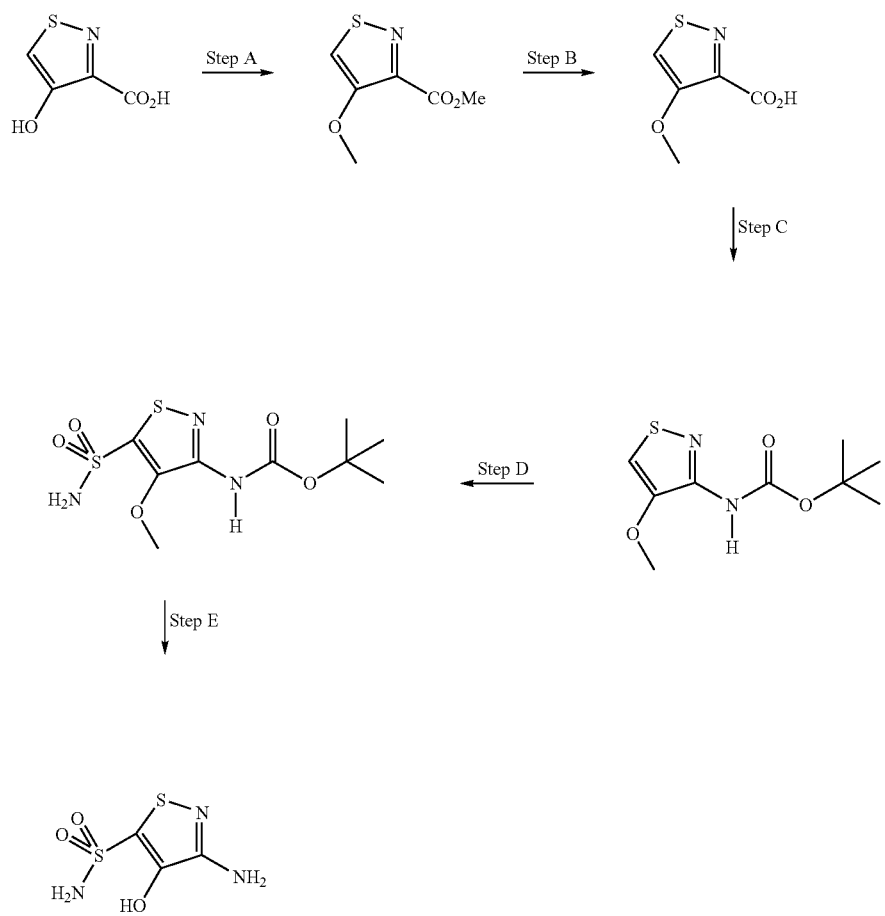

Step A

If one were to use a similar procedure to that used in WO 02/083624 Preparative Example 13.3 Step B, except using the hydroxy acid from *Bioorg. Med. Chem. Lett.* 6(9), 1996, 1043 (the disclosure of which is incorporated herein by reference thereto), one would obtain the desired methoxy compound.

Step B

If one were to use a similar procedure to that used in WO 02/083624 Preparative Example 13.19 Step B, except using the product from Step A above, one would obtain the desired compound.

Step C

If one were to use a similar procedure to that used in *Synth. Commun.* 1980, 10, p. 107 (the disclosure of which is incorporated herein by reference thereto), except using the product from Step B above and t-butanol, one would obtain the desired compound.

Step D

If one were to use a similar procedure to that used in *Synthesis,* 1986, 1031 (the disclosure of which is incorporated herein by reference thereto), except using the product from Step C above, one would obtain the desired sulfonamide compound.

Step E

If one were to use a similar procedure to that used in WO 02/083624 Preparative Example 13.19 Step E, except using the product from Step D above, one would obtain the desired compound.

PREPARATIVE EXAMPLE 500.8

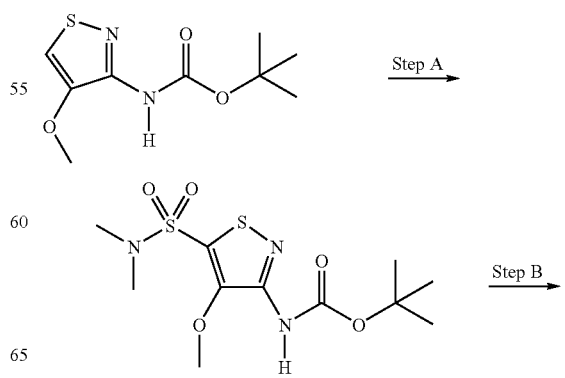

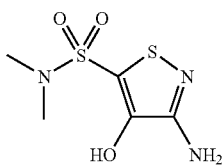

Step A

If one were to treat the product from Step C of WO 02/083624 Example 1125 with BuLi (2.2 eq.) in THF followed by quenching of the reaction mixture with N,N,-dimethylsulfamoyl chloride (1.1 eq.) then one would obtain the title compound.

Step B

If one were to use the product of Step A above and follow Step E of Preparative Example 500.7, then one would obtain the title compound.

PREPARATIVE EXAMPLE 500.9

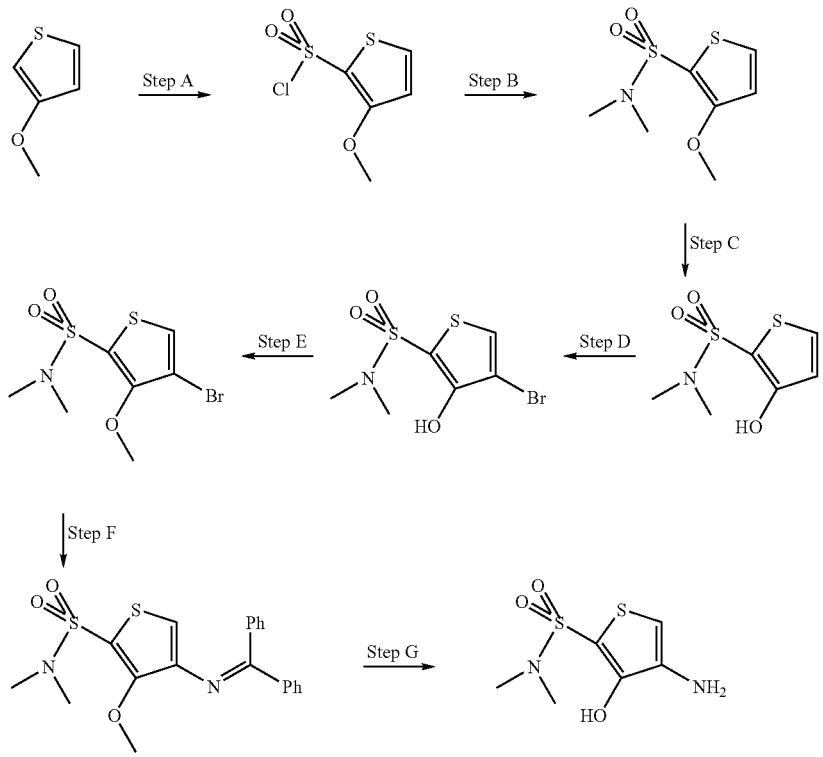

Step A

To a solution of 3-methoxythiophene (3 g) in dichloromethane (175 mL) at −78° C. was added chlorosulfonic acid (8.5 mL) dropwise. The mixture was stirred for 15 min at −78° C. and 1.5 h at room temp. Afterwards, the mixture was poured carefully into crushed ice, and extracted with dichloromethane. The extracts were washed with brine, dried over magnesium sulfate, filtered through a 1-in silica gel pad. The filtrate was concentrated in vacuo to give the desired compound (4.2 g).

Step B

The product from Step A above (4.5 g) was dissolved in dichloromethane (140 mL) and added with triethylamine (8.8 mL) followed by diethyl amine in THF (2M, 21 mL). The resulting mixture was stirred at room temperature overnight. The mixture was washed with brine and saturated bicarbonate (aq) and brine again, dried over sodium sulfate, filtered through a 1-in silica gel pad. The filtrate was concentrated in vacuo to give the desired compound (4.4 g).

Step C

The product from Step B above (4.3 g) was dissolved in dichloromethane (125 mL) and cooled in a −78° C. bath. A solution of boron tribromide (1.0 M in dichloromethane, 24.3 mL) was added. The mixture was stirred for 4 h while the temperature was increased slowly from −78° C. to 10° C. $H_2O$ was added, the two layers were separated, and the aqueous layer was extracted with dichloro-methane. The combined organic layer and extracts were washed with brine, dried over magnesium sulfate, filtered, and concentrated in vacuo to give 3.96 g of the desired hydroxy-compound.

Step D

The product from step C above (3.96 g) was dissolved in 125 mL of dichloromethane, and added with potassium carbonate (6.6 g) followed by bromine (2 mL). The mixture was stirred for 5 h at room temperature, quenched with 100 mL of $H_2O$. The aqueous mixture was adjusted to pH ~5 using a 0.5N hydrogen chloride aqueous solution, and extracted with dichloromethane. The extracts were washed with brine, dried over sodium sulfate, and filtered through a celite pad. The filtrate was concentrated in vacuo to afford 4.2 g of the desired bromo-compound.

Step E

The product from Step D (4.2 g) was dissolved in 100 mL of acetone and added with potassium carbonate (10 g) followed by iodomethane (9 mL). The mixture was heated to reflux and continued for 3.5 h. After cooled to room temperature, the mixture was filtered through a Celite pad. The filtrate was concentrated in vacuo to a dark brown residue, which was purified by flash column chromatography eluting with dichloromethane-hexanes (1:1, v/v) to give 2.7 g of the desired product.

Step F

The product from step E (2.7 g) was converted to the desired imine compound (3 g), following the similar procedure to that of WO 02/083624 Preparative Example 13.19 step D.

Step G

The imine product from step F (3 g) was dissolved in 80 mL of dichloromethane and cooled in a −78° C. bath. A solution of boron tribromide (1.0 M in dichloromethane, 9.2 mL) was added dropwise. The mixture was stirred for 4.25 h from −78° C. to 5° C. $H_2O$ (50 mL) was added, and the layers were separated. The aqueous layer was extracted with dichloromethane. The organic layer and extracts were combined, washed with brine, and concentrated to an oily residue. The residue was dissolved in 80 mL of methanol, stirred with sodium acetate (1.5 g) and hydroxyamine hydrochloride (0.95 g) at room temperature for 2 h. The mixture was poured into an aqueous mixture of sodium hydroxide (1.0 M aq, 50 mL) and ether (100 mL). The two layers were separated. The aqueous layer was washed with ether three times. The combined ether washings were re-extracted with $H_2O$ once. The aqueous layers were combined, washed once with dichloromethane, adjusted to pH ~6 using 3.0 M and 0.5 M hydrogen chloride aqueous solutions, and extracted with dichloromethane. The organic extracts were combined, washed with brine, dried over sodium sulfate, and concentrated in vacuo to give 1.2 g of desired amine compound.

PREPARATIVE EXAMPLE 600

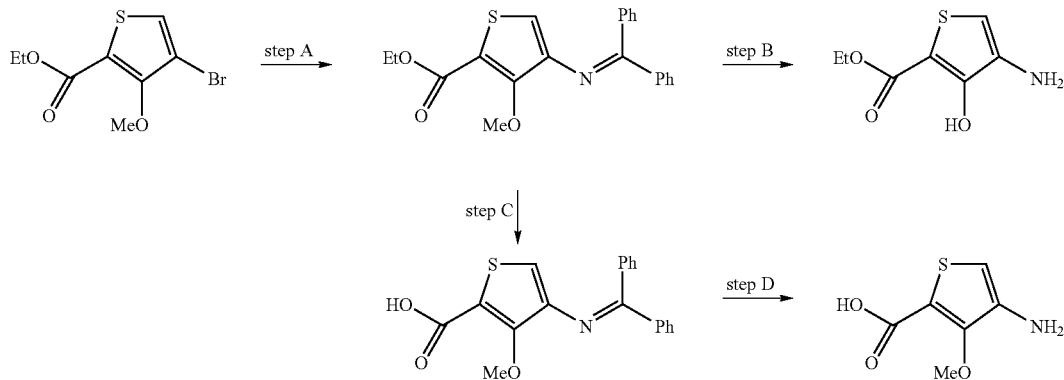

Step A

Following the procedure set forth in WO 02/083624 Preparative Example 13.19 Step D, the imine was prepared from the known bromoester (1.0 g) to yield 1.1 g (79%) as a yellow solid.

Step B

The product of Step A (0.6 g) was reacted following the procedure set forth in WO 02/083624 Preparative Example 13.19 Step E to give the amine product 0.19 g (64%).

Step C

The product of Step B (1.0 g) was reacted following the procedure set forth in WO 02/083624 Preparative Example 13.19 Step B to give the acid as yellow solid 0.9 g (94%).

Step D

The product of Step C (0.35 g) was reacted following the procedure set forth in WO 02/083624 Preparative Example 13.19 Step E to give the amino acid as yellow solid 0.167 g (93%).

PREPARATIVE EXAMPLE 601

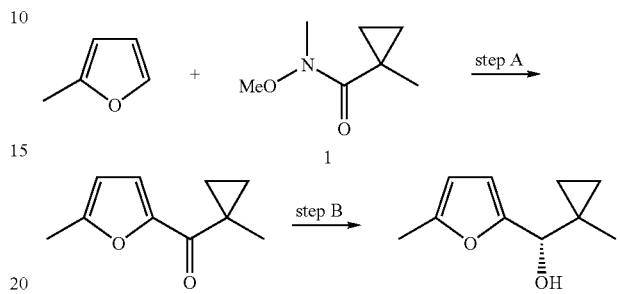

Step A

To a solution of 2-methyl furan (1.72 g) in ether was added BuLi (8.38 mL) at −78° C. and stirred at room temperature for half an hour. The reaction mixture again cooled to −78° C. and quenched with cyclopropyl amide 1 and stirred for two hours at −78° C. and slowly warmed to room temperature. The reaction mixture stirred for three hours at room temperature and quenched with the addition of saturated ammonium chloride solution. The mixture was taken to a separatory funnel, washed with water, brine and dried over anhydrous sodium sulfate. Filtration and removal of solvent afforded the crude ketone, which was purified by using column chromatography to afford the ketone 3.0 g (87%) as a pale yellow oil.

Step B

To a solution of ketone (1.0 g) from Step A above in THF (5.0 mL) at 0° C. was added R-methyl oxazoborolidine (1.2 mL, 1M in toluene) dropwise followed by addition of a solution of borane complexed with dimethyl sulfide (1.85 mL, 2M in THF). The reaction mixture was stirred for 30 minutes at 0° C. and than at room temperature for one hour. The reaction mixture was cooled to 0° C. and MeOH was added carefully. The mixture was stirred for 20 minutes and was concentrated under reduced pressure. The residue was extracted with ether, washed with water, 1M HCl (10 mL), saturated sodium bicarbonate (10.0 mL) water and brine. The organic layer was dried over anhydrous sodium sulfate, filtered and removal of solvent afforded the crude alcohol which was purified by silica gel chromatography to afford the pure alcohol 0.91 g (91%) as yellow oil.

PREPARATIVE EXAMPLE 602

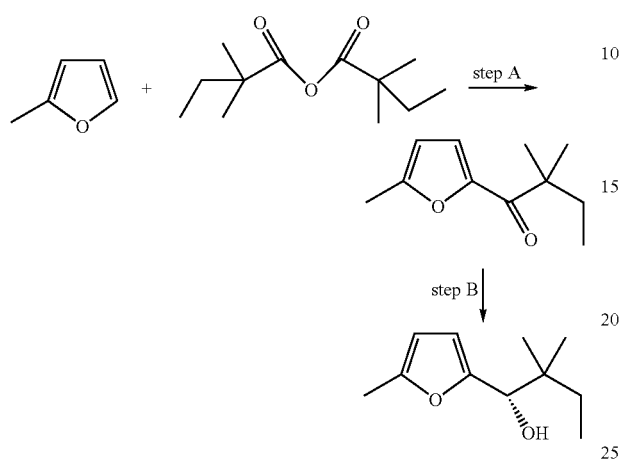

Step A
An equimolar mixture of 2-methylfuran (1.0 g) and anhydride (2.6 g) was mixed with SnCl$_4$ (0.05 mL) and heated at 100° C. for 3 hours. After cooling the reaction mixture, water (10 mL) was added, followed by saturated sodium carbonate solution until it becomes alkaline. The reaction mixture was extracted with ether several times and the combined ether layer was washed with water, brine and dried over anhydrous sodium sulfate. Filtration and removal of solvent afforded the crude ketone, which was purified by using silica gel chromatography to afford the ketone 0.9 g (43%) as a yellow oil.
Step B
The title alcohol was obtained following a similar procedure set forth in Preparative Example 601.

PREPARATIVE EXAMPLE 603

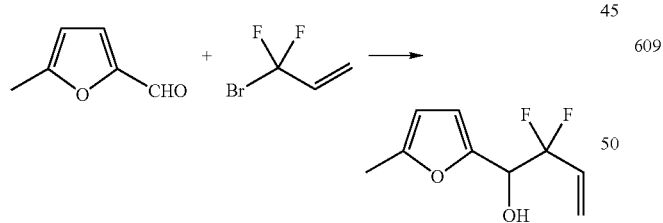

To a solution of 5-methyl furan-2-aldehyde (1.0 g) and 3-bromo-3,3-difluoropropene (2.24 g) in DMF (30 mL) was added indium powder (1.66 g) and lithium iodide (50.0 mg). The reaction mixture was stirred over night, diluted with water and extracted with ether. The ether layer was washed with water, brine and purified by silica gel chromatography to afford the pure alcohol 2.8 g (92%).

PREPARATIVE EXAMPLES 604-611

Following a similar procedure set forth in WO 02/083624 Preparative Examples 13.25 or 601 the following Alcohols were prepared.

| Prep Ex | Furan | Electrophile | Alcohol | Yield |
|---|---|---|---|---|
| 604 | 2-methylfuran | (CH$_3$)$_3$CCH$_2$CHO | corresponding alcohol | 86% |
| 605 | 2-methylfuran | CH$_3$CHFCOOEt | corresponding alcohol | 69% |
| 606 | 3-methylfuran | 1-methylcyclopropyl Weinreb amide | corresponding alcohol | 84% |
| 607 | 3-methylfuran | 1-methylcyclopropyl Weinreb amide | corresponding alcohol | 82% |
| 608 | 3-methylfuran | CH$_3$CHFCOOEt | corresponding alcohol | 60% |
| 609 | 3-methylfuran | CH$_3$CHFCOOEt | corresponding alcohol | 65% |
| 610 | 2-methylfuran | CF$_2$(CH$_3$) Weinreb amide | corresponding alcohol | 82% |
| 611 | 2-methylfuran | OHCCH$_2$CF$_3$ | corresponding alcohol | 89% |

PREPARATIVE EXAMPLES 620-631

Following a similar procedure to that set forth in WO 02/083624 Preparative Example 13.25 the following Amines were prepared from the corresponding Alcohols.

| Prep Ex | ALCOHOL | AMINE | % YIELD |
|---|---|---|---|
| 620 | | | 28 |
| 621 | | | 58 |
| 622 | | | 69 |
| 623 | | | 81 |
| 624 | | | 82 |
| 625 | | | 45 |
| 626 | | | 57 |
| 627 | | | 58 |
| 628 | | | 54 |
| 629 | | | 53 |
| 630 | | | 50 |
| 631 | | | 82% |

PREPARATIVE EXAMPLE 640-641

Following the procedures set forth in WO 02/083624 Preparative Example 19 but using the amine from the Preparative Example indicated in the Table below, the cyclobutenedione intermediates were obtained.

| Ex. | Amine Prep from Prep Ex. | Product | 1. Yield 2. MH+ |
|---|---|---|---|
| 640 | 600 Step B | 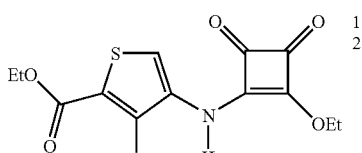 | 1. 60% 2. 138 |
-continued
| Ex. | Amine Prep from Prep Ex. | Product | 1. Yield 2. MH+ |
|---|---|---|---|
| 641 | 600 Step D | 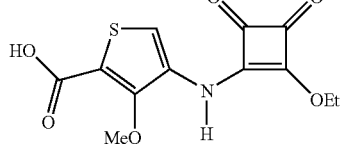 | 1. 65% 2. 138 |
EXAMPLES 360.109-360.117
Following the procedure set forth in WO 02/083524 Example 261 but using the amine from the Preparative Example indicated in the table below, the following cyclobutenedione products were obtained.
| Ex. | Amine | Product | 1. Yield 2. MH+ 3. mp (° C.) |
|---|---|---|---|
| 360.109 | 75.10A 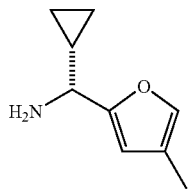 | 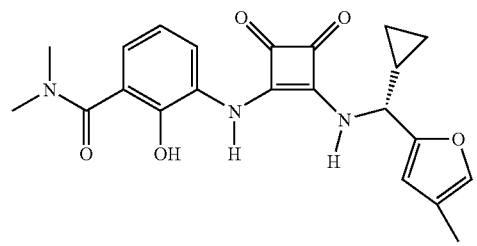 | 1. 67% 2. 410.1 3. 119–121 |
| 360.110 | 75.10B 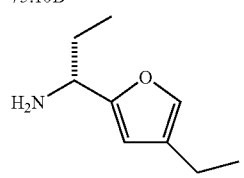 | 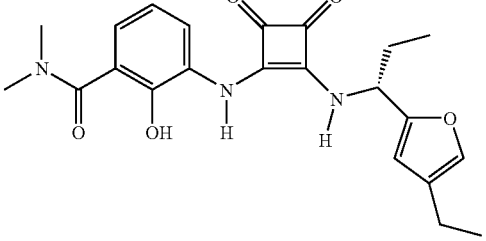 | 1. 71% 2. 412 3. 102 |
| 360.111 | 75.10C 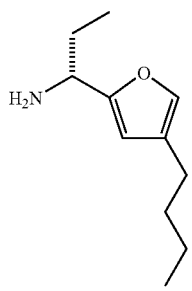 | 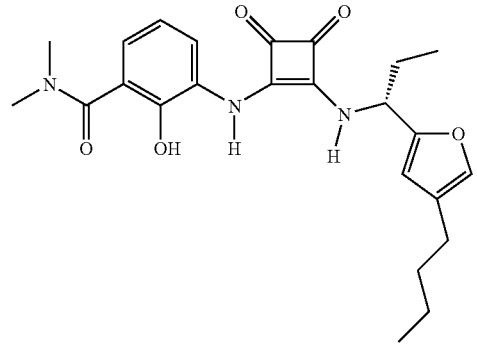 | 1. 64% 2. 440.1 3. 91–93 |

-continued

| Ex. | Amine | Product | 1. Yield<br>2. MH+<br>3. mp (° C.) |
|---|---|---|---|
| 360.112 | 75.10D | | 1. 79%<br>2. 412<br>3. 111–113 |
| 360.113 | 75.10E | | 1. 20%<br>2. 440.1<br>3. 130 (DEC) |
| 360.114 | 75.10F | | 1. 61%<br>2. 438.1<br>3. 117–119 |
| 360.115 | 75.10G | | 1. 61%<br>2. 440.1<br>3. 117–119 |
| 360.116 | 75.10H | | 1. 81%<br>2. 452<br>3. 118 |

| Ex. | Amine | Product | 1. Yield<br>2. MH+<br>3. mp (° C.) |
|---|---|---|---|
| 360.117 | 75.10J | | 1. 65%<br>2. 466<br>3. 109 |

EXAMPLES 368.32-368.45

Following the procedure set forth in WO 02/083624 Example 261 but using the amine in the table below and the cyclobutenedione intermediate from the Preparative Example indicated, the following cyclobutenedione products were obtained.

| Ex. | Amine | Prep. Ex. | Product | 1. Yield<br>2. MH+<br>3. mp (° C.) |
|---|---|---|---|---|
| 368.32 | 75.49 | 23.14 | | 1. 58%<br>2. 471.1<br>3. 149 |
| 368.33 | 75.1 | 23.15A | | 1. 33%<br>2. 440.1<br>3. 181 |
| 368.34 | 75.9 | 23.15A | | 1. 56%<br>2. 468<br>3. 180 |
| 368.35 | 75.N6 | 23.15A | | 1. 28%<br>2. 480<br>3. 186 |

-continued
| Ex. | Amine | Prep. Ex. | Product | 1. Yield 2. MH+ 3. mp (° C.) |
|---|---|---|---|---|
| 368.36 | 75.N8 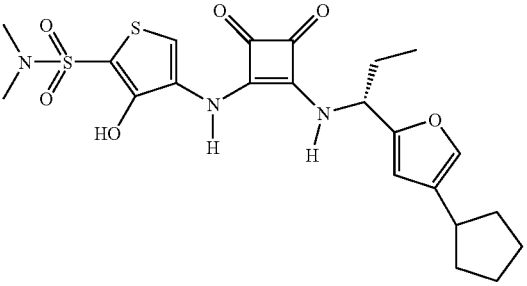 | 23.15A | 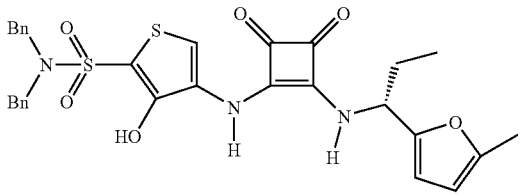 | 1. 48% 2. 494 3. 112.5 |
| 368.37 | 75.1 | 23.15B | | 1. 58% 2. 592 3. 177–179 |
| 368.38 | 75.49 | 23.15C | | 1. 69% 2. 516 3. 88–90 |
| 368.39 | 75.49 | 23.15D | | 1. 80% 2. 530 3. 134–137 |
| 368.40 | 75.49 | 23.15E | | 1. 57% 2. 454 3. 138–140 |
| 368.41 | 75.49 | 19.2 | | 1. 26% 2. 507 3. 162–164 |

-continued

| Ex. | Amine | Prep. Ex. | Product | 1. Yield<br>2. MH+<br>3. mp (° C.) |
|---|---|---|---|---|
| 368.42 | 3 | 23.25 | | 1. 82%<br>2. 466<br>3. 141–143 |
| 368.43 | 3 | 23.26 | | 1. 67%<br>2. 480<br>3. 139 dec |
| 368.44 | 13.29 | 23.16 | | 1. 29%<br>2. 480<br>3. 112–114 |
| 368.45 | 13.29 | 23.26 | | 1. 88%<br>2. 508<br>3. 190 dec |

EXAMPLES 1200-1212

Following the procedure set forth in WO 02/083624 Example 261 but using the prepared amine indicated in the table below, the following cyclobutenedione products were obtained.

| Ex. | Amine | Product | 1. Yield<br>2. MH+<br>3. mp (° C.) |
|---|---|---|---|
| 1200 | | | 1. 61.3%<br>2. 451.4<br>3. 108.6 |
| 1201 | | | 1. 54%<br>2. 439.5<br>3. 117.8 |
| 1202 | | | 1. 80%<br>2. 439.5<br>3. 128–131.8 |
| 1203 | | | 1. 75%<br>2. 423.4<br>3. 118–119 |
| 1204 | | | 1. 74%<br>2. 447.4<br>3. 108–111 |
| 1205 | | | 1. 42%<br>2. 415.42<br>3. 136–140 |
| 1206 | | | 1. 46%<br>2. 423.4<br>3. 114–117 |

| Ex. | Amine | Product | 1. Yield
2. MH+
3. mp (° C.) |
|---|---|---|---|
| 1207 | | | 1. 35%
2. 433.1
3. 123–128 |
| 1208 | | | 1. 42%
2. 423.4
3. 118–121 |
| 1209 | | | 1. 51%
2. 415.4
3. 112–117 |
| 1210 | | | 1. 44%
2. 415.4
3. 115–120 |
| 1211 | | | 1. 48%
2. 445.4
3. 105–110 |

EXAMPLES 1300-1309

Following the procedure set forth in WO 02/083624 Example 261 but using the prepared amine in the table below and the cyclobutenedione intermediate from the Preparative Example indicated (from either this Application of from WO 02/083624), the following cyclobutenedione products were obtained.

| Ex. | Amine | Prep. Ex. | Product | 1. Yield<br>2. MH+<br>3. mp (° C.) |
|---|---|---|---|---|
| 1300 | | 640 | | 1. 35%<br>2. 390.4<br>3. 100 |
| 1301 | | 641 | | 1. 78%<br>2. 390.4<br>3. 130 |
| 1302 | | 23.9 | | 1. 48%<br>2. 483.4<br>3. 116 |
| 1303 | | 23.9 | | 1. 46%<br>2. 443.5<br>3. 106 |
| 1304 | | 23.9 | | 1. 40%<br>2. 445.54<br>3. 102 |
| 1305 | | 23.9 | | 1. 51%<br>2. 413.4<br>3. 98 |
| 1306 | | 23.9 | | 1. 78%<br>2. 405.5<br>3. 246 |

-continued

| Ex. | Amine | Prep. Ex. | Product | 1. Yield 2. MH+ 3. mp (° C.) |
|---|---|---|---|---|
| 1307 | | 23.9 | | 1. 83% 2. 439.5 3. 129 |
| 1308 | | 23.15A | | 1. 11% 2. 519.47 3. 123 |
| 1309 | | 23.15A | | 1. 47% 2. 475 3. 113 |
| 1310 | | 23.15F | | 1. 55% 2. 496.1 3. 123–125 |
| 1311 | | 23.15F | | 1. 74% 2. 468.1 3. 116–118 |

EXAMPLES 1500-1503

If one were to follow the procedure set forth in WO 02/083624 Example 261 but using the prepared amine and the cyclobutenedione intermediate in the table below from the Preparative Example indicated, the following cyclobutenedione products could be obtained.

| Ex. | Amine from Prep Ex. | Cyclobutenedione intermediate from Prep Ex | Product |
|---|---|---|---|
| 1500 | (aniline, PhNH₂) | 26 | (structure shown) |
| 1501 | (chiral (5-methylfuran-2-yl)(isopropyl)methanamine) | 23.15F | (structure shown) |
| 1502 | (chiral (5-methylfuran-2-yl)(isopropyl)methanamine) | 24 | (structure shown) |
| 1503 | (chiral 1-(5-methylfuran-2-yl)propan-1-amine) | 24 | (structure shown) |
| 1504 | (chiral (5-methylfuran-2-yl)(isopropyl)methanamine) | 25 | (structure shown) |
| 1505 | (chiral 1-(5-methylfuran-2-yl)propan-1-amine) | 25 | (structure shown) |

While the present invention has been described in conjunction with specific embodiments set forth above, many alternatives, modifications and variations thereof will be apparent to those of ordinary skill in the art. All such alternatives, modifications and variations are intended to fall within the spirit and scope of the present invention.

What is claimed is:

1. A method of treating rheumatoid arthritis comprising administering to a patient in need of such treatment, a therapeutically effective amount of:

(a) a compound of the formula

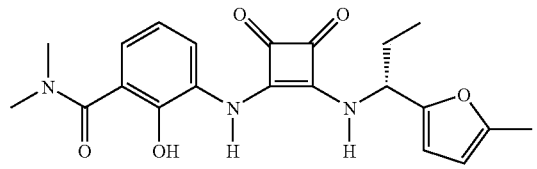

or a pharmaceutically acceptable salt thereof; and
(b) one or more drugs, agents or therapeutics selected from the group consisting of;
(i) a disease modifying antirheumatic drug;
(ii) a nonsteroidal anti-inflammatory drug;
(iii) a COX-2 selective inhibitor;
(iv) a COX-1 inhibitor;
(v) an immunosuppressive;
(vi) a steroid;
(vii) a biological response modifier and
(viii) an other anti-inflammatory agent or therapeutic.

2. The method of claim 1 wherein said compound is a calcium or sodium salt.

3. The method of claim 1 wherein said one or more drugs, agents or therapeutics is a disease modifying antirheumatic drug selected from the group consisting of methotrexate, azathioprine, leflunomide, penicillamine, a gold salt, mycophenolate, mofetil and cyclophosphamide.

4. The method of claim 1 wherein said one or more drugs, agents or therapeutics is a nonsteroidal anti-inflammatory drug selected from the group consisting of piroxicam, ketoprofen, naproxen, indomethacin, and ibuprofen.

5. The method of claim 1 wherein said one or more drugs, agents or therapeutics is a COX-2 selective inhibitor selected from the group consisting of rofecoxib and celecoxib.

6. The method of claim 1 wherein said one or more drugs, agents or therapeutics is a COX-1 inhibitor, which is piroxicam.

7. The method of claim 1 wherein said one or more drugs, agents or therapeutics is an immunosuppressive selected from the group consisting of methotrexate, cyclosporin, leflunimide, tacrolimus, rapamycin and sulfasalazine.

8. The method of claim 1 wherein said one or more drugs, agents or therapeutics is a steroid selected from the group consisting of β-methasone, prednisone, cortisone, prednisolone and dexamethasone.

9. The method of claim 1 wherein said one or more drugs, agents or therapeutics is a biological response modifier selected from the group consisting of an anti-TNF antagonist, an IL-1 antagonist, an anti-CD40 molecule, an anti-CD28 molecule, IL-10 molecule and an anti-adhesion molecule.

10. The method of claim 1 wherein said other anti-inflammatory agents or therapeutics are selected from the group consisting of a p38 kinase inhibitor, a PDE4 inhibitor, a TACE inhibitor, a chemokine receptor antagonist, thalidomide, and a leukotriene inhibitor.

11. The method of claim 1 wherein said one or more drugs, agents or therapeutics are selected from the group consisting of a COX-2 selective inhibitor, an immunosuppressive, and a steroid.

* * * * *